(12) United States Patent
Itescu

(10) Patent No.: US 7,662,794 B2
(45) Date of Patent: Feb. 16, 2010

(54) DNA ENZYME TO INHIBIT PLASMINOGEN ACTIVATOR INHIBITOR-1

(75) Inventor: Silviu Itescu, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/512,496

(22) PCT Filed: Apr. 23, 2003

(86) PCT No.: PCT/US03/12767

§ 371 (c)(1),
(2), (4) Date: Feb. 24, 2005

(87) PCT Pub. No.: WO03/091456

PCT Pub. Date: Nov. 6, 2003

(65) Prior Publication Data

US 2005/0148527 A1    Jul. 7, 2005

Related U.S. Application Data

(63) Continuation-in-part of application No. 10/128,706, filed on Apr. 23, 2002, now abandoned.

(51) Int. Cl.
*C07H 21/04* (2006.01)
*A01N 43/04* (2006.01)
*A61K 31/70* (2006.01)

(52) U.S. Cl. .................. 514/44; 536/23.1; 536/24.3; 536/24.33; 536/24.5

(58) Field of Classification Search ............... 536/23.1, 536/24.3, 24.33, 24.5; 514/44
See application file for complete search history.

(56) References Cited

U.S. PATENT DOCUMENTS 5,985,558 A    11/1999    Dean
2003/0199463 A1    10/2003    Itescu

FOREIGN PATENT DOCUMENTS

JP    2001-507688    6/2001
WO    WO-98/28317    7/1998

(Continued)

OTHER PUBLICATIONS

GenBank Accession Nos. X13338; X13323; M24067; X16383; X52906; AF069712; AF074325; X04744; X04429; X12701; M22313.1; J05206; and M33960.*

(Continued)

*Primary Examiner*—Sean McGarry
*Assistant Examiner*—Terra Cotta Gibbs
(74) *Attorney, Agent, or Firm*—John P. White; Cooper & Dunham LLP

(57) ABSTRACT

The present invention provides DNAzymes and ribozymes that specifically cleave PAI-1-encoding mRNA. The present invention also provides antisense oligonucleotides that specifically inhibit translation of PAI-1-encoding mRNA. The invention also provides various methods of inhibiting the expression of PAI-1, and methods of treating diseases by such. Finally the invention provides pharmaceutical compositions containing the instant DNAzymes, ribozymes, antisense oligonucleotides, or other inhibitors of PAI-1 expression as active ingredients.

45 Claims, 27 Drawing Sheets

FOREIGN PATENT DOCUMENTS

| WO | WO 01/51085 A | 7/2001 |
|---|---|---|
| WO | WO/01/58476 A2 | 8/2001 |

OTHER PUBLICATIONS

Peracchi, A. Prospects for antiviral ribozymes and deoxyribozymes. Reviews in Medical Virology, 2004 vol. 14:47-64.*

Nielsen, PE. Systemic delivery. The last hurdle? Gene Therapy, 2005 vol. 12:956-957.*

Santiago et al. New DNA enzyme targeting Egr-1 mRNA inhibits vascular smooth muscle proliferation and regrowth after injury. Nature Medicine, 1999 vol. 5:1264-1269.*

Liu et al. Suppression of platelet-type-12-lipoxygenase activity in human erythroleukemia cells by an RNA-cleaving DNAzyme. Biochemical and Biophysical Research Communications, 2001 vol. 284:1077-1082.*

Xiang et al. Downregulated expression of plasminogen activator inhibitor-1 augments myocardial neovascularization and reduces cardiomyocyte apoptosis after acute myocardial infarction. Journal of the American College of Cardiology, 2005 vol. 46:536-541.*

Xiang et al. Down-regulation of plasminogen activator inhibitor 1 expression promotes myocardial neovascularization by bone marrow progenitors. Journal of Exp. Med., 2004 vol. 200:1657-1666.*

International Search Report issued Aug. 14, 2003 in connection with International Application No. PCT/US03/12767.

Santorio, S.W. et al., A general purpose RNA cleaving DNA enzyme. Proc. Natl. Acad. Sci. USA. 94, 4262 4266 (1997).

Bennett, M.R. et al., Antisense therapy for angioplasty restenosis: some critical considerations. Circulation 92, 1981 1993 (1995).

Steffanson, S, and Lawrence, D.A. Nature 383, 441 443 (1996).

Heymans, S. et al. "Inhibition of plasminogen activators or matrix metalloproteinases prevents cardiac rupture but impairs . . ." Nat. Med. 5: 1135-1142.

Ginsburg, D. et al., cDNA Cloning of Human Plasminogen Activator-Inhibitor from Endothelial Cells, J. Clin. Ivest. 78(6):1673-1680 (1986).

Sane, D.C. et al., PCR-based production of a ribozyme to Plasminogen Activator-Inhibitor-1, Biotechniques 18(2):208-210 (1995).

Santorio, Stephen W. et al. A general purpose RNA-cleaving DNA enzyme, Proc. Natl. Acad. Sci. USA 94:4262-4266 (1997).

Rerolle et al., Plasminogen activator inhibitor type 1 is a potential taret in renal fibrogenesis, Kidney International, 58:1841-1850 (2000).

Branch, A., A good antisense molecule is hard to find, TIBS 23:45-50 (1998).

Usman et al., Hammerhead ribozyme engineering, Current Opinion in Structural Biology, 1:527-533 (1996).

European Supplementary Partial Search Report issued Feb. 5, 2007 in connection with E.P. 03724216.1.

Buczko, W. (1997), Pharmacology and Therapeutics 76(1-3): 161-175.

Cierniewski, C.S. (1995), European Journal of Biochemistry, 227 (1/2):494-499.

Office Action issued Sep. 26, 2003 in connection with U.S. Appl. No. 10/128,706.

Final Office Action issued Mar. 6, 2006 in connection with U.S. Appl. No. 10/128,706.

Official Action issued Sep. 26, 2007 in connection with EP 03724216.1.

Official Action issued Jun. 6, 2008 in connection with corresponding European Patent Application No. EP 03724216.1.

Official Action issued Jul. 30, 2008 in connection with corresponding Israeli Patent Application No. 164674.

Apr. 10, 2009 Decision of Rejection issued in the connection with the counterpart Chinese Patent Application No. 03814714.9.

Apr. 14, 2009 Official Action issued in connection with the counterpart Japanese Patent Application No. 2003-587981.

Feb. 6, 2009 Communication Pursuant to Article 94(3) EPC in connection with European Patent Application No. EP03724216.1.

Agrawal et al. (2000) "Antisense Therapeutics: Is It as Simple as Complementary Base Recognition?" *Molec. Med. Today* 6:72-81.

Liu et al. (2001) "Suppression of Platelet-Type 12-Lipoxygenase Activity in Human Erythroleukemia Cells by an RNA-Cleaving DNAzyme" *Biochem. and Biophys. Research Comms*. 284:1077-1082.

Peracchi, A. (2004) "Prospects for Antiviral Ribozymes and Deoxyribozymes" *Rev. Med. Virol.* 14:47-64.

Santiago et al. (1999) "New DNA Enzyme Targeting Egr-1 mRNA Inhibits Vascular Smooth Muscle Proliferation and Regrowth After Injury" *Nature Med*. 5:1264-1269.

Sawa et al. (1994) "Inhinition of Type-1 Plasminogen Activator Inhibitor Production by Antisense Oligonucleotides in Human Vascular Endothelial and Smooth Muscle Cells" *J. Bio. Chem*. 269:14149-14152.

* cited by examiner

FIGURE 1A

```
Human PAI-I mRNA (S1)        5'AAC UUCAGG A  UG CAG AUG UCU 3'
Human PAI-1DNA enzyme(E1)    3' TG AAG TCC    AC GTC TAC 5'
                                        A   G
                                       G     G
                                       C     C
                                       A     T
                                       A     A
                                        C   G
                                         A C
                                          T Human PAI-I mRNA             5' AGG AUG CAG A  UG UCU CCA GCC 3'
Human PAI-1DNA enzyme(E3)    3' TCC TAC GTC    AC AGA GGT C 5'
                                        A   G
                                       G     G
                                       C     C
                                       A     T
                                       A     A
                                        C   G
                                         A C
                                          T Rat PAI-I mRNA (S2)          5' GAU GCA GAU G  UC UUC AGC CCU C 3'
Rat PAI-1DNA enzyme(E2)      3' TA CGT CTA     AG AAG TCG 5'
                                        A   G
                                       G     G
                                       C     C
                                       A     T
                                       A     A
                                        C   G
                                         A C
                                          T Scrambled DNA sequence(E0)   3' TG AGC AG T   AG GTC ACA 5'
                                        A   G
                                       G     G
                                       C     C
                                       A     T
                                       A     A
                                        C   G
                                         A C
                                          T
```

FIGURE 2C

Rat PAI-I mRNA (S2)    5' G AUG CAGA A UG UCU UCA GCC CU C 3'
Human PAI-I mRNA       5' AGG AUG CAGA A UG UCU CCA GCC3'
Human PAI-1 DNA enzyme(E3)  3' TCC TAC GTC    AC AGA GGT C5'
                                  A        G
                                G           C
                              G              T
                              C              
                              A              A
                                A          G
                                  C      C
                                    A  T

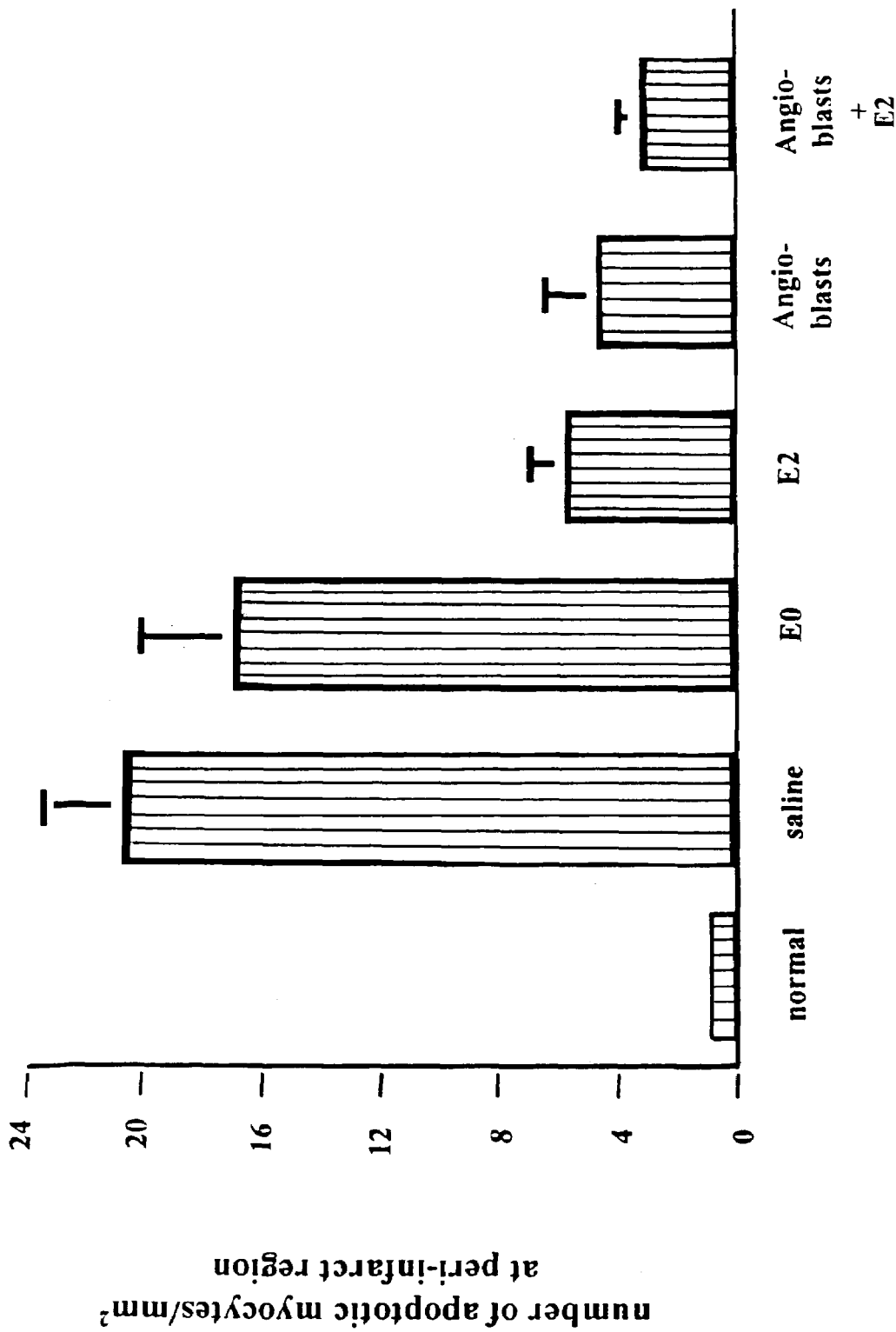

FIGURE 6

```
   1 gaattcctgc agctcagcag ccgccgccag agcaggacga accgccaatc gcaaggcacc
  61 tctgagaact tcaggatgca gatgtctcca gccctcacct gcctagtcct gggcctggcc
 121 cttgtctttg gtgaagggtc tgctgtgcac catcccccat cctacgtggc ccacctggcc
 181 tcagacttcg gggtgagggt gtttcagcag gtggcgcagg cctccaagga ccgcaacgtg
 241 gttttctcac cctatggggt ggcctcggtg ttggccatgc tccagctgac aacaggagga
 301 gaaaccagc agcagattca agcagctatg ggattcaaga ttgatgacaa gggcatggcc
 361 cccgccctcc ggcatctgta caaggagctc atggggccat ggaacaagga tgagatcagc
 421 accacagacg cgatcttcgt ccagcgggat ctgaagctgg tccagggctt catgccccac
 481 ttcttcaggc tgttccggag cacggtcaag caagtggact tttcagaggt ggagagagcc
 541 agattcatca tcaatgactg ggtgaagaca cacacaaaag gtatgatcag caacttgctt
 601 gggaaaggag ccgtggacca gctgacacgg ctggtgctgg tgaatgccct ctacttcaac
 661 ggccagtgga agactcctt ccccgactcc agcacccacc gccgctctt ccacaaatca
 721 gacggcagca ctgtctctgt gcccatgatg gctcagacca caagttcaa ctatactgag
 781 ttcaccacgc ccgatggcca ttactacgac atcctggaac tgccctacca cggggacacc
 841 ctcagcatgt tcattgctgc cccttatgaa aaagaggtgc ctctctctgc cctcaccaac
 901 attctgagtg cccagctcat cagccactgg aaaggcaaca tgaccaggct gccccgcctc
 961 ctggttctgc ccaagttctc cctggagact gaagtcgacc tcaggaagcc cctagagaac
1021 ctgggaatga ccgacatgtt cagacagttt caggctgact tcacgagtct ttcagaccaa
1081 gagcctctcc acgtcgcgca ggcgctgcag aaagtgaaga tcgaggtgaa cgagagtggc
1141 acggtggcct cctcatccac agctgtcata gtctcagccc gcatggcccc cgaggagatc
1201 atcatggaca gacccttcct ctttgtggtc cggcacaacc ccacaggaac agtcctttc
1261 atgggccaag tgatggaacc ctgaccctgg ggaaagacgc cttcatctgg gacaaaactg
1321 gagatgcatc gggaagaag aaactccgaa gaaaagaatt ttagtgttaa tgactctttc
1381 tgaaggaaga gaagacattt gccttttgtt aaaagatggt aaaccagatc tgtctccaag
1441 accttggcct ctccttggag gacctttagg tcaaactccc tagtctccac ctgagaccct
1501 gggagagaag tttgaagcac aactccctta aggtctccaa accagacggt gacgcctgcg
1561 ggaccatctg ggcacctgc ttccacccgt ctctctgccc actcgggtct gcagacctgg
1621 ttcccactga ggccctttgc aggatggaac tacggggctt acaggagctt ttgtgtgcct
1681 ggtagaaact atttctgttc cagtcacatt gccatcactc ttgtactgcc tgccaccgcg
1741 gaggaggctg gtgacaggcc aaaggccagt ggaagaaaca ccctttcatc tcagagtcca
1801 ctgtggcact ggccacccct cccagtaca ggggtgctgc aggtggcaga gtgaatgtcc
1861 cccatcatgt ggcccaactc tcctggcctg gccatctccc tccccagaaa cagtgtgcat
1921 gggttatttt ggagtgtagg tgacttgttt actcattgaa gcagatttct gcttcctttt
1981 attttatag gaatagagga agaaatgtca gatgcgtgcc cagctcttca cccccaatc
2041 tcttggtggg gaggggtgta cctaaatatt tatcatatcc ttgcccttga gtgcttgtta
2101 gagagaaaga gaactactaa ggaaaataat attatttaaa ctcgctccta gtgtttcttt
2161 gtggtctgtg tcaccgtatc tcaggaagtc cagccacttg actggcacac accctccgg
2221 acatccagcg tgacggagcc cacactgcca ccttgtggcc gcctgagacc ctcgcgcccc
2281 ccgcgccccc cgcgcccctc tttttccct tgatggaaat tgaccataca atttcatcct
2341 ccttcagggg atcaaaagga cggagtgggg ggacagagac tcagatgagg acagagtggt
2401 ttccaatgtg ttcaatagat ttaggagcag aaatgcaagg ggctgcatga cctaccagga
2461 cagaactttc cccaattaca gggtgactca cagccgcatt ggtgactcac ttcaatgtgt
2521 catttccggc tgctgtgtgt gagcagtgga cacgtgaggg ggggtgggt gagagagaca
2581 ggcagctcgg attcaactac cttagataat atttctgaaa acctaccagc cagagggtag
2641 ggcacaaaga tggatgtaat gcactttggg aggccaaggc gggaggattg cttgagccca
2701 ggagttcaag accagcctgg caacatacc aagacccccg tctcttaaa aatatatata
2761 ttttaaatat acttaaatat atatttctaa tatcttaaa tatatatata tattttaaag
2821 accaatttat gggagaattg cacacagatg tgaaatgaat gtaatctaat agaagc
```

FIGURE 7

```
   1 ccccgagag ctttgtgaag gaggaacgct gcacaccgc ctcccgcagc acacagccaa
  61 ccacagctga gcgacacgca acaagagcca atcacaaggc acttccgaaa gctccaggat
 121 gcagatgtct tcagccctca cttgcctcac cctgggcctg gttctggtct ttgggaaagg
 181 gttcgcttca cccttccag agtcccatac agcccagcag gccaccaact tcggagtaaa
 241 agtgtttcag catgtggtcc aggcctccaa agaccgaaat gtggtcttct ctccctacgg
 301 cgtgtcctcg gtgctggcta tgctgcagct gaccacagca gggaaaaccc ggcagcagat
 361 ccaagatgct atgggattca atatcagtga gaggggcaca gctcctgccc tccgaaagct
 421 ctccaaggag ctcatggggt catggaacaa gaatgagatc agtactgcgg acgccatctt
 481 tgtccagcgg gacctagagc tggtccaggg cttcatgccc cacttcttca agctcttccg
 541 gaccacggtg aagcaggtgg acttctcaga ggtggaaaga gccagattca tcatcaacga
 601 ctgggtggag aggcacacca aaggtatgat cagtgactta ctggccaagg gggctgtaaa
 661 tgagctgaca cgcctggtgc tggtgaacgc cctctatttc aacggccaat ggaagacccc
 721 cttcttagag gccagcaccc accagcgcct gttccacaag tctgatggta gcaccatctc
 781 cgtgcccatg atggctcaga acaacaagtt caactacact gagttcacca ctccggatgg
 841 gcacgagtac gacatcctgg aactgcccta ccacggcgaa accctcagca tgttcattgc
 901 agcacccttt gaaaaagatg tgccctctc cgccatcacc aacatttgg acgctgagct
 961 catcagacaa tggaagagca acatgaccag gctgccccgc ctcctcatcc tgcctaagtt
1021 ctctctggag actgaagtgg acctcagagg gccctggag aagctgggca tgactgacat
1081 cttcagctca acccaggccg acttcacaag tctttccgac caagagcagc tctctgtagc
1141 acaagcacta caaaggtca agatcgaggt gaacgagagc ggcacagtgg cgtcttcctc
1201 cacagccatt ctagtctcag cccgcatggc ccccacggag atggttttag accgatcctt
1261 tctctttgtg gttcggcaca atccaacaga gacaatcctc ttcatgggcc agctgatgga
1321 gccttgagag tgggatgaga agcctttcct tgggacaaa actggacgtg ttataagcag
1381 agactctgaa gaaaagaatt gttttaagga ctctttgggg agaaagagaa ggcctttctt
1441 tcttaccccg gcactggtaa atcttccaa ccagcctccc agacctcaga ctctcgaaga
1501 ggaaagagtc taactccctc actagggacc tatcttacta aggtctcatc caaccataga
1561 actcacagaa tctggatctg cccagcattc agcctttgga cccagttccc accaaggcc
1621 cagcagggcc aacccactac gccttcactc agcaaagtct tttgtgttcc agtcacactc
1681 tgggtacctc ttgtatcgtc ctccattgct atgaaggatg acccaggcca aaggaagaag
1741 cactgtccta tctcaaggtc cactgtggaa atgaacacct tgcccatccc caaggggcag
1801 cagatagaca gatcgaatga tcgcccgata tcaagccttc tcccagctcc cgtcctgccc
1861 tcccttccct gacagccgcc ttgtgttatt tcagagtgta gatgacttgt ttacagcttt
1921 tttcgaccca caaacttttc tcattttgaa agcgtgaaag aaaggtcaga tgtgcacgtg
1981 ccttgctctt tatcctgggt ctccctgtga ggggagaggg gtcctgggga gattccaggg
2041 gtgtgattga atattatct tgtttatctt atacgttgt tggggagaag aagcactatt
2101 aaggagaaag ccttttattt aaaccatggc atatggtgtc ccatttgggg tctgtatccc
2161 tgtatgtcag ggaggcatca ctccacaaac ccgcccctcg ggtggcccgg cgtcgggct
2221 cacactgccg cctagtggca gccgaacacg cccttgcccc atccctcccc cgcatcctcc
2281 cccgtggctc ttttccttag ggatcttgcc aaggtgatgc ttggcagccc acggtaaagg
2341 aaggggaaa aagattaggt gggagagaga gagagagaga gagagagaga gagagagaga
2401 gagagagaga gagagagaga gagagagaga aagagagaga gatgtttgag agagggcaaa
2461 gtggtttcaa attttccaa tacattcaga agccgagtgg gaaaggggc tgtgtgacct
2521 aacaggacag aactttctcc aattactggg tgactcagct gcactggtga ctcacttcaa
2581 tgtgtcattt ccggctgctg taagtgagca gtggacacgt gggggggggg gggtgaggat
2641 gaaagaaaca gccagctcct ggtcaaccac cttagttaga taatcttttt tgaaagcttc
2701 ctagctgggg gtatgatcag aaaaccaatt tactgaaaaa ctgcacagga aggtaacgtg
2761 aatctaattt catagcgggc cgctctgcat ccgttacatc tccactggaa aaaataatc
2821 attttctttt tgtgtgtgtg tgtgtgtttt agcttttctc cctctccctc tttctctctc
2881 atttcattat gcactggata accatacacc gtgtaccaca ggggcccaaa tgtggggtca
2941 catggtcttg aattttgtgg ggtacatatg cctttgtttg tttgttttca cttttgatat
3001 ataaacaggt aaatgtgttt ttaaaaaata ataaaaatag agaatatgca gac
```

FIGURE 8

```
MQMSPALTCL VLGLALVFGE GSAVHHPPSY VAHLASDFGV RVFQQVAQAS KDRNVVFSPY    60
GVASVLAMLQ LTTGGETQQQ IQAAMGFKID DKGMAPALRH LYKELMGPWN KDEISTTDAI   120
FVQRDLKLVQ GFMPHFFRLF RSTVKQVDFS EVERARFIIN DWVKTHTKGM ISNLLGKGAV   180
DQLTRLVLVN ALYFNGQWKT PFPDSSTHRR LFHKSDGSTV SVPMMAQTNK FNYTEFTTPD   240
GHYYDILELP YHGDTLSMFI AAPYEKEVPL SALTNILSAQ LISHWKGNMT RLPRLLVLPK   300
FSLETEVDLR KPLENLGMTD MFRQFQADFT SLSDQEPLHV AQALQKVKIE VNESGTVASS   360
STAVIVSARM APEEIIMDRP FLFVVRHNPT GTVLFMGQVM EP                     402
```

FIGURE 9

```
MQMSSALTCL TLGLVLVFGK GFASPLPESH TAQQATNFGV KVFQHVVQAS KDRNVVFSPY    60
GVSSVLAMLQ LTTAGKTRQQ IQDAMGFNIS ERGTAPALRK LSKELMGSWN KNEISTADAI   120
FVQRDLELVQ GFMPHFFKLF RTTVKQVDFS EVERARFIIN DWVERHTKGM ISDLLAKGAV   180
NELTRLVLVN ALYFNGQWKT PFLEASTHQR LFHKSDGSTI SVPMMAQNNK FNYTEFTTPD   240
GHEYDILELP YHGETLSMFI AAPFEKDVPL SAITNILDAE LIRQWKSNMT RLPRLLILPK   300
FSLETEVDLR GPLEKLGMTD IFSSTQADFT SLSDQEQLSV AQALQKVKIE VNESGTVASS   360
STAILVSARM APTEMVLDRS FLFVVRHNPT ETILFMGQLM EP                      402
```

FIGURE 10

```
   1 gaATtcctgc agctcagcag ccgccgccag agcaggacga accgccaATc gcaaggcacc
  61 tctgagaact tcaggATgca gATgtctcca gccctcacct gcctagtcct gggcctggcc
 121 cttgtctttg gtgaagggtc tgctgtgcac cATcccccAT cctacgtggc ccacctggcc
 181 tcagacttcg gggtgagggt gtttcagcag gtggcgcagg cctccaagga ccgcaacgtg
 241 gttttctcac cctATggggt ggcctcggtg ttggccATgc tccagctgac aacaggagga
 301 gaaacccagc agcagATtca agcagctATg ggATtcaagA TtgATgacaa gggcATggcc
 361 cccgccctcc ggcATctgta caaggagctc ATggggccAT ggaacaaggA TgagATcagc
 421 accacagacg cgATcttcgt ccagcgggAT ctgaagctgg tccagggctt cATgccccac
 481 ttcttcaggc tgttccggag cacggtcaag caagtggact tttcagaggt ggagagagcc
 541 agATtcATcA TcaATgactg ggtgaagaca cacacaaaag gtATgATcag caacttgctt
 601 gggaaaggag ccgtggacca gctgacacgg ctggtgctgg tgaATgccct ctacttcaac
 661 ggccagtgga agactcccct ccccgactcc agcacccacc gccgcctctt ccacaaATca
 721 gacggcagca ctgtctctgt gcccATgATg gctcagacca acaagttcaa ctATactgag
 781 ttcaccacgc ccgATggccA Ttactacgac ATcctggaac tgccctacca cggggacacc
 841 ctcagcATgt tcATtgctgc cccttATgaa aaagaggtgc ctctctctgc cctcaccaac
 901 ATtctgagtg cccagctcAT cagccactgg aaaggcaacA Tgaccaggct gccccgcctc
 961 ctggttctgc ccaagttctc cctggagact gaagtcgacc tcaggaagcc cctagagaac
1021 ctgggaATga ccgacATgtt cagacagttt caggctgact tcacgagtct ttcagaccaa
1081 gagcctctcc acgtcgcgca ggcgctgcag aaagtgaagA Tcgaggtgaa cgagagtggc
1141 acggtggcct cctcATccac agctgtcATa gtctcagccc gcATggcccc cgaggagATc
1201 ATcATggaca gacccttcct ctttgtggtc cggcacaacc cacaggaac agtccttttc
1261 ATgggccaag tgATggaacc ctgaccctgg ggaaagacgc cttcATctgg gacaaaactg
1321 gagATgcATc gggaaagaag aaactccgaa gaaagaATt ttagtgttaa tgactctttc
1381 tgaaggaaga gaagacATtt gccttttgtt aaaagATggt aaaccagATc tgtctccaag
1441 accttggcct ctccttggag gacctttagg tcaaactccc tagtctccac ctgagaccct
1501 gggagagaag tttgaagcac aactccctta aggtctccaa accagacggt gacgcctgcg
1561 ggaccATctg gggcacctgc ttccacccgt ctctctgccc actcgggtct gcagacctgg
1621 ttcccactga ggcccttttgc aggATggaac tacggggctt acaggagctt ttgtgtgcct
1681 ggtagaaact ATttctgttc cagtcacATt gccATcactc ttgtactgcc tgccaccgcg
1741 gaggaggctg gtgacaggcc aaaggccagt ggaagaaaca cccttttcATc tcagagtcca
1801 ctgtggcact ggccaccccct ccccagtaca ggggtgctgc aggtggcaga gtgaATgtcc
1861 cccATcATgt ggcccaactc tcctggcctg gccATctccc tccccagaaa cagtgtgcAT
1921 gggttATttt ggagtgtagg tgacttgttt actcATtgaa gcagATttct gcttcctttt
1981 ATttttATag gaATagagga agaaATgtca gATgcgtgcc cagctcttca cccccccaATc
2041 tcttggtggg gaggggtgta cctaaATATt tATcATATcc ttgcccttga gtgcttgtta
2101 gagagaaaga gaactactaa ggaaaATaAT ATtATttaaa ctcgctccta gtgtttcttt
2161 gtggtctgtg tcaccgtATc tcaggaagtc cagccacttg actggcacac acccctccgg
2221 acATccagcg tgacggagcc cacactgcca ccttgtggcc gcctgagacc ctcgcgcccc
2281 ccgcgcccc cgcgcccctc ttttccccct tgATggaaAT tgaccATaca ATttcATcct
2341 ccttcagggg ATcaaaagga cggagtgggg ggacagagac tcagATgagg acagagtggt
2401 ttccaATgtg ttcaATagAT ttaggagcag aaATgcaagg ggctgcATga cctaccagga
2461 cagaactttc cccaATtaca gggtgactca cagccgcATt ggtgactcac ttcaATgtgt
2521 cATttccggc tgctgtgtgt gagcagtgga cacgtgaggg gggggtgggt gagagagaca
2581 ggcagctcgg ATtcaactac cttagATaAT ATtctgaaa acctaccagc cagagggtag
2641 ggcacaaaga tggATgtaAT gcactttggg aggccaaggc gggaggATtg cttgagccca
2701 ggagttcaag accagcctgg gcaacATacc aagaccccg tctctttaaa aATATATATa
2761 ttttaaATAT acttaaATAT ATATtctaa tATctttaaa tATATATATa tATtttaaag
2821 accaATttAT gggagaATtg cacacagATg tgaaATgaAT gtaATctaAT agaagc
```

FIGURE 11

```
   1 gaattcctgc agctcagcag ccgccgccag agcaggACga ACcgccaatc gcaaggcACc
  61 tctgagaACt tcaggatgca gatgtctcca gccctcACct gcctagtcct gggcctggcc
 121 cttgtctttg gtgaaggGtc tgctgtgcAC catccccat cctACgtggc ccACctggcc
 181 tcagACttcg gggtgagggt gtttcagcag gtggcgcagg cctccaaggA CcgcaACgtg
 241 gttttctcAC cctatggggt ggcctcggtg ttggccatgc tccagctgAC aACaggagga
 301 gaaACccagc agcagattca agcagctatg ggattcaaga ttgatgACaa gggcatggcc
 361 cccgccctcc ggcatctgtA Caaggagctc atggggccat ggaACaagga tgagatcagc
 421 ACcACagACg cgatcttcgt ccagcgggat ctgaagctgg tccagggctt catgccccAC
 481 ttcttcaggc tgttccggag cACggtcaag caagtggACt tttcagaggt ggagagagcc
 541 agattcatca tcaatgACtg ggtgaagACA CACACaaaag gtatgatcag caACttgctt
 601 gggaaaggag ccgtggACca gctgACACgg ctggtgctgg tgaatgccct ctACttcaAC
 661 ggccagtgga agACtcccttccccgACtcc agcACccACc gccgcctctt ccACaaatca
 721 gACggcagcA Ctgtctctgt gcccatgatg gctcagACca ACaagttcaA CtatACtgag
 781 ttcACcACgc ccgatggcca ttACtACgAC atcctggaAC tgccctACcA CggggACACc
 841 ctcagcatgt tcattgctgc ccttatgaa aaagaggtgc ctctctctgc cctcACcaAC
 901 attctgagtg cccagctcat cagccACtgg aaaggcaACa tgACcaggct gccccgcctc
 961 ctggttctgc ccaagttctc cctggagACt gaagtcgACc tcaggaagcc ctagagaAC
1021 ctgggaatgA CcgACatgtt cagACagttt caggctgACt tcACgagtct ttcagACcaa
1081 gagcctctcc ACgtcgcgca ggcgctgcag aaagtgaaga tcgaggtgaa cgagagtggc
1141 ACggtggcct cctcatccAC agctgtcata gtctcagccc gcatggcccc cgaggagatc
1201 atcatggACa gACccttcct ctttgtggtc cggcACaACc ccACaggaAC agtccttttc
1261 atgggccaag tgatggaACc ctgACcctgg ggaaagACgc cttcatctgg gACaaaACtg
1321 gagatgcatc gggaagaag aaACtccgaa gaaagaatt ttagtgttaa tgACtctttc
1381 tgaaggaaga gaagACattt gcctttgtt aaaagatggt aaACcagatc tgtctccaag
1441 ACcttggcct ctccttggag gACctttagg tcaaACtccc tagtctccAC ctgagACcct
1501 gggagagaag tttgaagcAC aACtccctta aggtctccaa ACcagACggt gACgcctgcg
1561 ggACcatctg gggcACctgc ttccACccgt ctctctgccc ACtcgggtct gcagACctgg
1621 ttcccACtga ggcccttttgc aggatggaAC tACggggctt ACaggagctt ttgtgtgcct
1681 ggtagaaACt atttctgttc cagtcACatt gccatcACtc ttgtACtgcc tgccACcgcg
1741 gaggaggctg gtgACaggcc aaaggccagt ggaagaaACa ccctttcatc tcagagtcca
1801 ctgtggcACt ggccACccct ccccagtACa ggggtgctgc aggtggcaga gtgaatgtcc
1861 cccatcatgt ggcccaACtc tcctggcctg gccatctccc tccccagaaa cagtgtgcat
1921 gggttatttt ggagtgtagg tgACttgttt ACtcattgaa gcagatttct gcttcctttt
1981 attttatag gaatagagga agaaatgtca gatgcgtgcc cagctcttca ccccccaatc
2041 tcttggtggg gagggGtgta cctaaatatt tatcatatcc ttgcccttga gtgcttgtta
2101 gagagaaaga gaACtACtaa ggaaaataat attatttaaa ctcgctccta gtgtttcttt
2161 gtggtctgtg tcACcgtatc tcaggaagtc cagccACttg ACtggcACAC ACccctccgg
2221 ACatccagcg tgACggagcc cACACtgcca ccttgtggcc gcctgagACc ctcgcgcccc
2281 ccgcgccccc cgcgcccctc ttttccccct tgatggaaat tgACcatACa atttcatcct
2341 ccttcagggg atcaaaagga cggagtgggg ggACagagAC tcagatgagg ACagagtggt
2401 ttccaatgtg ttcaatagat ttaggagcag aaatgcaagg ggctgcatga cctACcagga
2461 cagaACtttc cccaattACa gggtgACtca cagccgcatt ggtgACtcAC ttcaatgtgt
2521 catttccggc tgctgtgtgt gagcagtgga cACgtgaggg ggggtgggt gagagagACa
2581 ggcagctcgg attcaACtAC cttagataat atttctgaaa ACctACcagc cagagggtag
2641 ggcACaaaga tggatgtaat gcACtttggg aggccaaggc gggaggattg cttgagccca
2701 ggagttcaag ACcagcctgg gcaACatACc aagACccccg tctctttaaa aatatatata
2761 tttaaatat ACttaaatat atatttctaa tatctttaaa tatatatata tattttaaag
2821 ACcaatttat gggagaattg cACACagatg tgaaatgaat gtaatctaat agaagc
```

FIGURE 12

```
  76                        atgca gatgTcTcca gcccTcacct gccTagTccT gggcctggcc
 121 cTgTcTTtg gtgaagggTc tgctgtgcac caTcccccaT ccTacgtggc ccacctggcc
 181 TcagacTTcg gggtgagggt gTTTcagcag gtggcgcagg ccTccaagga ccgcaacgtg
 241 gTTTcTcac ccTatggggt ggccTcggtg Ttggccatgc Tccagctgac aacaggagga
 301 gaaacccagc agcagaTTca agcagcTatg ggaTTcaaga Ttgatgacaa gggcatggcc
 361 cccgcccTcc ggcaTctgTa caaggagcTc atggggccat ggaacaagga tgagaTcagc
 421 accacagacg cgaTcTTcgT ccagcgggaT ctgaagctgg Tccagggz cTT catgccccac
 481 TtcTTcaggc TgTTccggag cacggTcaag caagtggacT TTTcagaggt ggagagagcc
 541 agaTTcaTca Tcaatgactg ggtgaagaca cacacaaaag gTatgaTcag caacTTgcTt
 601 gggaaaggag ccgtggacca gctgacacgg ctggtgctgg tgaatgcccT cTacTTcaac
 661 ggccagtgga agacTccccT cccgacTcc agcacccacc gccgccTcTT ccacaaaTca
 721 gacggcagca ctgTcTctgt gcccatgatg gcTcagacca acaagTTcaa cTaTactgag
 781 TTcaccacgc TcaTtgctgT cccagcTcaT aTcctggaac tgccccTacca cggggacacc
 841 cTcagcatgT cccTTatgaa aaagaggtgc cTcTcTctgc ccTcaccaac
 901 aTTctgagtg cccagcTcaT cagccactgg aaaggcaaca tgaccaggct gccccgccTc
 961 ctggTTctgc ccaagTTcTc cctggagact gaagTcgacc Tcaggaagcc ccTagagaac
1021 ctgggaatga ccgacatgTT cagacagTTT caggctgacT TcacgagTcT TTcagaccaa
1081 gagccTcTcc acgTcgcgca ggcgctgcag aaagtgaaga Tcgaggtgaa cgagagtggc
1141 acggtggccT ccTcaTccac agctgTcaTa gTcTcagccc gcatggcccc cgaggagaTc
1201 aTcatggaca gaccccTTccT cTTtgtggTc cggcacaacc ccacaggaac cgaggagaTc agTccTTTTc
1261 atgggccaag tgatggaacc ctga
```

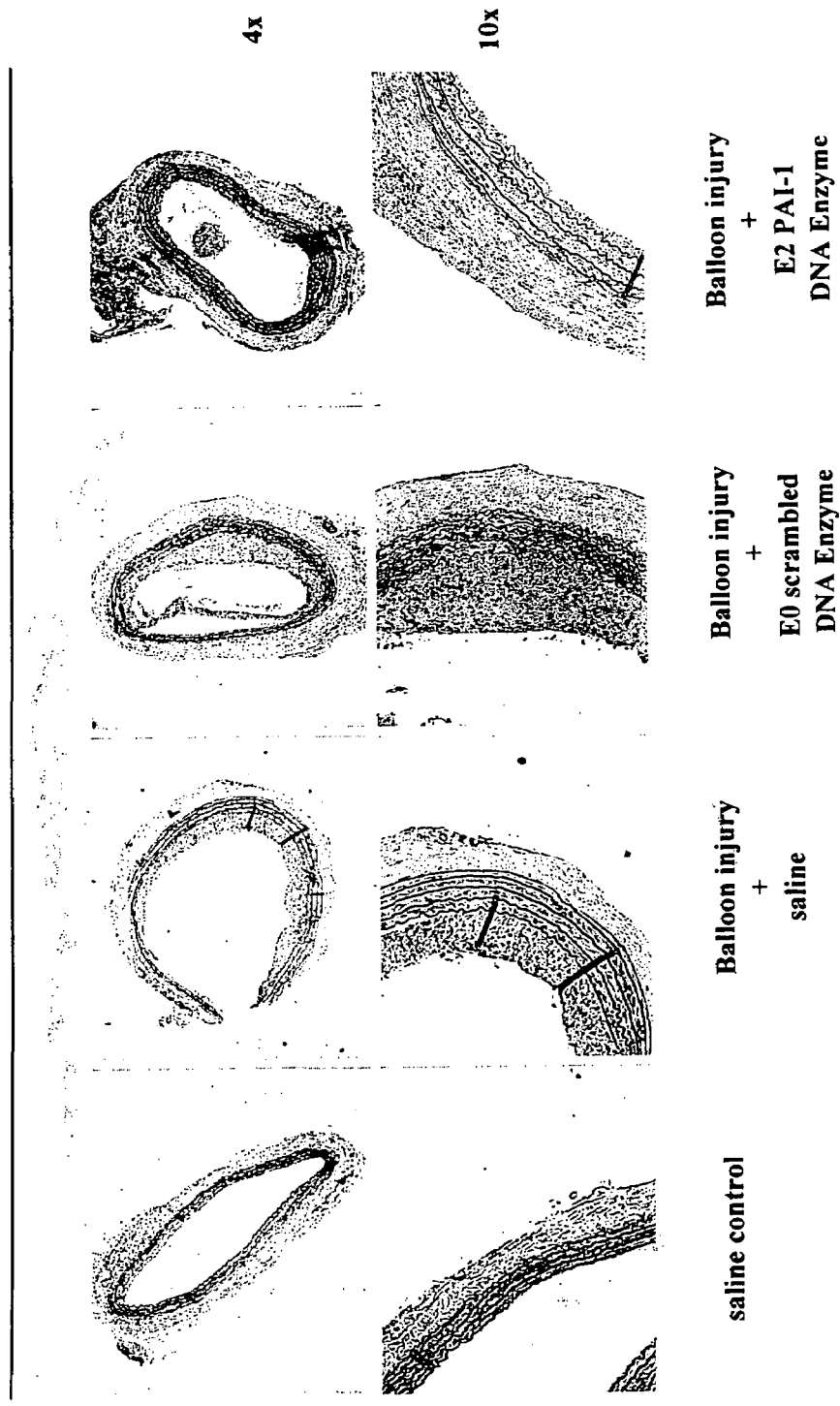
*FIGURE 13* PAI-1 DNA Enzyme Prevents Rat Carotid Artery Neointima Formation After Balloon Angioplasty Injury

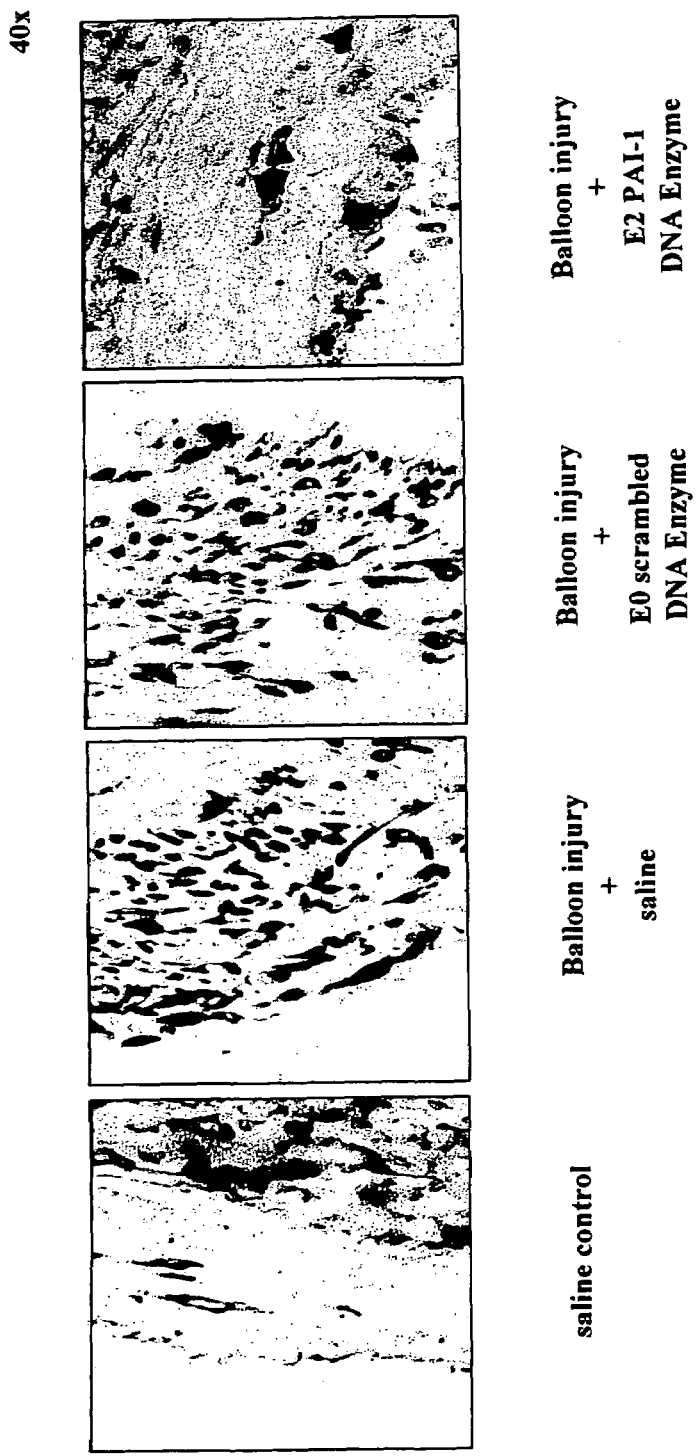
FIGURE 15  PAI-1 DNA Enzyme Prevents Smooth Muscle Cell Proliferation In Neointima After Balloon Angioplasty Injury

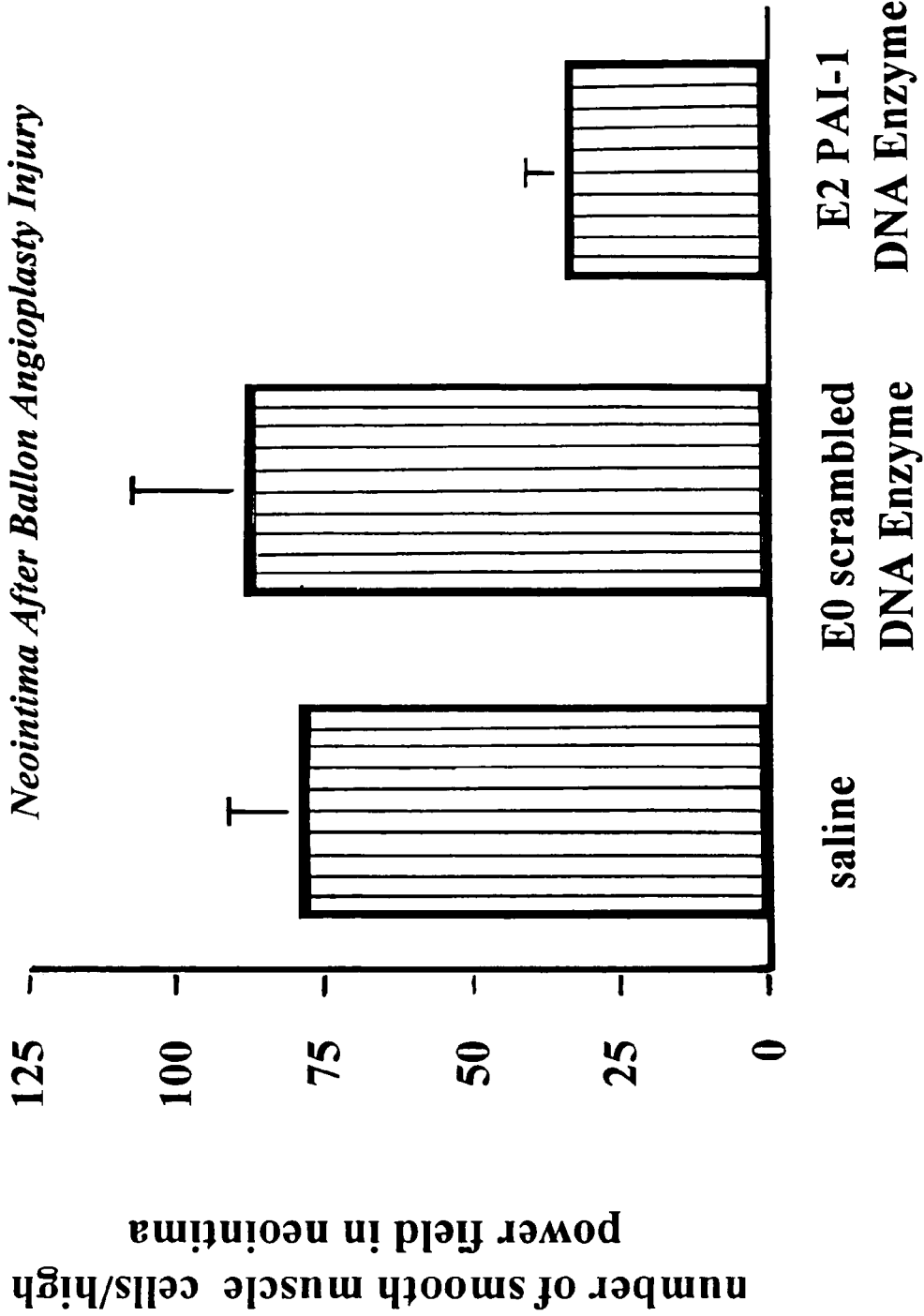

DNA ENZYME TO INHIBIT PLASMINOGEN ACTIVATOR INHIBITOR-1

This application is a 371 national stage of PCT International Application No. PCT/US03/12767, filed Apr. 23, 2003, designating the United States of America, which is a continuation-in-part and claims priority of U.S. application Ser. No. 10/128,706, filed Apr. 23, 2002, now abandoned, the contents of which are hereby incorporated by reference.

Throughout this application, various publications are referenced in parentheses by arabic numbers. Full citations for these references may be found at the end of the specification immediately preceding the claims. The disclosures of these publications in their entireties are hereby incorporated by reference into this application to more fully describe the state of the art to which this invention pertains.

BACKGROUND

After a myocardial infarction, the subsequent cardiomyocyte necrosis stimulates a wound healing response characterized by migration of inflammatory cells into the affected myocardium, extracellular matrix degradation, and neovascularization. Each of these components appears to require activation of latent metalloproteinases by plasmin, which is derived from plasminogen through activation by urokinase-type plasminogen activator (u-PA) expressed on the surface of the infiltrating bone-marrow derived cells (1-3). More recently, it has been suggested that the role of cell surface u-PA may be to facilitate exposure of cryptic cell attachment sites necessary for cell migration (4). This appears to involve direct interaction between u-PA and plasminogen activator inhibitor-1 (PAI-1), which, in its native state, is complexed to vitronectin (4,5). Reaction of PAI-1 with a proteinase, such as u-PA, results in a rapid conformational change that causes it to dissociate from vitronectin and increase its affinity for the low density lipoprotein receptor (6), leading to its clearance and degradation. Removal of PAI-1 from vitronectin exposes the epitope on vitronectin necessary for binding to another of its ligands, the integrin alpha v beta 3 (4,7). Since interactions between the cell surface integrin alpha v beta 3 and tissue vitronectin have been shown to be important in the development of angiogenesis (4,8,9), we hypothesized that excessive PAI-1 protein expression after myocardial infarction might prevent optimal neovascularization by bone marrow-derived angioblasts and that inhibition of PAI-1 expression would promote neovascularization.

In order to develop an approach to inhibit PAI-1 expression which would have clinical applicability, we examined various potential strategies for inhibiting specific mRNA activity.

Antisense oligonucleotides hybridize with their complementary target site in mRNA, blocking translation to protein by sterically inhibiting ribosome movement or by triggering cleavage by endogenous RNAse H (10). Although current constructs are made more resistant to degradation by serum through phosphorothioate linkages, non-specific biological effects due to "irrelevant cleavage" of non-targeted mRNA remains a major concern (11).

Ribozymes are naturally-occurring RNA molecules that contain catalytic sites, making them more potent agents than antisense oligonucleotides. However, wider use of ribozymes has been hampered by their susceptibility to chemical and enzymatic degradation and restricted target site specificity (12).

A new generation of catalytic nucleic acids has been described containing DNA molecules with catalytic activity for specific RNA sequences (13-16). These DNA enzymes exhibit greater catalytic efficiency than hammerhead ribozymes, producing a rate enhancement of approximately 10 million-fold over the spontaneous rate of RNA cleavage, offer greater substrate specificity, are more resistant to chemical and enzymatic degradation, and are far cheaper to synthesize.

SUMMARY

This invention provides a catalytic nucleic acid that specifically cleaves an mRNA encoding a Plasminogen Activator Inhibitor-1 (PAI-1) comprising, in 5' to 3' order:
(a) consecutive nucleotides defining a first binding domain of at least 4 nucleotides;
(b) consecutive nucleotides defining a catalytic domain located contiguous with the 3' end of the first binding domain, and capable of cleaving the PAI-1-encoding mRNA at a predetermined phosphodiester bond; and
(c) consecutive nucleotides defining a second binding domain of at least 4 nucleotides located contiguous with the 3' end of the catalytic domain, wherein the sequence of the nucleotides in each binding domain is complementary to a sequence of ribonucleotides in the PAI-1-encoding mRNA and wherein the catalytic nucleic acid hybridizes to and specifically cleaves the PAI-1-encoding mRNA.

This invention further provides a pharmaceutical composition comprising the instant catalytic nucleic acid and a pharmaceutically acceptable carrier.

This invention further provides method of specifically inhibiting the expression of PAI-1 in a cell that would otherwise express PAI-1, comprising contacting the cell with the instant catalytic nucleic acid so as to specifically inhibit the expression of PAI-1 in the cell.

This invention further provides a method of specifically inhibiting the expression of PAI-1 in a subject's cells comprising administering to the subject an amount of the instant catalytic nucleic acid effective to specifically inhibit the expression of PAI-1 in the subject's cells.

This invention further provides a method of specifically inhibiting the expression of PAI-1 in a subject's cells comprising administering to the subject an amount of the instant pharmaceutical composition effective to specifically inhibit the expression of PAI-1 in the subject's cells.

This invention further provides a method of treating a cardiovascular disease in a subject involving apoptosis of a cardiomyocyte in the subject which comprises administering to the subject an amount of the instant pharmaceutical composition effective to inhibit apoptosis of the cardiomyocyte in the subject so as to thereby treat the cardiovascular disease.

This invention further provides a method of treating a fibrotic disease in a subject involving fibrogenesis which comprises administering to the subject an amount of the instant pharmaceutical composition effective to inhibit fibrogenesis in the subject so as to thereby treat the fibrotic disease.

This invention further provides an oligonucleotide comprising consecutive nucleotides that hybridizes with a PAI-1-encoding mRNA under conditions of high stringency and is between 8 and 40 nucleotides in length. This invention further provides the instant oligonucleotide, wherein the human PAI-1-encoding mRNA comprises consecutive nucleotides, the sequence of which is set forth in SEQ ID NO:5.

This invention further provides a method of treating a subject which comprises administering to the subject an amount of the instant oligonucleotide of effective to inhibit expression of a PAI-1 in the subject so as to thereby treat the subject.

This invention further provides a method of treating a cardiovascular disease in a subject involving apoptosis of a cardiomyocyte in the subject which comprises administering to the subject an amount of the instant oligonucleotide effective to inhibit apoptosis of the cardiomyocyte in the subject so as to thereby treat the cardiovascular disease.

This invention further provides a method of treating a fibrotic disease in a subject involving fibrogenesis in the subject which comprises administering to the subject an amount of the instant oligonucleotide effective to inhibit fibrogenesis in the subject so as to thereby treat the fibrotic disease.

BRIEF DESCRIPTION OF THE FIGURES

FIGS. 1(A)-(D): (A) This figure shows three DNA enzymes, termed E1 (SEQ ID NO:2), E2 (SEQ ID NO:4), and E3 (SEQ ID NO:3), containing identical 15-nucleotide catalytic domains (SEQ ID NO:1) flanked by two arms of eight nucleotides (E1, E2) or nine nucleotides (E3) with complementarity to human (E1, E3) or rat (E2) PAI-1 mRNA. This figure also shows the control DNA enzyme E0 (SEQ ID NO:7), an oligonucleotide S1 (SEQ ID NO:8), an oligonucleotide transcript (SEQ ID NO:9) and oligonucleotide S2 (SEQ ID NO:10). (B) This figure shows the 21-base oligonucleotide S1 (SEQ ID NO:8), synthesized from human PAI-1 mRNA and labeled at the 5' end with 32P, was cleaved within 2 minutes when cultured with E1 at 10:1 substrate:enzyme excess, with maximal cleavage occurring by 2 hours. (C) This figure shows E1 also cleaved larger 32P-labeled fragments of human PAI-1 mRNA, prepared by in vitro transcription, in a time- and concentration-dependent manner. (D) This figure shows the sequence-specific nature of the DNA enzymatic cleavage: the control DNA enzyme E0, containing an identical catalytic domain to E1 and E3, but scrambled sequences in the flanking arms, caused no cleavage of human PAI-1 mRNA transcripts.

FIG. 2(A)-(C): (A) This figure shows that the DNA enzyme E2 cleaved the 23-base oligonucleotide S2 (SEQ ID NO:10), synthesized from the sequence of rat PAI-1 mRNA, in a dose- and time-dependent manner. (B) This figure shows that E2 also cleaved a rat PAI-1 mRNA transcript in a dose-dependent manner by 2-4 hours to give the 156 nucleotide cleavage product. (C) This figure shows the rat S2 PAI-1mRNA transcript (SEQ ID NO:10) differs by only one nucleotide from the human mRNA PAI-1 transcript (SEQ ID NO:9) which can be cleaved by E3.

(B) This figure shows the effect of endothelial cell transfection with E2 DNA enzyme on TGF-beta mediated induction of PAI-1 protein. Endothelial cells transfected with scrambled DNA enzyme demonstrated approximately 50% increase in cytoplasmic PAI-1 E0 protein as detected by Western blot. In contrast, this effect was almost completely abrogated by transfection with the PAI-1 DNA enzyme E2. (C) This figure shows that whereas the DNA enzyme was almost completely degraded within 6 hours of cell culture in medium containing 20% serum, it remained intact during the entire 24 hours of cell culture with medium containing 2% serum. (D) This figure shows that HUVEC transfected with E1 or E3 DNA enzymes and cultured for 12 hours in 2% serum demonstrated 20% and 28% reduction in TGF-beta dependent PAI-1 activity compared with transfection with the scrambled DNA enzyme E0 (both p<0.01).

Figure 4A:
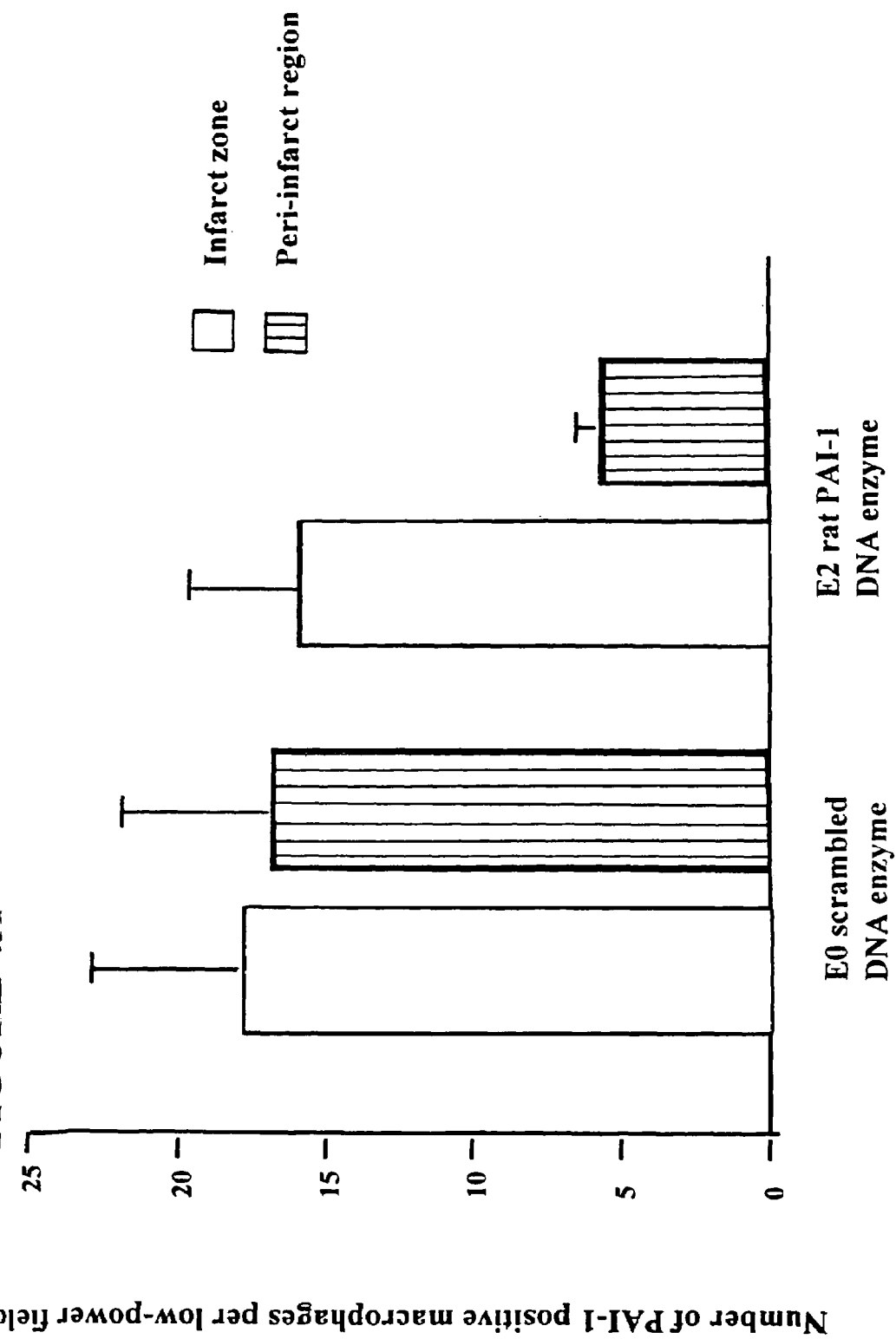
Figure 4B:
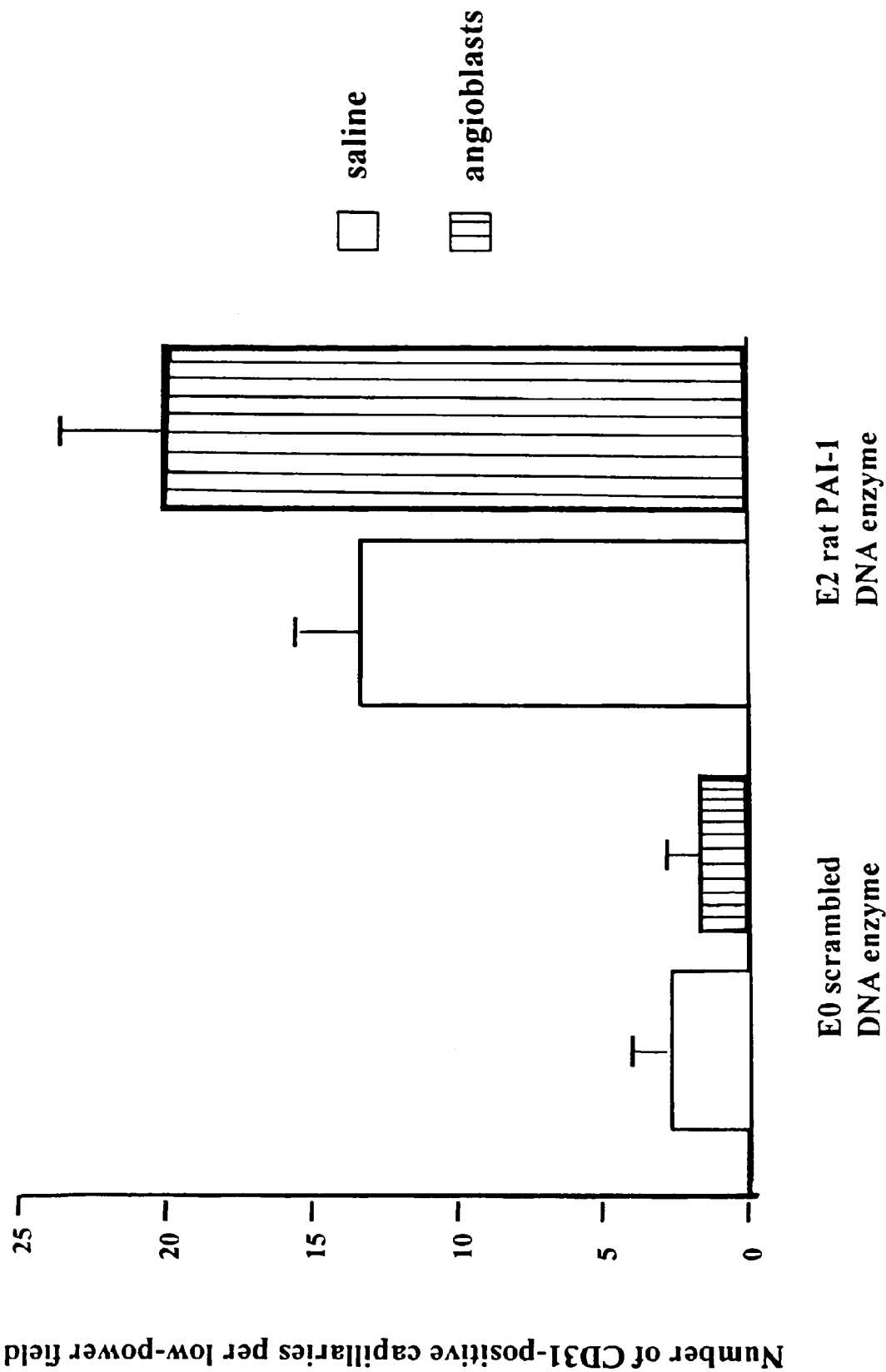
Figure 4C:
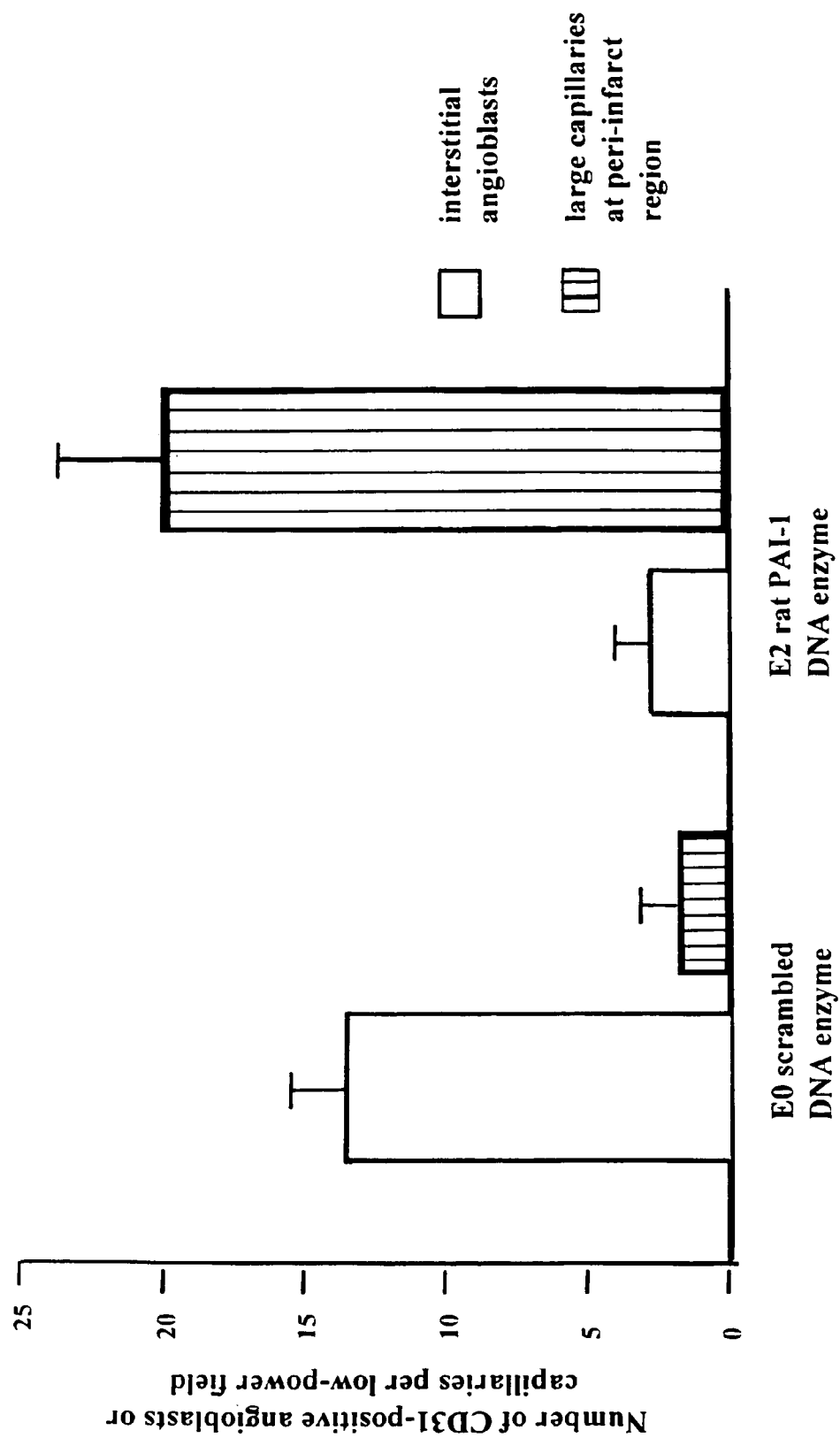

FIGS. 4(A)-(C): (A) This figure shows that at two weeks after injection with E2, PAI-1 expression in infarcted rat hearts was dramatically altered, with 71% reduction in PAI-1 expression by macrophages at the peri-infarct region (p<0.01). (B) and (C) show injection of E2 and angioblasts increased the number of CD31 positive capillaries.

Figure 5B:
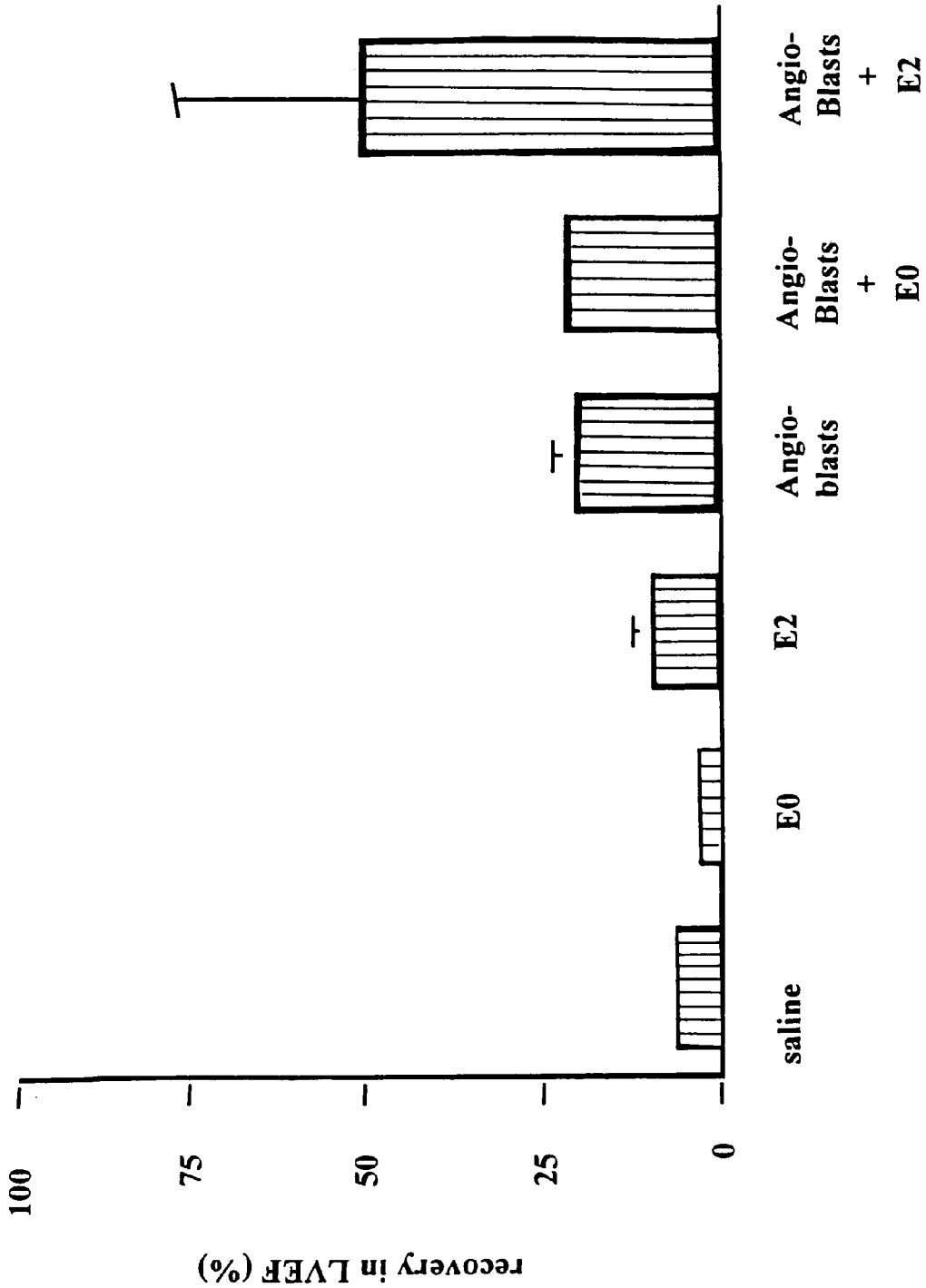

FIG. 5(A)-(B): (A) This figure shows inhibition of cardiomyocyte apoptosis in the pen-infarct region by E2. (B) This figure shows the percentage recovery in left ventricular ejection fraction (LVEF) after treatment with E2 and after treatment with E2 and angioblasts.

FIG. 6: This figure shows the DNA sequence encoding human Plasminogen Activator Inhibitor-1 protein (SEQ ID NO:5).

FIG. 7: This figure shows the DNA sequence encoding rat Plasminogen Activator Inhibitor-1 protein (SEQ ID NO:15).

FIG. 8: This figure shows the amino acid sequence of human Plasminogen Activator Inhibitor-1 protein (SEQ ID NO:6).

FIG. 9: This figure shows the amino acid sequence of rat Plasminogen Activator Inhibitor-1 protein (SEQ ID NO:16).

FIG. 10: This figure shows possible 5'-AT-3' cleavage sites on human PAI-1 mRNA (shown as corresponding DNA, SEQ ID NO:5) for catalytic deoxyribonucleic acids. Bold indicates the protein coding region, capital letters indicate consensus cleavage sites.

FIG. 11: This figure shows possible 5'-AC-3' cleavage sites on human PAI-1 mRNA (shown as corresponding DNA, SEQ ID NO:5) for catalytic deoxyribonucleic acids. Bold indicates the protein coding region, capital letters indicate consensus cleavage sites.

FIG. 12: This figure shows possible cleavage sites on human PAI-1 mRNA coding region (shown as corresponding DNA, SEQ ID NO:17) for catalytic hammerhead ribonucleic acids. Uppercase "T" represents cleavage site.

FIG. 13: This figure shows a PAI-1 catalytic DNA enzyme (E2) prevents rat carotid artery neointima formation after balloon angioplasty injury.

Figure 14:
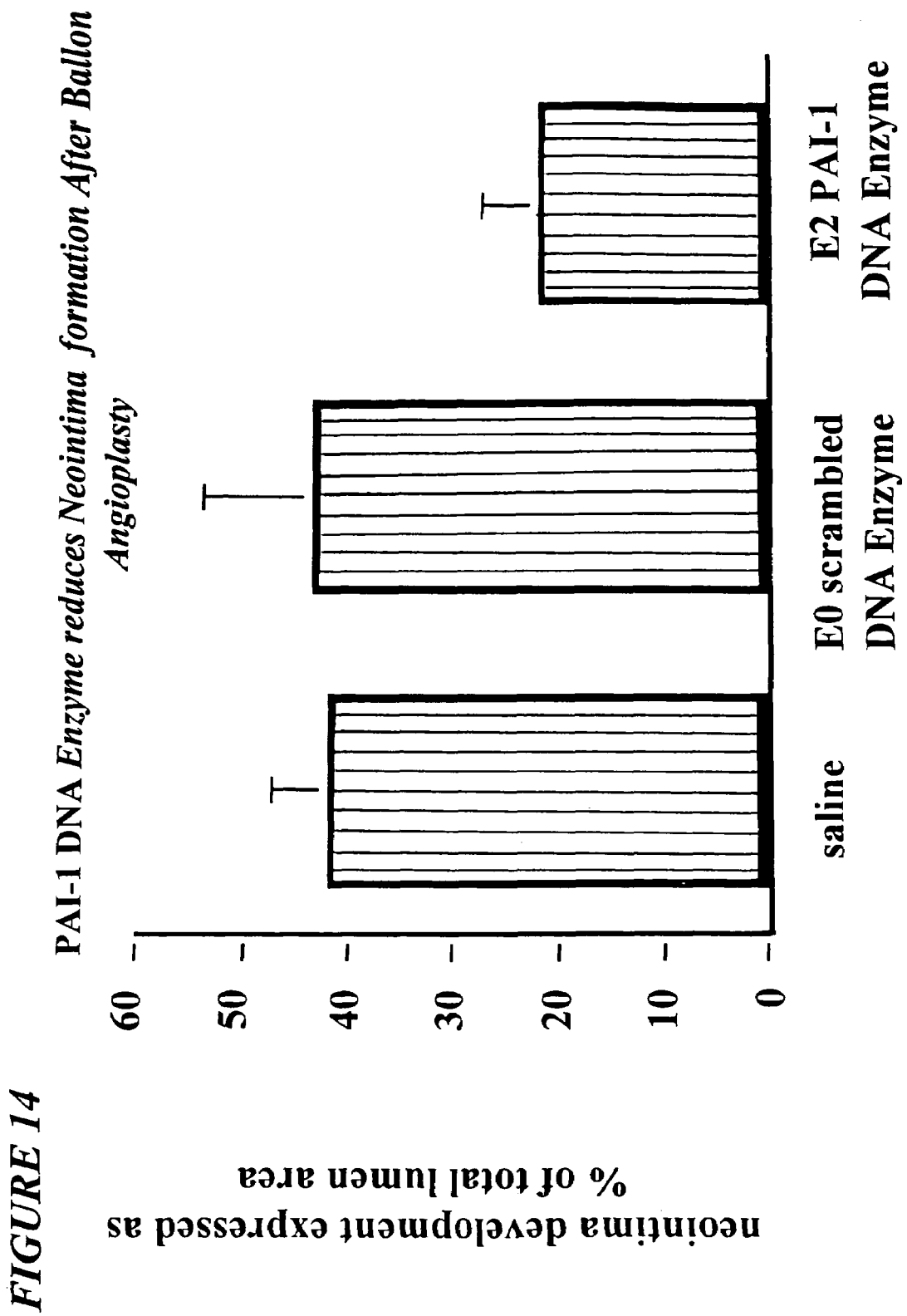

FIG. 14: This figure shows PAI-1 catalytic DNA enzyme (E2) reduces rat neointima formation after balloon angioplasty.

FIG. 15: This figure shows a PAI-1 catalytic DNA enzyme (E2) prevents smooth muscle cell proliferation in neointima formation after balloon angioplasty injury.

FIG. 16: This figure shows a PAI-1 catalytic DNA enzyme (E2) prevents smooth muscle cell proliferation in neointima formation after balloon angioplasty injury.

DETAILED DESCRIPTION

As used herein, and unless stated otherwise, each of the following terms shall have the definition set forth below.

"Administering" shall mean any of the various methods and delivery systems known to those skilled in the art. The administering can be performed, for example, via implant, transmucosally, transdermally and subcutaneously, orally, parenterally, topically, by cardiac injection, by inhalation, by catheter e.g. retrograde ureteric catheter, by intra-arterial injection, by a stent.

"Catalytic" shall mean the functioning of an agent as a catalyst, i.e. an agent that increases the rate of a chemical reaction without itself undergoing a permanent structural change.

"Consensus sequence" shall mean a nucleotide sequence of at least two residues in length between which catalytic: nucleic acid cleavage occurs. For example, consensus sequences include for catalytic deoxyribonucleic acids are purine:pyrimidine e.g. "A:U" and "G:U".

"Plasminogen Activator Inhibitor-1 Protein" shall mean the protein encoded by the nucleotide sequence identified as (SEQ ID NO:5) and having the amino acid sequence shown in SEQ ID NO:6, when identified as human and the protein encoded by the nucleotide sequence identified as SEQ ID NO:15 and having the amino acid sequence shown in SEQ ID NO:16 when identified as originating from rat, and any variants of either thereof, whether artificial or naturally occurring. Variants include, without limitation, homologues, post-translational modifications, mutants and polymorphisms.

"Plasminogen Activator Inhibitor-1 mRNA" shall mean a mRNA molecule comprising a sequence which encodes Plasminogen Activator Inhibitor-1 Protein. Plasminogen Activator Inhibitor-1 mRNA includes, without limitation, protein-encoding sequences as well as the 5' and 3' non-protein-encoding sequences.

"Hybridize" shall mean the annealing of one single-stranded nucleic acid molecule to another nucleic acid molecule based on sequence complementarity. The propensity for hybridization between nucleic acids depends on the temperature and ionic strength of their milieu, the length of the nucleic acids and the degree of complementarity. The, effect of these parameters on hybridization is well known in the art (see 38).

"Inhibit" shall mean to slow, stop or otherwise impede.

"Stringent conditions" or "Stringency", shall refer to the conditions for hybridization as defined by the nucleic acid, salt, and temperature. These conditions are well known in the art and may be altered. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions. As will be understood by those of skill in the art, the stringency of hybridization may be altered in order to identify or detect identical or related polynucleotide sequences.

"Nucleic acid" shall include any nucleic acid, including, without limitation, DNA, RNA, oligonucleotides., or polynucleotides, and analogs or derivatives thereof. The nucleotides that form the nucleic acid may be nucleotide analogs or derivatives thereof. The nucleic acid may incorporate non nucleotides.

"Nucleotides" shall include without limitation nucleotides and analogs or derivatives thereof. For example, nucleotides may comprise the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Pharmaceutically acceptable carrier" shall mean any of the various carriers known to those skilled in the art.

"Specifically cleave", when referring to the action of one of the instant catalytic deoxyribonucleic acid molecules on a target mRNA molecule, shall mean to cleave the target mRNA molecule without cleaving another mRNA molecule lacking a sequence complementary to either of the catalytic deoxyribonucleic acid molecule's two binding domains.

"Subject" shall mean any animal, such as a human, a primate, a mouse, a rat, a guinea pig or a rabbit.

The terms "DNA enzyme", "DNAzyme" and "catalytic deoxyribonucleic acid" are used synonymously.

"Vector" shall include, without limitation, a nucleic acid molecule that can be used to stably introduce a specific nucleic acid sequence into the genome of an organism.

This invention provides a catalytic nucleic acid that specifically cleaves an mRNA encoding a Plasminogen Activator Inhibitor-1 (PAI-1) comprising, in 5' to 3' order:

(a) consecutive nucleotides defining a first binding domain of at least 4 nucleotides;

(b) consecutive nucleotides defining a catalytic domain located contiguous with the 3' end of the first binding domain, and capable of cleaving the PAI-1-encoding mRNA at a predetermined phosphodiester bond; and (c) consecutive nucleotides defining a second binding domain of at least 4 nucleotides located contiguous with the 3' end of the catalytic domain, wherein the sequence of the nucleotides in each binding domain is complementary to a sequence of ribonucleotides in the PAI-1-encoding mRNA and wherein the catalytic nucleic acid hybridizes to and specifically cleaves the PAI-1-encoding mRNA.

In different embodiments the catalytic deoxyribonucleic acid molecules can cleave the PAI-1-encoding mRNA at the linkage between 5'-A(or G) and U(T)-3' (or C) i.e. at purine:pyrimidine consensus sequences. In further embodiments the catalytic deoxyribonucleic acid molecules cleaves the PAI-1 mRNA at the linkage of any 5'-AU-3'; 5'-AC-3'; 5'-GU-3'; or 5'-GC-3' site within the mRNA.

To target the human PAI-1-encoding mRNA, catalytic nucleic acids can be designed based on the consensus cleavage sites 5'-purine:pyrimidine-3' in the mRNA sequence (GenBank Accession#: M16006) (36). Those potential cleavage sites located on an open loop of the mRNA according to RNA folding software e.g. RNAdraw 2.1 are particularly preferred as targets (22). The DNA based catalytic nucleic acids can utilize the structure where two sequence-specific arms are attached to a catalytic core (SEQ ID NO:1) based on the PAI-1-encoding mRNA sequence (corresponding DNA shown as SEQ ID NO:5). Further examples of catalytic DNA structure are detailed in (23) and (24). Commercially available mouse brain polyA-RNA (Ambion) can serve as a template in the in vitro cleavage reaction to test the efficiency of the catalytic deoxyribonucleic acids.

Catalytic nucleic acid molecules can cleave PAI-1-encoding mRNA at each and any of the consensus sequences therein. Since catalytic ribo- and deoxyribo- nucleic acid consensus sequences are known, and the PAI-1-encoding mRNA sequence is known, one of ordinary skill could readily construct a catalytic ribo- or deoxyribo nucleic acid molecule directed to any of the PAI-1-encoding mRNA consensus sequences based on the instant specification. In preferred embodiments of this invention the catalytic deoxyribonucleic acids include the 10-23 structure. Cleavage of PAI-1 mRNA by DNAzyme may occur at 264 cleavage sites in the coding region of human PAI-1-encoding mRNA, including 51 5'-AT-3' (-AU-) sites, 76-AC-sites, 53-GT-(-GU-) sites and 84-GC-sites. See FIGS. 10 and 11 for AT and AC cleavage sites respectively, represented on the DNA sequence corresponding to the PAI-1-encoding mRNA.

Taking-AT-sites as a example, cleavage sites include nucleotide 76, 82, 152, 159, 254, 277, 316, 328, 333, 340, 344, 355, 374, 391, 399, 410, 415, 433, 449, 472, 543, 547, 550,554, 583, 586, 644, 717, 745, 748, 773, 794, 800, 811, 847, 853, 866, 901, 919, 939, 1027, 1036, 1120, 1125, 1168, 1183, 1198, 1201, 1204, 1261, and 1273 of SEQ ID NO:5.

Examples of catalytic ribonucleic acids include hairpin and hammerhead ribozymes. In preferred embodiments of this invention, the catalytic ribonucleic acid molecule is formed in a hammerhead (25) or hairpin motif (26,27,28), but may also be formed in the motif of a hepatitis delta virus (29), group I intron (35), RNaseP RNA (in association with an RNA guide sequence) (30,31) or Neurospora VS RNA (32,33,34). Hammerhead ribozymes can cleave any 5'-NUH-3' triplets of a mRNA, where U is conserved and N is any nucleotide and H can be C,U,A, but not G. For example, there (are 151 sites which can be cleaved by a hammerhead ribozyme in human PAI-1-encoding mRNA coding region. See FIG. 12.

Cleaving of PAI-1-encoding mRNA with catalytic nucleic acids interferes with one or more of the normal functions of PAI-1-encoding mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA.

In one embodiment the nucleotides of the first binding domain comprise at least one deoxyribonucleotide. In another embodiment the nucleotides of the second binding domain comprise at least one deoxyribonucleotide. In one embodiment the nucleotides of the first binding domain comprise at least one deoxyribonucleotide derivative. In another embodiment the nucleotides of the second binding domain comprise at least one deoxyribonucleotide derivative. In one embodiment the nucleotides of the first binding domain comprise at least one ribonucleotide. In another embodiment the nucleotides of the second binding domain comprise at least one ribonucleotide. In one embodiment the nucleotides of the first binding domain comprise at least one ribonucleotide derivative. In another embodiment the nucleotides of the second binding domain comprise at least one ribonucleotide derivative. In one embodiment the nucleotides of the first binding domain comprise at least one modified base. In another embodiment the nucleotides of the second binding domain comprise at least one modified base.

The nucleotides may comprise other bases such as inosine, deoxyinosine, hypoxanthine may be used. In addition, isoteric purine 2'deoxy-furanoside analogs, 2'-deoxynebularine or 2'deoxyxanthosine, or other purine or pyrimidine analogs may also be used. By carefully selecting the bases and base analogs, one may fine tune the hybridization properties of the oligonucleotide. For example, inosine may be used to reduce hybridization specificity, while diaminopurines may be used to increase hybridization specificity.

Adenine and guanine may be modified at positions N3, N7, N9, C2, C4, C5, C6, or C8 and still maintain their hydrogen bonding abilities. Cytosine, thymine and uracil may be modified at positions N1, C2, C4, C5, or C6 and still maintain their hydrogen bonding abilities. Some base analogs have different hydrogen bonding attributes than the naturally occurring bases. For example, 2-amino-2'-dA forms three (3), instead of the usual two (2), hydrogen bonds to thymine (T). Examples of base analogs that have been shown to increase duplex stability include, but are not limited to, 5-fluoro-2'-dU, 5-bromo-2'-dU, 5-methyl-2'-dC, 5-propynyl-2'-dC, 5-propynyl-2'-dU, 2-amino-2'-dA, 7-deazaguanosine, 7-deazadenosine, and N2-Imidazoylpropyl-2'-dG.

Nucleotide analogs may be created by modifying and/or replacing a sugar moiety. The sugar moieties of the nucleotides may also be modified by the addition of one or more substituents. For example, one or more of the sugar moieties may contain one or more of the following substituents: amino, alkylamino, araalkyl, heteroalkyl, heterocycloalkyl, aminoalkylamino, O, H, an alkyl, polyalkylamino, substituted silyl, F, Cl, Br, CN, $CF_3$, $OCF_3$, OCN, O-alkyl, S-alkyl, SOMe, $SO_2Me$, $ONO_2$, NH-alkyl, $OCH_2CH=CH_2$, $OCH_2CCH$, OCCHO, allyl, O-allyl, $NO_2$, $N_3$, and $NH_2$. For example, the 2' position of the sugar may be modified to contain one of the following groups: H, OH, OCN, O-alkyl, F, CN, $CF_3$, allyl, O-allyl, $OCF_3$, S-alkyl, SOMe, $SO_2Me$, $ONO_2$, $NO_2$, $N_3$, $NH_2$, NH-alkyl, or $OCH=CH_2$, OCCH, wherein the alkyl may be straight, branched, saturated, or unsaturated. In addition, the nucleotide may have one or more of its sugars modified and/or replaced so as to be a ribose or hexose (i.e. glucose, galactose) or have one or more anomeric sugars. The nucleotide may also have one or more L-sugars.

Representative United States patents that teach the preparation of such modified bases/nucleosides/nucleotides include, but are not limited to, U.S. Pat. Nos. 6,248,878, and 6,251,666 which are herein incorporated by reference.

The sugar may be modified to contain one or more linkers for attachment to other chemicals such as fluorescent labels. In an embodiment, the sugar is linked to one or more aminoalkyloxy linkers. In another embodiment, the sugar contains one or more alkylamino linkers. Aminoalkyloxy and alkylamino linkers may be attached to biotin, cholic acid, fluorescein, or other chemical moieties through their amino group.

Nucleotide analogs or derivatives may have pendant groups attached. Pendant groups serve a variety of purposes which include, but are not limited to, increasing cellular uptake of the molecule, enhancing degradation of the target nucleic acid, and increasing hybridization affinity. Pendant groups can be linked to the binding domains of the catalytic nucleic acid. Examples of pendant groups include, but are not limited to: acridine derivatives (i.e., 2-methoxy-6-chloro-9-aminoacridine); cross-linkers such as psoralen derivatives, azidophenacyl, proflavin, and azidoproflavin; artificial endonucleases; metal complexes. such as EDTA-Fe(II), o-phenanthroline-Cu(I), and porphyrin-Fe(II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid comprises an oligonucleotide conjugated to a carbohydrate, sulfated carbohydrate, or gylcan. Conjugates may be regarded as a way as to introduce a specificity into otherwise unspecific DNA binding molecules by covalently linking them to a selectively hybridizing oligonucleotide.

The binding domains of the catalytic nucleic acid may have one or more of their sugars modified or replaced so as to be ribose, glucose, sucrose, or galactose, or any other sugar. Alternatively, they may have one or more sugars substituted or modified in its 2' position, i.e. 2'allyl or 21-O-allyl. An example of a 2'-O-allyl sugar is a 2'-O-methylribonucleotide. Further, the nucleotides of the binding domain may have one or more of their sugars substituted or modified to form an a-anomeric sugar.

A catalytic nucleic acid binding domain may include non-nucleotide substitution. The non-nucleotide substitution includes either abasic nucleotide, polyether, polyamine, polyamide, peptide, carbohydrate, lipid or polyhydrocarbon compounds. The term "abasic" or "abasic nucleotide" as used herein encompasses sugar moieties lacking a base or having other chemical groups in place of base at the 1' position.

In one embodiment the nucleotides of the first binding domain comprise at least one modified internucleoside bond. In another embodiment the nucleotides of the second binding domain comprise at least one modified internucleoside bond. In a further embodiment the modified internucleoside bond is a phosphorothioate bond. The nucleic acid may comprise modified bonds. For example the bonds between nucleotides of the catalytic nucleic acid may comprise phosphorothioate linkages. The nucleic acid may comprise nucleotides having moiety may be modified by replacing one or both of the two bridging oxygen atoms of the linkage with analogues such as —NH, —CH$_2$, or —S. Other oxygen analogues known in the art may also be used. The phosphorothioate bonds may be stereo regular or stereo random.

In one embodiment the PAI-1-encoding mRNA encodes human PAI-1. In a further embodiment the human PAI-1-encoding mRNA has the sequence set forth in SEQ ID NO:5.

This invention provides a pharmaceutical composition comprising the instant catalytic nucleic acid and a pharmaceutically acceptable carrier. The following pharmaceutically acceptable carriers are set forth, in relation to their most commonly associated delivery systems, by way of example Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Examples of liposomes which can be used in this invention include the following: (1) CellFectin, 1:1.5 (M/M) liposome formulation of the cationic lipid N,NI,NII,NIII-tetramethyl-N,NI,NII,NIII-tetrapalmity-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-tri-methyl-ammoniumethyl sulfate) (Boehringer Manheim); and (4) Lipofectamine, 3:1 (M/M) liposome formulation of the polycationic lipid DOSPA and the neutral lipid DOPE (GIBCO BRL).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropyl-methylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc)

This invention provides a method of specifically inhibiting the expression of PAI-1 in a cell that would otherwise express PAI-1, comprising contacting the cell with the instant catalytic nucleic acid so as to specifically inhibit the expression of PAI-1 in the cell.

This invention provides a method of specifically inhibiting the expression of PAI-1 in a subject's cells comprising administering to the subject an amount of the instant catalytic nucleic acid effective to specifically inhibit the expression of PAI-1 in the subject's cells.

This invention provides a method of specifically inhibiting the expression of PAI-1 in a subject's cells comprising administering to the subject an amount of the instant pharmaceutical composition effective to specifically inhibit the expression of PAI-1 in the subject's cells.

This invention provides a method of treating a cardiovascular disease in a subject involving apoptosis of a cardiomyocyte in the subject which comprises administering to the subject an amount of the instant pharmaceutical composition effective to inhibit apoptosis of the cardiomyocyte in the subject so as to thereby treat the cardiovascular disease.

In one embodiment the cardiovascular disease is congestive heart failure. In another embodiment the cardiovascular disease is myocardial infarct. In another embodiment the cardiovascular disease is angina. In another embodiment the cardiovascular disease is myocardial ischemia. In another embodiment the cardiovascular disease is a cardiomyopathy.

This invention provides a method of treating a cardiovascular disease in a subject involving neointima formation in the subject which comprises administering to the subject an amount of the instant pharmaceutical composition effective to inhibit neointima formation in the subject so as to thereby treat the cardiovascular disease in the subject. The cardiovascular disease may be iatrogenic, the cardiovascular disease can be restenosis. In one embodiment the neotintima formation results from balloon angioplasty in the subject. In one embodiment the neotintima formation results from stent implantation in the subject.

This invention provides a method of treating a fibrotic disease in a subject involving fibrogenesis which comprises administering to the subject an amount of the instant pharmaceutical composition effective to inhibit fibrogenesis in the subject so as to thereby treat the fibrotic disease. In differing embodiments the fibrotic disease is a renal disease, a hepatic disease, a disease of the lung, a disease of the skin, or a disease of the eye. In further embodiments the fibrotic disease of the skin is scleroderma or psorasis.

An "effective amount" is an amount at least sufficient to treat, reduce, reverse or otherwise inhibit the given disease state. In the case of fibrotic diseases this means an amount sufficient to reduce, reverse or otherwise inhibit fibrogenesis. In the case of cardiovascular diseases this means an amount sufficient to reduce, reverse or otherwise inhibit cardiomyocyte apoptosis. In the case of neointima formation this means an amount sufficient to reduce, reverse or otherwise inhibit neointima formation.

Determining the effective amount of the instant pharmaceutical compositions can be done based on animal data using routine computational methods. In one embodiment, the effective amount contains between about 10 ng and about 100 µg of the instant nucleic acid molecules per kg body mass. In another embodiment, the effective amount contains between about 100 ng and about 10 µg of the nucleic acid molecules per kg body mass. In a further embodiment, the effective amount contains between about 1 µg and about 5 µg of the nucleic acid molecules per kg body mass. In another embodiment the effective amount contains. between about 10 µg and about 100 µg of the nucleic acid molecules per kg body mass. In a preferred embodiment the effective amount contains between about 100 µg and 500 µg of the nucleic acid molecules per kg body mass. In another embodiment the effective amount contains between about 500 µg and 1000 µg of the nucleic acid molecules per kg body mass. In another embodiment the effective amount contains between about 1 mg and 2 mg of the nucleic acid molecules per kg body mass.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

It is preferred to administer catalytic nucleic acids to mammals suffering from a cardiovascular disease or a fibrotic disease, in either native form or suspended in a carrier medium in amounts and upon treatment schedules which are effective to therapeutically treat the mammals to reduce the detrimental effects of cardiovascular disease or fibrotic disease. One or more different catalytic nucleic acids or antisense oligonucleotides or analogs thereof targeting different sections of the nucleic acid sequence of PAI-1-encoding mRNA may be administered together in a single dose or in different doses and at different amounts and times depending upon the desired therapy. The catalytic nucleic acids can be administered to mammals in a manner capable of getting the nucleic acids initially into the blood stream and subsequently into cells, or alternatively in a manner so as to directly introduce the catalytic nucleic acids into the cells or groups of cells, for example cardiomyocytes, by such means by electroporation or by direct injection into the heart or by catheter into renal tissue. It is within the scale of a person's skill in the art to determine optimum dosages and treatment schedules for such treatment regimens.

The effective amount of catalytic nucleic acid is administered to a human patient in need of inhibition of PAI-1 expression (or inhibition of fibrogenesis) from 1-8 or more times daily or every other day. Dosage is dependent on severity and responsiveness of the effects of the cardiovascular or fibrotic disease to be treated, with a course of treatment lasting from several days to months or until a cure is effected or a reduction of the effects is achieved. The actual effective amount, or dosage, administered may take into account the size and weight of the patient, whether the nature of the treatment is prophylactic, therapeutic in nature, the age, weight, health and sex of the patient, the route of administration, and other factors.

Pharmaceutical compositions may contain suitable excipients and auxiliaries which facilitate processing of the catalytic nucleic acids into preparations which can be used pharmaceutically. Preferably, the preparations, particularly those which can be administered orally and which can be used for the preferred type of administration, such as tablets, dragees, and capsules, and preparations which can be administered rectally, such as suppositories, as well as suitable solutions for administration parenterally or orally, and compositions which can be administered bucally or sublingually, including inclusion compounds, contain from about 0.1 to about 99 percent by weight of active ingredients, together with the excipient.

The pharmaceutical preparations of the present invention are manufactured in a manner which is itself well known in the art. For example, the pharmaceutical preparations may be made by means of conventional mixing, granulating, dragee-making, dissolving, or lyophilizing processes. The process to be used will depend ultimately on the physical properties of the active ingredient used.

Suitable excipients are, in particular, fillers such as sugars, for example, lactose or sucrose, mannitol or sorbitol, cellulose preparations and/or calcium phosphates, for example, tricalcium phosphate or calcium hydrogen phosphate as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl-starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate, and/or polyethylene glycol. Dragee cores may be provided with suitable coatings which, if desired, may be resistant to gastric juices. For this purpose, concentrated sugar solutions may be used, which may optionally contain gum arabic, talc, polyvinylpyrrolidone, polyethylene, glycol, and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethycellulose phthalate, are used. Dyestuffs and pigments may be added to the tablets of dragee coatings, for example, for identification or in order to characterize different combinations of active compound doses. Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with filters such as lactose, binders such as starches, and/or lubricants such as talc or magnesium stearate and optionally, stabilizers. In soft capsules, the active compounds are preferably dissolved or suspended in suitable liquids, such as fatty oils, liquid paraffin, or liquid polyethylene glycols. In additions, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, ethyl oleate or triglycerides. Aqueous injection suspensions may contain substances which increase the viscosity of the suspension including, for example, sodium carboxymethyl cellulose, sorbitol, and/or dextran. Optionally, the suspension may also contain stabilizers.

Additionally, catalytic nucleic acids of the present invention may also be administered encapsulated in liposomes or immunoliposomes, which are pharmaceutical compositions wherein the active -ingredient is contained either dispersed or variously present in corpuscles consisting of aqueous concentric layers adherent to lipidic layers. Liposomes are especially active in targeting the oligonucleotides to liver cells. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as dicetylphosphate, stearylamine, or phosphatidic acid, and/or other materials of a hydrophobic nature. The diameters of the liposomes generally range from about 15 nm to about 5 microns.

This invention also provides an oligonucleotide comprising consecutive nucleotides that hybridizes with a PAI-1-encoding mRNA under conditions of high stringency and is between 8 and 40 nucleotides in length. In different embodiments the oligonucleotide is between 40 and 80 nucleotides in length.

In a preferred embodiment the hybridization of antisense oligonucleotides with PAI-1-encoding mRNA interferes with one or more of the normal functions of PAI-1-encoding mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. For example, a human PAI-1 antisense oligonucleotide specifically hybridizes under given stringent conditions with targets on the human PAI-1 mRNA molecule and in doing so inhibits the translation thereof into PAI-1 protein.

The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. A PAI-1 antisense oligonucleotide specifically hybridizes under given stringent conditions with targets on the PAI-1-encoding mRNA molecule and in doing so inhibits the translation thereof into PAI-1.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, catalytic nucleic acids or antisense oligonucleotides may be formulated in accordance with this invention which are targeted wholly or in part to these associated ribonucleotides as well as to the informational ribonucleotides. For example, the antisense oligonucleotides may therefore be specifically hybridizable with a transcription initiation site region, a translation initiation codon region, a 5' cap region, an intron/exon junction, coding sequences, a translation termination codon region or sequences in the 5'- or 3'-untranslated region. Similarly, the catalytic nucleic acids may specifically cleave a transcription initiation site region, a translation initiation codon region, a 5' cap region, an intron/exon junction, coding sequences, a translation termination codon region or sequences in the 5'- or 3'-untranslated region. As is known in the art, the translation initiation codon is typically 5'-AUG (in transcribed mRNA molecules; 5'-ATG in the corresponding DNA molecule). A minority of genes have a translation initiation codon having the RNA sequence 5'-GUG, 5'UUG or 5'-CUG, and 5'-AUA, 5'-ACG and 5'-CUG have been shown to function in vivo. Thus, the term "translation initiation codon" can encompass many codon sequences, even though the initiator amino acid in each instance is typically methionine in eukaryotes. It is also known in the art that eukaryotic genes may have two or more alternative translation initiation codons, any one of which may be preferentially utilized for translation initiation in a particular cell type or tissue, or under a particular set of conditions. In the context of the invention, "translation initiation codon" refers to the codon or codons that are used in vivo to initiate translation of an. mRNA molecule transcribed from a gene encoding PAI-1, regardless of the sequence(s) of such codons. It is also. known in the art that a translation termination codon of a gene may have one of three sequences, i.e., 5'-UAA, 5'-UAG and 5'-UGA (the corresponding DNA sequences are 5'-TAA, 5'-TAG and 5'-TGA, respectively). The term "translation initiation codon region" refers to a portion of such an mRNA or gene that encompasses from about 25 to about 50 contiguous nucleotides in either direction (i.e., 5' or 3') from a translation initiation codon. This region is one preferred target region. Similarly, the term "translation termination codon region" refers to a portion of such an mRNA or gene that encompasses from about 25 to about 50 contiguous nucleotides in either direction (i.e., 5' or 3') from a translation termination codon. This region is also one preferred target region. The open reading frame or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions may also be preferred targets.

Once the target site or sites have been identified, antisense oligonucleotides can be chosen which are sufficiently complementary to the target, i.e., hybridize sufficiently well and with sufficient specificity, to give the desired disruption of the function of the molecule. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the antisense oligonucleotide. Similarly, catalytic nucleic acids are synthesized once cleavage target sites on the PAI-1 mRNA molecule have been identified, e.g. any purine:pyrimidine consensus sequences in the case of DNA enzymes. Catalytic nucleic acids and antisense oligonucleotides targeted to disrupting polymorphisms and mutants of the PAI-1 maybe similarly made as described above based on the polymorphic or mutant PAI-1 mRNA sequence.

Methods for selecting which particular antisense oligonucleotides sequences directed towards a particular protein-encoding mRNA are that will-form the most stable DNA: RNA hybrids within the given target mRNA sequence are known in the art and are exemplified in U.S. Pat. No. 6,183,966 which is herein incorporated by reference.

In one embodiment at least one internucleoside linkage within the instant oligonucleotide comprises a phosphorothioate linkage. Antisense oligonucleotide molecules synthesized with a phosphorothioate backbone have proven particularly resistant to exonuclease damage compared to standard deoxyribonucleic acids, and so they are used in preference. A phosphorbthioate antisense oligonucleotide for PAI-1 mRNA can be synthesized on an Applied Biosystems (Foster City, Calif.) model 380B DNA synthesizer by standard methods. For example, sulfurization can be performed using tetraethylthiuram disulfide/acetonitrile. Following cleavage from controlled pore glass support, oligodeoxy-nucleotides can be base deblocked in ammonium hydroxide at 60° C. for 8 h and purified by reversed-phase HPLC [0.1M triethylammonium bicarbonate/acetonitrile; PRP-1 support]. Oligomers can be detritylated in 3% acetic acid and precipitated with, 2% lithiumperchlorate/acetone, dissolved in sterile water and reprecipitated as the sodium salt from 1 M NaCl/ethanol. Concentrations of the full length species can be determined by UV spectroscopy. Any other means for such synthesis known in the art may additionally or alternatively Ibe employed. It is well known to use similar techniques., to prepare oligonucleotides such as the phosphorothioates and alkylated derivatives.

Preferred modified oligonucleotide backbones include, for example, phosphorothioates, chiral phosphorothioates, phosphorodithioates., phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphos-phoramidates, thionophosphoramidates, thionoalkylphos-phonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3-' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,8211; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In one embodiment the nucleotides of the instant oligo-nucleoptide comprise at least one deoxyribonucleotide. In another embodiment the nucleotides comprise at least one ribonucleotide. Such deoxyribonucleotides or ribonucle-otides can be modified or derivatized as described hereinabove.

In one embodiment the PAI-1-encoding mRNA encodes human PAI-1. In a further embodiment the human PAI-1-encoding mRNA comprises consecutive nucleotides, the sequence of which is set forth in SEQ ID NO:5.

This invention further provides a method of treating a subject which comprises administering to the subject an amount of the instant oligonucleotide effective to inhibit expression of a PAI-1 in the subject so as to thereby treat the subject.

This invention further provides a method of treating a cardiovascular disease in a subject involving apoptosis of a cardiomyocyte in the subject which comprises administering to the subject an amount of the instant oligonucleotide effective to inhibit apoptosis of the cardiomyocyte in the subject so as to thereby treat the cardiovascular disease.

This invention further provides a method of treating a fibrotic disease in a subject involving fibrogenesis in the subject which comprises administering to the subject an amount of the instant oligonucleotide effective to inhibit fibrogenesis in the subject so as to thereby treat the fibrotic disease.

This invention further provides a method of treating a cardiovascular disease in a subject involving neointima formation in the subject which comprises administering to the subject an amount of the instant pharmaceutical composition effective to inhibit neointima formation in the subject so as to thereby treat the cardiovascular disease in the subject. The cardiovascular disease may be iatrogenic, the cardiovascular disease can be restenosis. In one embodiment the neotintima formation results from balloon angioplasty in the subject. In one embodiment the neotintima formation results from stent implantation in the subject.

Antisense oligonucleotides can be administered by intravenous injection, intravenous drip, subcutaneous, intraperitoneal or intramuscular injection, orally or rectally. Human pharmacokinetics of certain antisense oligonucleotides have been studied. See (37) incorporated by reference in its entirety.

This invention further provides a method of treating a vascular disease in a subject wherein the disease is treated by reducing thrombin or fibrin production which comprises administering an inhibitor of PAI-1 expression effective to inhibit PAI-1 expression and thereby by reduce thrombin or fibrin production so as to thereby treat the vascular disease in the subject.

This invention further provides a method of treating a vascular disease in a subject wherein the vascular disease is treated by inhibition of PAI-1 expression comprising administering to the subject an inhibitor of PAI-1 expression effective to inhibit PAI-1 expression in the subject and thereby treat the vascular disease in the subject.

This invention further provides a method of treating a hepatic disease in a subject wherein the hepatic disease is treated by inhibition of PAI-1 expression comprising administering to the subject an inhibitor of PAI-1 expression effective to inhibit PAI-1 expression in the subject and thereby treat the hepatic disease in the subject. In one embodiment the disease is acute fulminant hepatic failure. In one embodiment the inhibition of PAI-1 expression enhances hepatoctye regeneration after injury such as from toxic shock or viral hepatitis.

This invention provides the instant methods wherein the inhibitor of PAI-1 expression is an antisense. oligonucleotide, an antibody, a catalytic nucleic acid, a. small molecule, or RNAi. This invention provides the instant methods, wherein the disease is an ischemic disease. In different embodiments the disease is peripheral arterial disease or cerebrovascular disease.

This invention further provides a method of inducing neovascularization in a heart tissue of a subject comprising administering an amount of an inhibitor of PAI-1 expression to the subject effective to inhibit expression of PAI-1 in the heart and thereby induce neovascularization in the heart tissue of the subject. In one embodiment the subject is suffering from a cardiovascular disease. In further embodiments the disease is myocardial infarction, angina, congestive heart failure, peripheral arterial disease, or myocardial hypoxia.

This invention further provides a method of inducing neovascularization in a tissue of a subject comprising administering an amount of an inhibitor of PAI-1 expression to the subject effective to inhibit expression of PAI-1 in the tissue of the subject and thereby induce neovascularization in the tissue of the subject. In one embodiment the subject is suffering from an ischemic disease. In further embodiments the disease is ischemic renal disease, cerebrovascular disease, stroke, or a hepatic disease.

This invention further provides a pharmaceutical composition comprising an inhibitor of PAI-1 expression and a pharmaceutically acceptable carrier. In different embodiments the inhibitor of PAI-1 expression is a catalytic nucleic acid, an oligonucleotide, a monoclonal antibody, a small molecule, or RNAi, (RNA interference—as detailed in U.S. Pat. No. 6,506,599, the contents of which are hereby incorporated by reference).

This invention further provides a method of treating a cardiovascular disease in a subject wherein the disease is treated by improving myocardial function in the subject, comprising administering to the subject an amount of the instant pharmaceutical composition effective to inhibit improve myocardial function and thereby treat the cardiovascular disease in the subject. In one embodiment the instant method further comprises administering an agent to the subject prior to, concomitant with or subsequent to administering the pharmaceutical composition. In further embodiments the agent is endothelial progenitor cells, bone marrow cells, cardiac progenitor cells, embryonic stem cells, or cord blood stem cells. In other embodiments the agent is G-CSF, GM-CSF, SDF-1, IL-8, SCF, VEGF, FGF, or a GRO family chemokine.

This invention further provides a method of inhibiting. smooth muscle cell proliferation in a heart of a subject comprising administering to the subject an amount of the instant pharmaceutical composition effective to inhibit smooth muscle cell proliferation in the heart of the. subject.

This invention further provides a method of inhibiting thrombin and fibrin deposition in a heart of a subject comprising administering to the subject an amount of the instant pharmaceutical composition to the subject effective to inhibit thrombin and fibrin deposition in the heart of the subject.

This invention further provides the instant methods further comprising administering to the subject endothelial progenitor cells, bone marrow cells, cardiac progenitor cells, embryonic, stem cells, or cord blood stem cells. This invention further provides the instant methods wherein the pharmaceutical composition is administered through a stent, a scaffold, intravenously, orally, by inhalation, subcutaneously, by direct muscular injection, or via a gene vector.

This invention further provides a method of inhibiting thrombin and fibrin deposition in a tissue of a subject comprising administering to the subject an amount of the instant pharmaceutical composition effective to inhibit thrombin and fibrin deposition in the tissue of the subject.

This invention further provides the instant method, wherein the subject is suffering from deep vein thrombosis-,.. pulmonary embolism, renal disease, coronary infarction, metastasis, inflammation, disseminated intravascular coagulation, atherosclerosis, rheumatoid arthritis, glomerulonephritis, systemic lupus erythematosus, autoimmune neuropathy, granulomatous disease, or allograft rejection.

This invention further provides a method of treating septic shock in a subject comprising administering an amount of the instant pharmaceutical composition to the subject effective to treat the septic shock in the subject.

This invention further provides a method of treating a subject suffering from a thrombotic disease, thrombotic disorder or haemostatic disorder wherein the disease or disorder is associated with elevated expression of PAI-1, comprising administering to the subject an amount of the instant pharmaceutical composition effective to reduce the PAI-1 expression in the subject and thereby treat the disease.

This invention further provides the instant method, wherein the disease or disorder is deep vein thrombosis, pulmonary embolism, renal disease, coronary infarction, metastasis, inflammation, disseminated intravascular coagulation, atherosclerosis, rheumatoid arthritis, glomerulonephritis, systemic lupus erythematosus, autoimmune neuropathies, granulomatous disease, or allograft rejection. In one embodiment, the instant method further comprises administering to the subject a thrombolytic agent, or an activator of a thrombolytic agent. In differing embodiments the activator of the thrombolytic agent is tissue plasminogen activator, urokinase, streptokinase, or prourokinase.

In one embodiment of the instant method, the method further comprises administering to the subject an anticoagulant. In differing embodiments the anticoagulant is heparin, warfarin, aspirin, anisindione, phenindone, or hydroxy coumarin.

This invention further provides a method of making the instant pharmaceutical compositions comprising admixing a therapeutically effective amount of an inhibitor of PAI-1 expression and a pharmaceutically acceptable carrier.

This invention provides all of the instant methods wherein the subject is a mammal. In a preferred embodiment the mammal is a human being.

In this invention, the various embodiments of subjects, pharmaceutically acceptable carriers, dosage, cell types, routes of administration and target nucleic acid sequences are envisioned for each of the instant nucleic acid molecules, oligonucleotides, inhibitors of PAI-1 expression, small molecules, pharmaceutical compositions, and methods.

This invention will be better understood by reference to the Experimental Details which follow, but those skilled in the art will readily appreciate that the specific experiments detailed are only illustrative of the invention as described more fully in the claims which follow thereafter.

Experimental Results

Construction of DNA Enzymes Targeting Human and Rat PAI-1 mRNA.

We designed three DNA enzymes to specifically target pyrimidine-purine junctions at or near the translational start site AUG of human and rat PAI-1 messenger RNA, a region that is conserved between species and has low relative free energy (17). As shown in FIG. 1a, the three DNA enzymes, termed E1 (SEQ ID NO:2), E2 (SEQ ID NO:4), and E3 (SEQ ID NO:3), contained identical 15-nucleotide catalytic domains (SEQ ID NO:1) which were flanked by two arms of eight nucleotides (E1, E2) or nine nucleotides (E3) with complementarity to human (E1, E3) or rat (E2) PAI-1 mRNA. To produce the control DNA enzyme E0 (SEQ ID NO:7), the nucleotide sequence in the two flanking arms of E2 was scrambled without altering the catalytic domain (FIG. 1a). The 3' terminus of each molecule was capped with an inverted 3'-3'-linked thymidine for resistance to 3'-to-5' exonuclease digestion.

Specific Cleavage of Human PAI-1 mRNA by E1 and E3 DNA Enzymes.

Figure 1B:
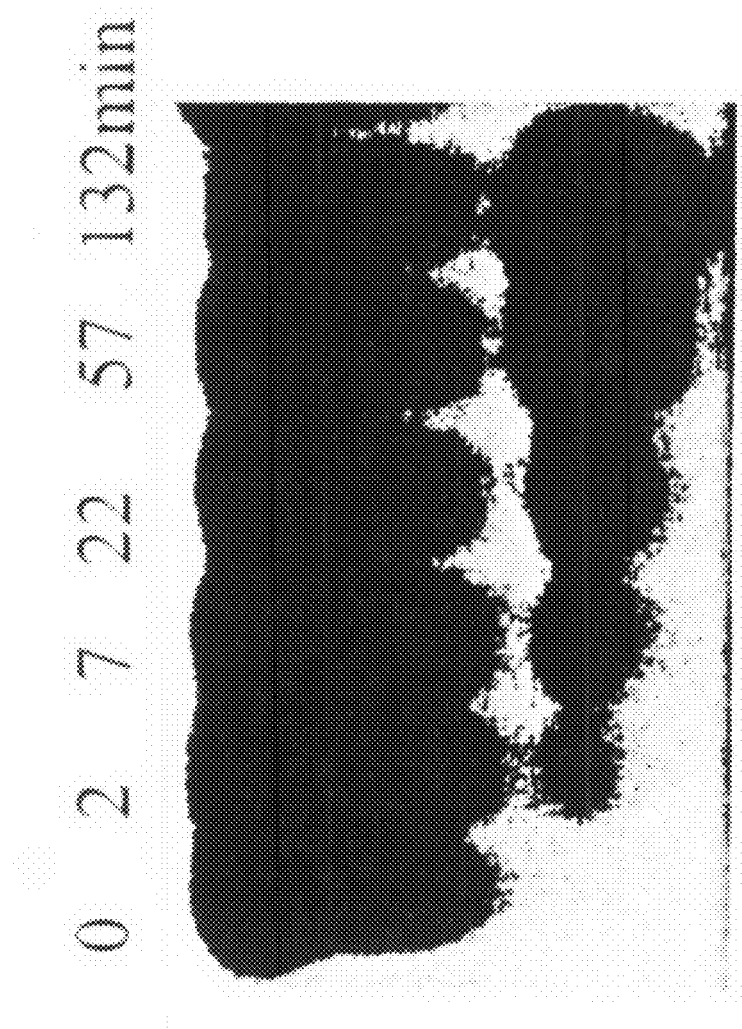
Figure 1C:
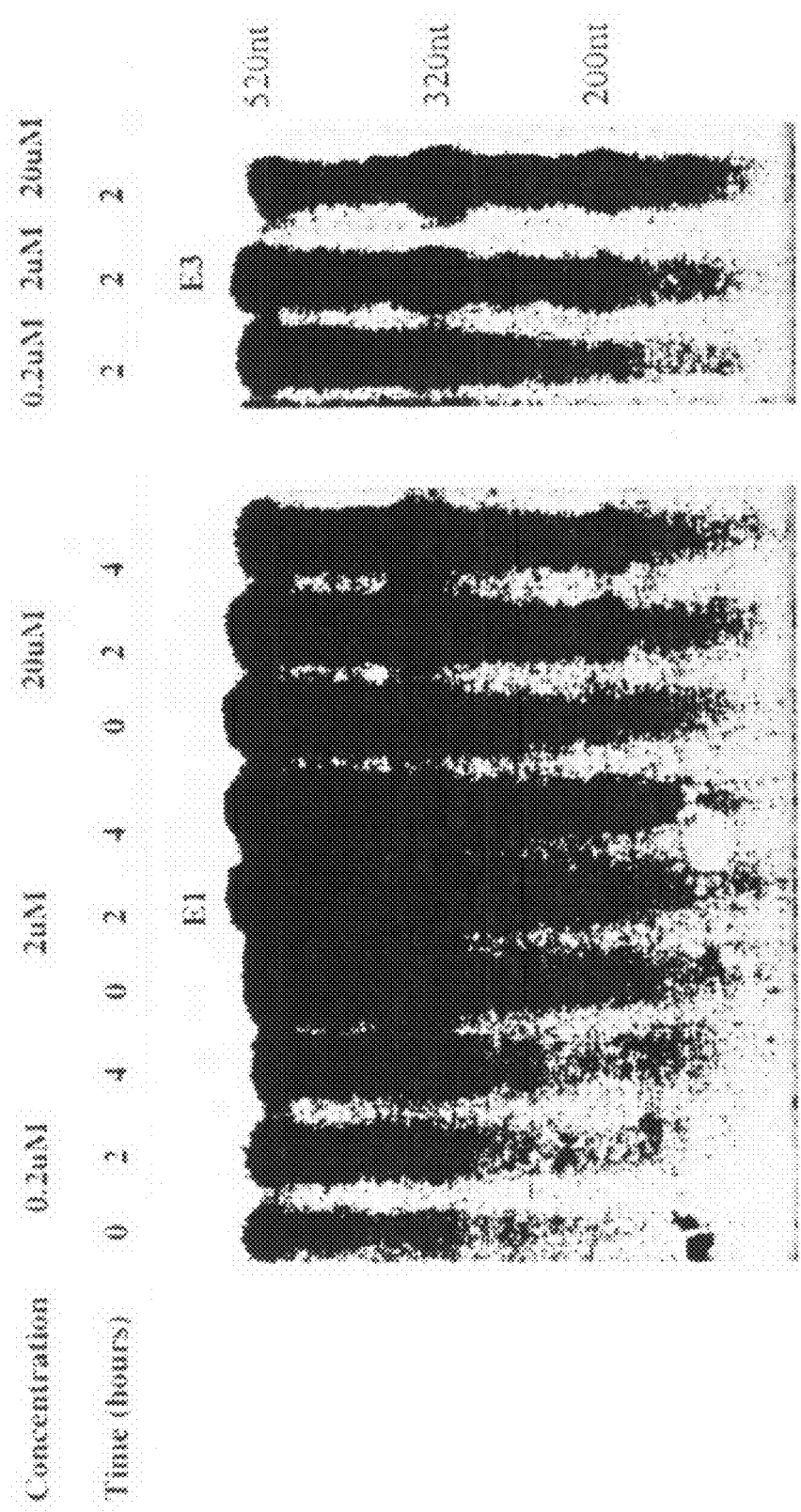
Figure 1B:
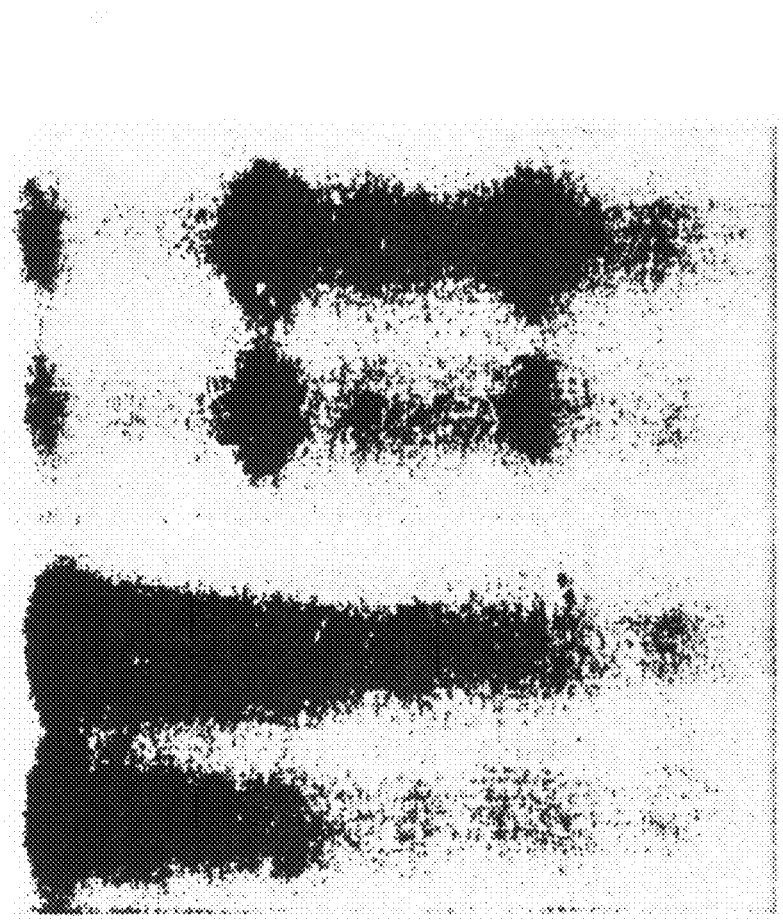

As shown in FIG. 1b, the 2'-base oligonucleotide S1 (SEQ ID NO:8), synthesized from human PAI-1 mRNA and labeled at the 5' end with 32P, was cleaved within 2 minutes when cultured with E1 at 10:1 substrate:enzyme excess, with maximal cleavage occurring by 2 hours. The 10-nucleotide cleavage product is consistent with the size of the 32P-labeled fragment at the 5' end. E1 also cleaved larger 32P-labeled fragments of human PAI-1 mRNA, prepared by in vitro transcription, in a time- and concentration-dependent manner, FIG. 1c. A 520 nucleotide transcript was maximally cleaved by 2-4 hours to expected cleavage products of 320 and 200 nucleotides. A similar dose-dependency was seen with E3, with maximal cleavage of human PAI-1 mRNA transcripts occurring at the highest concentration used, 20 AM. The sequence-specific nature of the DNA enzymatic cleavage is shown in FIG. 1d, where the control DNA enzyme E0, containing an identical catalytic domain to E1 and E3, but scrambled sequences in the flanking arms, caused no cleavage of human PAI-1 mRNA transcripts. Pre-heating the transcript to 72° C. for 10 minutes prior to incubation with E1, but not E0, further increased cleavage.

Specific Cleavage of Rat PAI-1 mRNA by E2 DNA Enzyme.

Figure 2A:
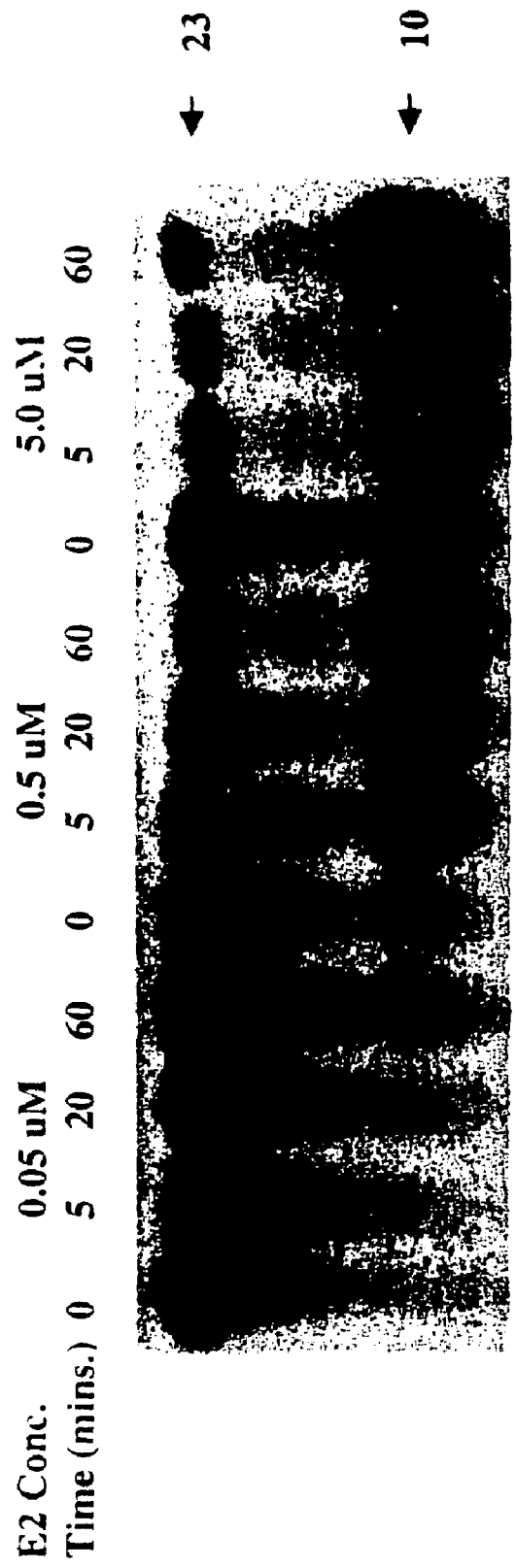
Figure 2B:
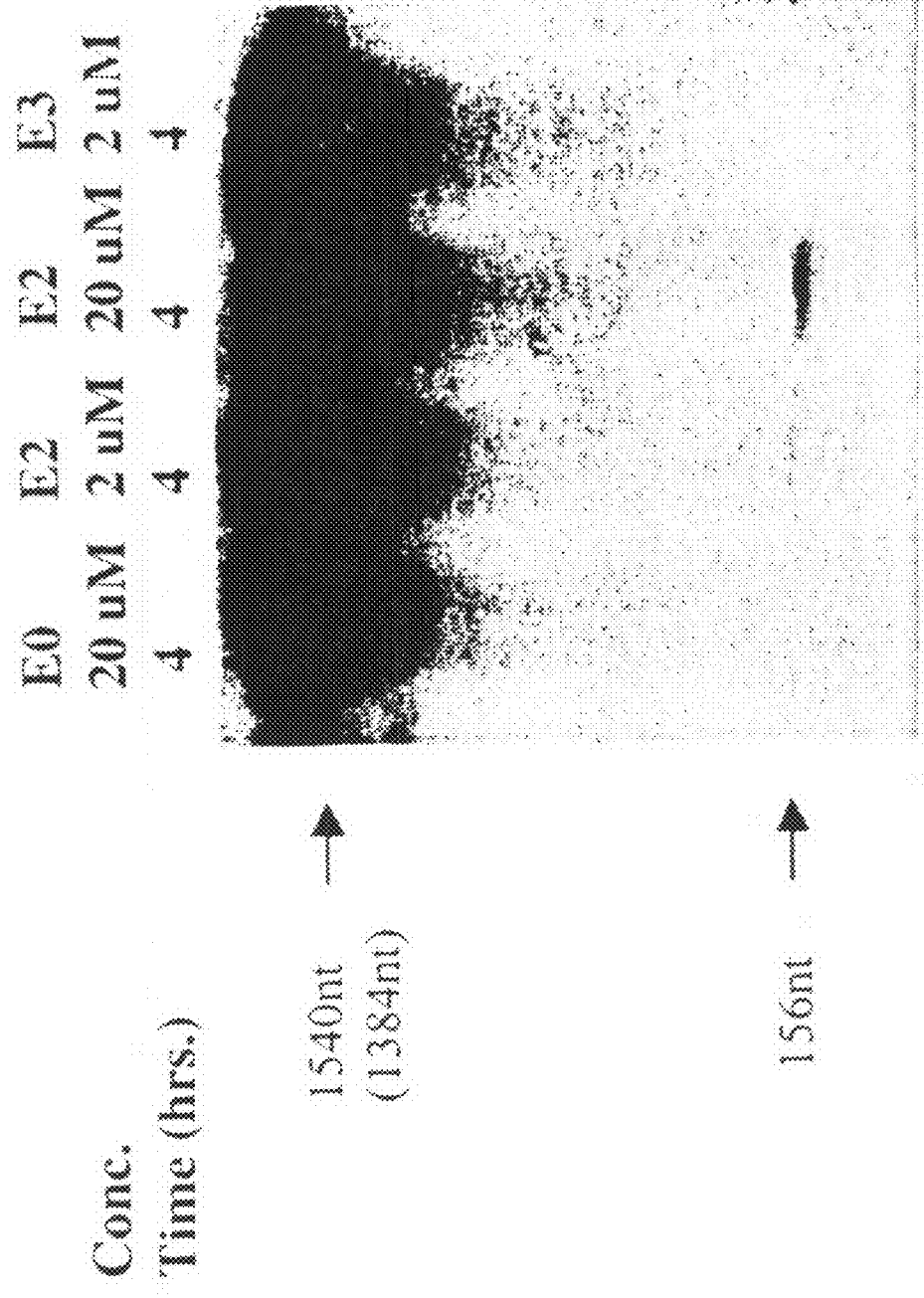

Further evidence for the specificity of the DNA enzymatic reactions can be seen in FIG. 2. The DNA enzyme E2 cleaved the 23-base oligonucleotide S2, synthesized from the sequence of rat PAI-1 mRNA, in a dose- and time-dependent manner, FIG. 2a. E2 also cleaved a rat PAI-1 mRNA transcript in a dose-dependent manner by 2-4 hours to give the 156 nucleotide cleavage product, FIG. 2b. In contrast, neither the scrambled control DNA enzyme E0 nor E3 cleaved the rat PAI-1 mRNA transcript. Since the rat PAI-1 mRNA transcript (SEQ ID NO:10) differs by only one nucleotide from the human mRNA PAI-1 transcript (SEQ ID NO:9) which can be cleaved by E3, FIG. 2c, these results demonstrate the exquisite target specificity of these DNA enzymes.

DNA Enzymes Inhibit Induction of Endogenous PAI-1 mRNA and Protein.

Figure 3A:
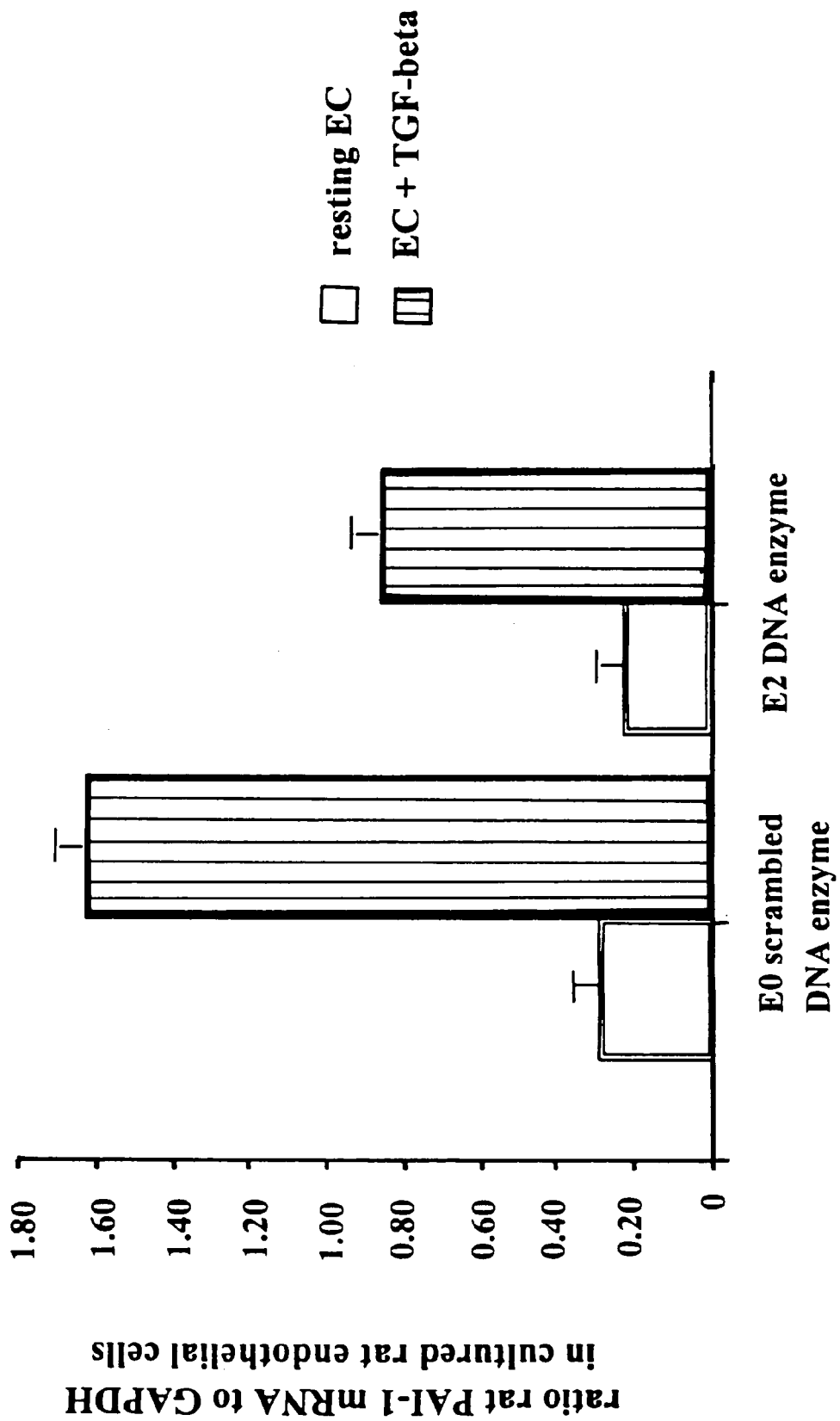
FIGS. 3 (A)-(D) (A) This figure shows Densitometric analysis of RT-PCR products following reverse transcription of cellular mRNA: E2 inhibited TGF-beta inducible steady-state mRNA levels in cultured rat endothelium by 52% relative to the E0 scrambled DNA.
Figure 3B:
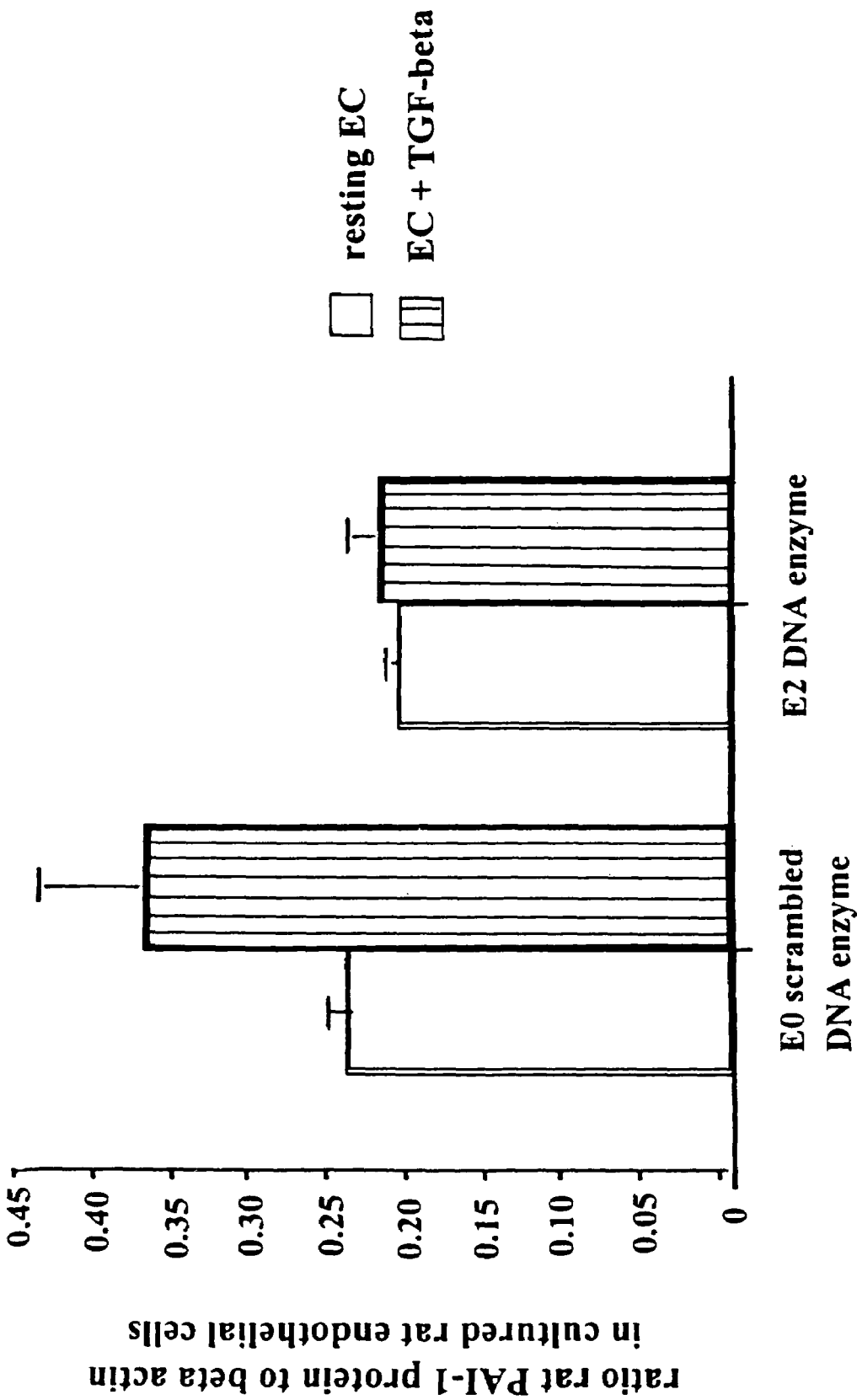

To determine the effect of DNA enzymes on endogenous PAI-1 production, endothelial monolayers of human and rat origin were grown to confluence and transfected with species-specific DNA enzymes or scrambled control. Transfected cells were then activated with TGF-beta for 8 hours to maximally induce expression of PAI-1. Densitometric analysis of RT-PCR products following reverse transcription of cellular mRNA showed that E2 inhibited TGF-beta inducible steady-state mRNA levels in cultured rat endothelium by 52%, FIG. 3a, relative to the E0 scrambled DNA. Constitutive PAI-1 mRNA levels were not affected by transfection with the DNA enzymes. FIG. 3b shows the effect of endothelial cell transfection with E2 DNA enzyme on TGF-beta mediated induction of PAI-1 proteins Endothelial cells transfected with scrambled DNA enzyme demonstrated approximately 50% increase in cytoplasmic PAI-1 protein as detected by Westefrn blot. In contrast, this effect was almost completely abrogated by transfection with the PAI-1 DNA enzyme E2.

Resistance of DNA Enzymes to Serum-dependent Degradation.

Figure 3C:
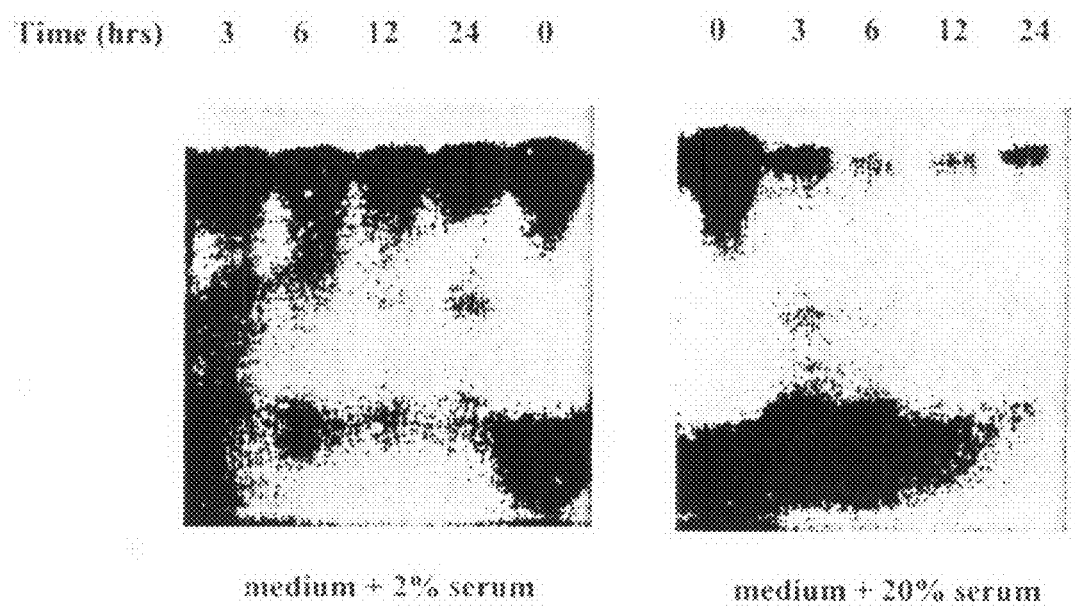
Figure 3D:
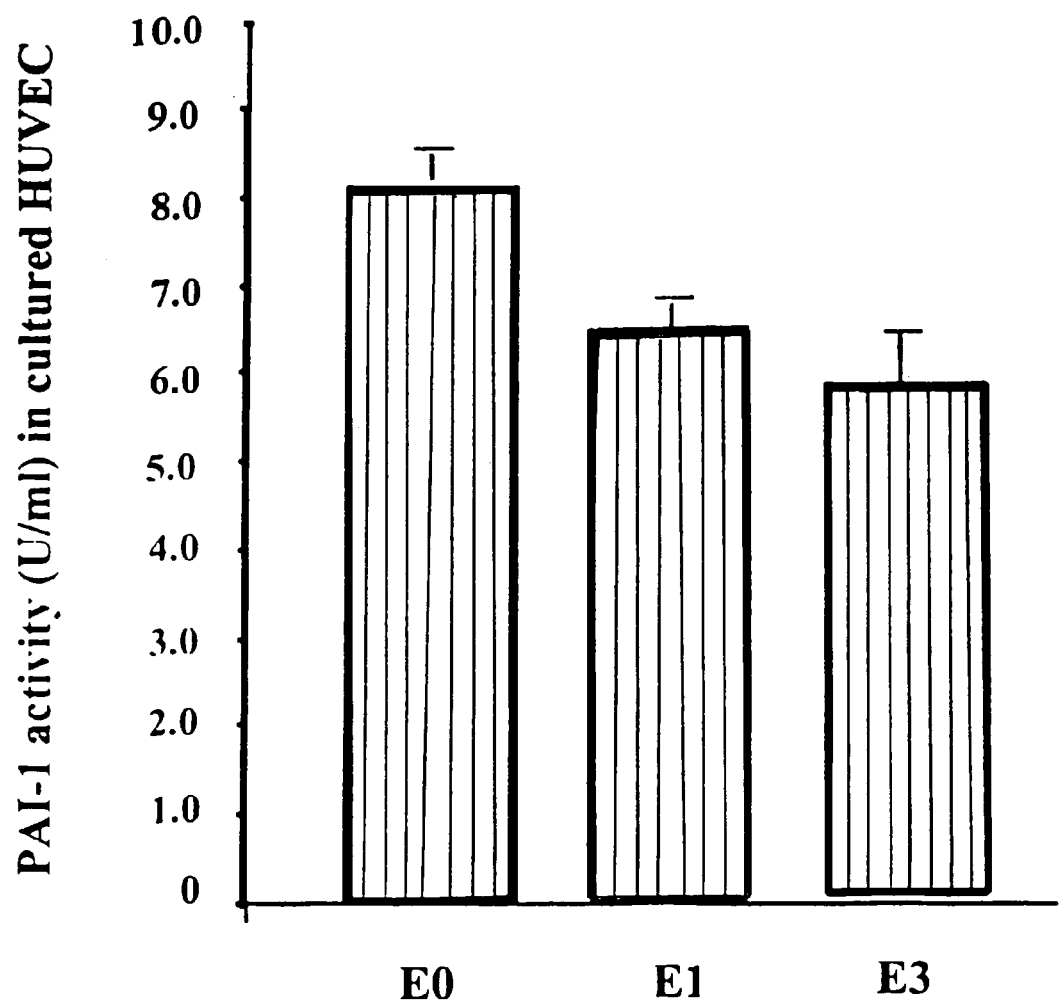

Since DNA enzymes with a thymidine in the correct orientation-at the 3' end are significantly degraded by factors in serum (1-5% concentration) within 24 hours (14), we investigated the protective effect of an inverted thymidine at the 3' end on serum-dependent nucleolytic degradation of PAI-1 DNA enzymes. The DNA enzyme E1 was labeled with 32P and incubated for 3-24 hours with human umbilical vein endothelial cell (HUVEC) monolayers cultured in medium containing physiologic (2%) or supraphysiologic (20%) serum concentrations As shown in FIG. 3c, whereas the DNA enzyme was almost completely degraded within 6 hours of cell culture in medium containing 20% serum, it remained intact during the entire 24 hours of cell culture with medium containing 2% serum. As shown in FIG. 3d, HUVEC transfected with E1 or E3 DNA enzymes and cultured for 12 hours in 2% serum demonstrated 20% and 28% reduction in TGF-beta dependent PAI-1 activity compared With transfection with the scrambled DNA E0 (both p<0.01) Together, these results indicate that an inverted thymidine at the 3' end can protect the PAI-1 DNA enzyme against nucleolytic degradation at physiologic serum concentrations likely to be encountered in vivo, consequently enabling inhibition of cellular PAI-1 activity.

Intracardiac Injection of E2 Reduces Macrophage PAI-1 Expression.

We investigated whether intracardiac injection of E2 at the time of myocardial infarction could inhibit PAI-1 expression in the rat heart. At two weeks after ligation of the left anterior descending (LAD) artery and induction of myocardial infarction, immunohistochemical studies showed that PAI-1 expression occurred predominantly in CD68-positive rat macrophages within the infarct zone and at the peri-infarct region. While a few vascular endothelial cells stained positively, PAI-1 expression was not detected within myocytes or interstitial cells distally to the infarct. We conclude that the principal source of PAI-1 protein in the infarcted rat heart is due to production by infiltrating macrophages and phagocytes. At two weeks after injection with E2, PAI-1 expression in infarcted rat hearts was dramatically altered, with 71% reduction in PAI-1 expression by macrophages at the peri-infarct region (p<0.01), FIG. 4a. Inhibition of PAI-1 expression at this site was highly specific since PAI-1 expression within macrophages in the center of the infarct zone remained unaffected after E2 injection, and injection with the scrambled DNA enzyme E0 did not reduce peri-infarct PAI-1 expression.

Intracardiac Injection of E2 Results in Peri-infarct Neovascularization.

By two weeks, in parallel with reduction in PAI-1 expression, hearts from rats injected with E2 demonstrated significantly increased numbers of large-lumen capillaries (>6 nuclei) at the peri-infarct region, FIG. 4b. While injection of E2 alone caused a significant increase in large-lumen capillaries at the peri-infarct region compared with injection of the E0 scrambled DNA enzyme, even more striking was the additional 62% increase in the number of large-lumen capillaries when E2 was co-administered together with intravenously delivered human adult bone marrow-derived CD34+ CD117$^{bright}$ angioblasts. While many of the newly-formed vessels were of rat origin (angiogenesis), a significant number were of human origin (vasculogenesis) as defined by a human anti-CD31 mAb. In the presence of E2 the number of unincorporated, discrete, interstitial human angioblasts in the infarct zone and peri-infarct region was reduced by 5.2-fold compared with E0 control enzyme, FIG. 4c. conversely, the number of large-lumen capillaries (>6 nuclei) at the peri-infarct region was increased by 14-fold following E2 injection as compared with E0. We conclude that by inhibiting PAI-1 expression at the peri-inffarct region E2 enables human angioblasts to more effectively migrate through cardiac tissue, coalesce and participate.in new vessel formation.

E2 Protects Cardiomyocytes at the Peri-infarct Region Against Apoptosis.

We have previously shown that neovascularization at the peri-infarct region, induced by bone marrow-derived endothelial progenitors, can protect adjacent viable cardiomyocytes against apoptosis. Since intracardiac injection of E2 alone induced neovascularization at this site in infarcted rat hearts, we examined the effect of E2 injection on cardiomyocyte apoptosis. Injection with E2 at the time of LAD ligation resulted in 70% reduction in apoptosis of cardiomyocytes at the peri-infarct region (p<0.01), FIG. 5a. This was not observed with injection of the scrambled control DNA enzyme E0. The level in protection against cardiomyocyte apoptosis was similar to the level observed with intravenous infusion of human angioblasts.

Renal Fibrosis.

The renin-angiotensin system (RAS) in progressive renal disease has been extensively investigated, indicating multiple actions beyond hemodynamic and salt/water homeostasis. The RAS is now recognized to be linked to induction of plasminogen activator inhibitor-1 (PAI-1) likely via both the type 1 (AT1) and type 4 (AT4) receptors, thus, promoting both thrombosis and fibrosis (39). Plasminogen activator inhibitor type 1 is thus a suitable target in renal fibrogenesis. The progression of renal lesions to fibrosis involves several mechanisms, among which the inhibition of extracellular matrix (ECM) degradation appears to play an important role two interrelated proteolytic systems are involved in matrix degradation: the plasminogen activation system and the matrix metalloproteinase system. PAI-1 as the main inhibitor of plasminogen activation, regulates fibrinolysis and the plasmin-mediated matrix metalloproteinase activation. PAI-1 is also a component of the ECM, where it binds to vitronectin. PAI-1 is not expressed in the normal human kidney but is strongly induced in various forms of kidney diseases, leading to renal fibrosis and terminal renal failure. Thrombin, angiotensin II, and transforming growth factor-beta are potent in vitro and in vivo agonists in increasing PAI-1 synthesis. Several experimental and clinical studies support a role for PAI-1 in the renal fibrogenic process occurring in chronic glomerulonephritis, diabetic nephropathy, focal segmental glomerulosclerosis, and other fibrotic renal diseases (40).

End-stage renal disease (ESRD) comprises an enormous public health burden, with an incidence and prevalence that are increasingly on the rise. This escalating prevalence suggests that newer therapeutic interventions and strategies are needed to complement current therapeutic approaches. Although much evidence demonstrates conclusively that angiotensin II mediates progressive renal disease, recent evidence also implicates aldosterone as an important pathogenetic factor in progressive renal disease. Recently, several lines of experimental evidence demonstrate that selective blockade of aldosterone, independent of renin-angiotensin blockade, reduces proteinuria and nephrosclerosis in the spontaneously hypertensive stroke-prone rat (SHRSP) model and reduces proteinuria and glomerulosclerosis in the subtotally nephrectomized rat model (ie, remnant kidney). Whereas pharmacologic blockade with angiotensin II receptor blockers and angiotensin-converting enzyme (ACE) inhibitors reduces proteinuria and nephrosclerosis/glomerulosclerosis, selective reinfusion of aldosterone restores these abnormalities despite continued renin-angiotensin blockade. Aldosterone may promote fibrosis by several mechanisms, including plasminogen activator inhibitor-1 (PAI-1) expression and consequent alterations of vascular ribrinolysis, by stimulation of transforming growth factor-beta1 (TGF-beta1), and by stimulation of reactive oxygen species (ROS) (41). Therefore it is expected that PAI-1 is a suitable target for therapeutic intervention into renal fibrosis.

Progressive renal disease is characterized by the induction of plasminogen activator inhibitor-1 (PAI-1), suggesting that impaired activity of the renal plasmin cascade may play a role in renal fibrosis. Studies with PAI-1 knock-out mice showing resistance to fibrotic effects of ureteric obstruction establish an important fibrogenic role for PAI-1 in the renal fibrogenic response. The results demonstrate that one important fibrosis-promoting function of PAI-1 is its role in the recruitment of fibrosis-inducing cells, including myofibroblasts and macrophages (42)

Liver Fibrosis.

During chronic liver injury, transforming growth factor beta (TGF-beta) plays a prominent role in stimulating liver fibrogenesis by myofibroblast-like cells derived from hepatic stellate cells (HSCs). In acute liver injury, HSC-derived TGF-beta increased plasminogen activator inhibitor type 1 (PAI-1) and alpha2(I) procollagen (COL1A2) transcripts. Smad 2 in HSCs during liver injury and primary cultured HSCs were activated by an autocrine mechanism, because high levels of Smad 2 phosphorylation and induction of PAI-1 transcript by TGF-beta were observed in HSCs (43).

Increased PAI-1 together with uPA, uPAR and tPA are associated with overall inhibition of matrix degradation in cirrhotic liver. Hepatic stellate cells are an important source of PAI-1 during liver fibrosis. Increased expression of plasminogen activator and plasminogen activator inhibitor during liver fibrogenesis of rats: role of stellate cells (44). Therefore it is expected that PAI-1 is a suitable target for therapeutic intervention into hepatic fibrosis.

Lung Fibrosis:

PAI-1 levels in bronchoalveolar lavage (BAL) supernatant fluids are significantly higher in idiopathic pulmonary fibrosis (IPF) patients than in normal subjects. Increased procoagulant and antifibrinolytic activities in the lungs with idiopathic pulmonary fibrosis. Therefore it is expected that PAI-1 is a suitable target for therapeutic intervention into fibrosis of the lung.

In addition, cataracts of the eye may be treated by reversing the symptomatic fibrosis that occurs, thought to be due to ischemia, by the mechanism-described hereinabove.

Restenosis:

PAI-1 levels are greatly elevated in patients with myocardial infarction, especially in diabetics, peripheral arterial disease, especially in diabetics, and in balloon angioplasty and/or stent implantation and restenosis. The elevated pai-1 levels reduce levels of activated protein c, and this results in increased thrombin generation, fibrin and clot formation. The thrombin induces smooth muscle cell migration and proliferation, which are the hallmarks of restenosis after balloon angioplasty or stent implantation!

We therefore theorized that local administration of a PAI-1 DNA enzyme at site of balloon angioplasty would increase endogenous activated protein C, reduce thrombin generation, decrease fibrin deposition, decrease smooth muscle cell migration and proliferation, and prevent restenosis after balloon angioplasty or stent implantation.

We first measured neointima formation 14 days after balloon; angioplasty was performed in conjunction with intra-carotid PAI-1 DNA enzyme, scrambled DNA enzyme or saline instillation. As shown in FIGS. 13 and 14, PAI-1 DNA enzyme significantly inhibited neointima formation, as defined by planimetry and by proportion of vessel lumen encroached. Animals receiving local instillation of the PAI-1 DNA enzyme demonstrated over 50% reduction in neointima formation relative to those receiving either scrambled DNA enzyme or saline (both $p<0.05$). Balloon angioplasty-treated animals receiving saline had mean carotid lumen areas at 14 days of $0.178+/-0.067$ $\mu m^2$ and mean intimal arease of $0.281+/-0.082$ $\mu m^2$, those receiving scrambled DNAzyme had mean lumen areas of $0.129+/-0.051$ $\mu m^2$ and mean intimal areas of $0.247+/-0.058$ $\mu m^2$ and those receiving PAI-1 DNAzyme had mean lumen areas of $0.231+/-0.028$ $\mu m2$ and mean intimal areas of $0.292+/-0.025$ $\mu m^2$. Therefore, animals receiving saline or scrambled DNA enzyme instillation after balloon angioplasty had neointimal formation that demonstrated mean arterial lumen encroachment of $42+5\%$ and $43+10\%$, whereas those receiving PAI-1 DNA enzyme demonstrated neointimal formation that encroached on only $22+5\%$ of the artery lumen ($p<0.05$). The medial areas of the 3 groups after balloon angioplasty (saline, scrambled DNAzyme, PAI-1 DNAzyme) were not significantly different ($0.281+0.082$ $\mu m^2$ vs $0.247+0.058$ $\mu m^2$ vs $0.292+0.025$ $\mu m^2$)

Next, we examined whether the reduction in neointima formation accompanying PAI-1 DNA enzyme administration resulted from reduction in smooth muscle cellular proliferation. As shown in FIGS. 15 and 16 PAI-1 DNA enzyme significantly inhibited smooth muscle cell proliferation, defined by dual immunostaining for desmin and Ki67 antigens. Animals receiving local instillation of the PAI-1 DNA enzyme demonstrated over 60% reduction in neointimal smooth muscle cell proliferation relative to those receiving either scrambled DNA enzyme or saline (both $p<0.05$). Whereas animals receiving saline or scrambled DNA enzyme instillation after balloon angioplasty demonstrated $80+12$ and $89+20$ replicating smboth muscle cells per high power field, respectively, those receiving PAI-1 DNA enzyme had only $35+6$ replicating smooth muscle cells per high power field in the neointima ($p<0.05$).

Inhibition of PAI-1 and Protein C

Protein C is a serine protease and naturally occurring anti-coagulant that plays a role in the regulation of hemostasis through its ability to block the generation of thrombin production by inactivating Factors Va and VIIIa in the coagulation cascade. Sepsis is defined as a systemic inflammatory response to infection, associated with and mediated by the activation of a number of host defense mechanisms including the cytokine network, leukocytes, and the complement and coagulation/fibrinolysis systems. [Mesters, et al., Blood 88:881-886, 1996]. Disseminated intravascular coagulation (DIC, with widespread deposition of fibrin in the microvasculature of various organs, is an early manifestation of sepsis/septic shock. DIC is an important mediator in the development of the multiple organ failure syndrome and contributes to the poor prognosis of patients with septic shock. [Fourrier, et al., Chest 101:816-823, 1992]. Activated protein C functions as a profibrinolytic factor in a plasminogen activator inhibitor-1 (PAI-1)-dependent manner. Vitronectin, an abundant plasma and platelet glycoprotein has been identified as the cofactor that dramatically improves the ability of activated protein C (APC) to react with PAI-1. Vitronectin enhances the reactivity of APC with PAI-1-300-fold, revealing PAI-1 to be the most efficient inhibitor of APC reported.

Therefore, a method of inhibiting PAI-1 will increase activity of APC and induce increased plasminogen activation. leading to up-regulation of the fibrinolytic cascade.

Materials and Methods

DNA enzymes and RNA substrates: DNA enzymes with 3'-3' inverted thymidine were synthesized by Integrated DNA technologies (Coralville, Iowa) and purified by RNase-free IE-HPLC or RP-HPLC. The short RNA substrates corresponding to target DNA enzyme sequences were chemically synthesized followed by RNAse-free PAGE purification and also made by in vitro transcription from a DNA template.

In vitro transcription: Human PAI-1 cDNA was amplified by RT-PCR from total RNA of cultured HUVEC using the following primer pair: 5'CCAAGAGCGCTGTCAAGAA-GAC3' (forward primer; SEQ ID NO:11) and 5'TCAC-CGTCTGCTTTGGAGACCT3' (reverse primer; SEQ ID NO:12) (position 25-10600, J. Biol. Chem, 1988, 263(19): 9143 ). Length of PCR product is 1598 bases. PAI-1 cDNA was cloned into pGEM-T vector (Promega) to obtain plasmid construct pGEM-hPAI. cDNA sequence was verified using an automatic sequencing machine. A 32P-labeled-nucleotide human PAI-1 RNA transcript was prepared by in vitro transcription (SP6 polymerase, Promega). 20 ml transcription reaction consisted of 4 µl 5×buffer, 2 µl DTT, 1 µl RNasin inhibitor, 4 µl NTP mixture (1 µl A, G, C, and 1 µul $H_2O$), 100 µM UTP, 2 µl template (0.3 µg/µl), a-32P-UTP(10 µci/µl) and 1 µl SP6 polymerase(20 u/µl). Reaction time was 1 hour at 32° C. Unincorporated label and short nucleotides (<350 base) were separated from radiolabeled species by centrifugation on Chromaspin-200 columns (Clontech, Palo Alto, Calif.).

Cleavage reactions: synthetic RNA substrate was end-labeled with 32P using T4 polynucleotide kinase. Cleavage reaction system included 60 mM Tris-HCl(pH 7.5), 10 mM $MgCl_2$, 150 nM NaCl, 0.5 µM 32p-labeled RNA oligo., 0.05-5 µM DNA enzyme. For cleavage of in vitro transcripts, reaction system contained 1% of PAI-1 transcripts, 25 mM Tris-HCl(pH 7.5), 5 mM $MgCl_2$, 100 mM NaCl and 0.2-20 µM DNA enzyme. Reactions were allowed to proceed at 37° C. and were "quenched" by transfer of aliquots to tubes containing 90% formamide, 20 mM EDTA and loading dye. Samples were separated by electrophoresis on TBE-urea denaturing polyacrylamide gels (5% gel for in vitro transcripts and 15% for synthetic RNA) and detected by autoradiography at −80° C.

DNA enzyme stability in serum: DAN enzymes were radiolabled using T4 polynucleotide kinase. Labeling reaction(20 µl of volume) consists of 1 µl 20 µM DNA enzyme, 2 µl 10×kinase buffer, 1 µl T4 PNK(10u/µl), 10 µl $H_2O$, and 6 µl 32P-ATP(3000 uCi/mmol, 10 uCi/µl). Reaction time is 30 minutes at 37° C. HUVEC were cultured in media (Clonetic) containing 2% or 20% FCS, and radiolabeled oligomers were added at a final concentration of 100 nM. Aliquots of the mixture were removed at different time points of 0, 3, 6, 12, 24 hours, quenched with phenol/chloroform and frozen until use. At the end of each experiment, all samples were phenol-extracted and analyzed by 15% denaturing polyacrylamide gels and visualized by autoradiography.

Culture conditions and DNA enzyme transfection: Primary HUVEC endothelial cells were obtained from Clonetic (USA) and grown in medium containing 2% FCS, 100 µg/ml streptomycin and 100 IU/ml penicillin at 37° C. in a humidified atmosphere of 5% CO2. HUVEC were used in experiments between passage 6 and 8. For transfection of DNA enzyme, rat endothelial cells (EC) were harvested and seeded into each well of 6-well plates(~×10$^5$ cells/well). Subconfluent (70-80%) EC were washed twice with 1 ml HEPES buffer (pH7.4) and transfected using 0.5 ml of serum-free-medium containing 1 µM test molecule (E2 or E0) and 20 µg/ml cationic lipids (DOTAP). 3 hours after incubation, 0.5 ml of 2% serum medium were added to each well; 3 hours later, TGFb was added to half the wells at a final concentration of 1.8 ng/ml. Transfected cells continued to be incubated for 8 hrs and were lysed to isolate RNA (for RT-PCR) and Protein (for Western blot) using Trizol reagent (Life Technologies).

RT-PCR: Total RNA from each well of 6-well plates were isolated using 1ml Trizol reagent and dissolved in 20 µl Depc-treated H$_2$O. 2 µl samples were used to perform reverse transcription in 20 µl reaction system, and 4 µl products were then used as templates to amplify PAI-1 or human GAPDH in 50 µl PCR system (5 µl loxbuffer, 1 µl dNTP, 0.25 µl Taq polymerase, 1 µl forward and reverse primer, 38 µl H$_2$O, 2 µl 32 pdCTP (3000 ci/mmol, 10 uci/µl). The reaction conditions were 95° C.-2 min (predenatured), 95° C.-0.5 min, 58° C.-1 min, 72° C.-2 min, 35 cycles, 72° C.-10 min. Human GAPDH was used as internal control (forward Primer 5'TGAAG-GTCGGAGTCAACGGATTTG3'; SEQ ID NO:13, reverse primer 5'CATGTGGGCCATGAGGTCCACCAC3'; SEQ ID NO:14), its PCR. products being 452 base.

Western blot: Control and DNA enzyme-treated cells were harvested, washed with PBS and then the cell pellets were resuspended in lysis buffer and processed. Equal amounts of protein (15 µg/lane) were separated by SDS gel electrophoresis with 10% polyacrylamine separating gel using minigels (Bio-Rad). After electrophoresis, proteins were transferred to nitrocellulose membrane (Protran, Schleicher & Schuell) by electrotransfer and blocked for at least one hour at room temperature with 5% (W/V) BSA in TBS-T buffer (0.1M Tris-base (pH7.5), 0.15M Nacl and 0.1% Tween-20) Following this step, membranes were immunoblotted with goat IgG polyclonal anti-PAI antibodies (Santa Cruz biotech) and then visualised by the ECL-system (Amersham) using horseradish peroxidase conjugated anti-goat IgQ (Sigma).

Measurement of plasmin activity (PAI-1 functional assay): Conditioned medium and cell lysates were collected at various times after interventions. The cells were washed twice with PBS and lysed in 400 ml of 0.5% Triton X-100 for assaying plasmin. Conditioned media and Triton cell lysates were incubated with plasm-n substrate Val—Leu—Lys—pNA (S2251, Kabivitru, Stockholm, Sweden) (final concentration,0.35 mM), in a 96-well microtiter plate (final volume, 200 µl) for 60 min at room temperature. Plasmin activity was measured by reading the absorbance at 410 nm and was calculated against a plasmin (Sigma) standard regression line.

Animals, surgical procedures, injection of human cells, and quantitation of cellular migration into tissues: Rowett (rnu/rnu) athymic nude rats (Harlan Sprague Dawley, Indianapolis, Ind.) were used in studies approved by the "Columbia University Institute for Animal Care and Use Committee". After anesthesia, a left thoracotomy was performed, the pericardium was opened, and the left anterior descending (LAD) coronary artery was ligated. At the time of surgery one group of rats received three intracardiac injections of E2 DNA enzyme, another received three intracardiac injections of E0 scrambled control, and a third group received three intracardiac injections of saline. For studies on neovascularization, 2.0×10$^6$ human cells obtained from a single donor after G-CSF mobilization were reconstituted with 2.0×10$^5$ immunopurified CD$_{34}$+$^{CD117bright}$ cells, and injected into the rat tail vein 48 hours after LAD ligation. Each group consisted of 6-10 rats.

Quantitation of capillary density: In order to quantitate capillary density and species origin of the capillaries, additional sections were stained freshly with mAbs directed against factor VIII, rat or human CD31 (all Serotec, UK), and rat or human MHC class I (Accurate Chemicals, Conn.). Staining was performed by immunoperoxidase technique using an Avidin/Biotin Blocking Kit, a rat-absorbed biotinylated anti-mouse IgG, and a peroxidase-conjugate (all Vector Laboratories Burlingame, Calif.). Capillary density was determined from sections labeled with anti-Factor VIII mAb at 2 weeks post infarction and compared to the capillary density-of the unimpaired myocardium. Values are expressed as factor VIII positive cells per HPF (600×).

Measurement of myocyte apoptosis by DNA end-labeling of paraffin tissue sections: For in situ detection of apoptosis at the single cell level we used the TUNEL method of DNA end-labeling mediated by dexynucleotidyl transferase (TdT) (Boehringer Mannheim, Mannheim, Germany). Rat myocardial tissue sections were obtained from LAD-ligated rats at two weeks after injection of either saline or CD34+ human cells, and from healthy rats as negative controls. Briefly, tissues were deparaffinized with xylene and rehydrated with graded dilutions of ethanol and two washes in phosphate-buffered saline (PBS). The tissue sections were then digested with Proteinase K (10 µg/ml in Tris/HCL) for 30 minutes at 37° C. The slides were then washed 3 times in PBS and incubated with 50 µl of the TUNEL reaction mixture (TdT and fluorescein-labeled dUTP) and incubated in a humid atmosphere for 60 minutes at 37° C. For negative controls TdT was eliminated from the reaction mixture. Following 3 washes in PBS, the sections were then incubated for 30 minutes with an antibody specific for fluorescein-conjugated alkaline phosphatase (AP) (Boehringer Mannheim, Mannheim, Germany). The TUNEL stain was visualized with a substrate system in which nuclei with DNA fragmentation stained blue, (BCIP/NBT substrate system, DAKO, Carpinteria, Calif.). The reaction was terminated following three minutes of exposure with PBS. To determine the proportion of blue-staining apoptotic nuclei within myocytes, tissue was counterstained with a monoclonal antibody specific for desmin. Endogenous peroxidase was blocked by using a 3% hydrogen perioxidase solution in PBS for 15 minutes, followed by washing with 20% goat serum solution. An anti-desmin antibody (Sigma, Saint Louis, Mo.) was incubated overnight (1:100) at 40° C. Following 3 washes sections were then treated with an anti-rabbit IgG, followed by a biotin conjugated secondary antibody for 30 minutes (Sigma, Saint Louis, Mo.). An avidin-biotin complex (Vector Laboratories, Burlingame, Calif.) was then added for an additional 30 minutes and the myocytes were visualized brown following 5 minutes exposure in DAB solution mixture (Sigma, Saint Louis, Mo.). Tissue sections were examined microscopically at 40× magnification and at least 100 cells were counted in a minimum of 8 high-power fields. The percentage of apoptotic myocytes was determined by means of an apoptotic index; the apoptotic index was calculated by dividing the number of positive staining myocyte nuclei by the total number of myocyte nuclei and multiplying by 100. Stained cells at the edges of the tissue were not counted. An apoptotic index of 1 or less was considered to indicate the absence of apoptosis.

Analyses of myocardial function: Echocardiographic studies were performed using a high frequency liner array transducer (SONOS 5500, Hewlett Packard, Andover, Mass.). 2D images were obtained at mid-papillary and apical levels. Enddiastolic (EDV) and end-systolic (ESV) left ventricular volumes were obtained by bi-plane area-length method, and % left ventricular ejection fraction was calculated as [(EDV−ESV)/EDV]×100. Cardiac output (CO) was measured using an ultrasonic flowprobe (Transonic Systems Inc., Ithaca, N.Y.) and cardiac index was calculated as CO per weight. All echocardiographic studies were performed by a blinded investigator (ST).

Rat Model Of Balloon Angioplasty And Carotid Artery Injury: Male Sprague-Dawley rats (weight 350-400 g, Sprague-Dawley Harlan, Indianapolis, Ind.) were anesthetized with ketamine (90 mg/kg i.p.) and xylazine (10 mg/kg i.p.), and a 2F embolectomy balloon catheter (Baxter Health Care) was introduced into the left common carotid artery by way of the external artery. The balloon was inflated with air to distend the common carotid and was then withdrawn to the external artery. This procedure was repeated three times, and the catheter was then removed. After balloon injury of the left common carotid artery, the injured distal segment was isolated by temporary ligature. The PAI-1 or scrambled control DNAzyme was infused into the distal injured segment and incubated for 5 min at room temperature. After incubation, the cannula was removed and blood flow to the common carotid artery was restored. Two weeks after balloon injury, rats were anesthetized and the left and right carotid arteries were removed and embedded in paraffin. Each artery was divided into three segments that were separately embedded in paraffin. Cross-sectional rings (5 µm) were cut from each segment and stained with hematoxylin and eosin. The slides were photographed with a microscope at a magnification of 40×. The lumen, neointima and media area were measured by use of the NIH Image 1.60 software package.) Area measurements were obtained by tracing the lumen perimeter (luminal area [LA], Um2), neointima perimeter (intimal area [IA], Um2), and external elastic lamina (vessel area [VA], Um2). The ratio of intimal area to fracture length (IA/FL) was obtained to correct for extent of injury. Measurements were made by an observer blinded to the treatment.

Morphometric Analysis Of Neointima Formation: Two sections from each carotid artery segment, approximately 3 mm apart, were stained with Masson's trichrome, and intimal and medial areas were measured with computer-assisted planimetry. The mean intimal and medial areas of the 2 sections were calculated for each artery. In 14-day arteries, intimal cell density was measured by counting nuclei in 4 high-power fields in each of 2 sections. The mean density was then calculated for the artery, and, the number of intimal cells was calculated by multiplying intimal area by cell density. Measurements were made by an observer blinded to the treatment.

Measurement Of Smooth Muscle Cell Proliferation: Arterial smooth muscle cell DNA synthesis and cell cycling was determined by dual staining of rat carotid artery tissue sections obtained 14 days after balloon angioplasty and treatment with either PAI-1 DNAzyme or scrambled control DNAzyme. Control carotid arteries were examined from animals who did not undergo balloon angioplasty and from the uninvolved arteries of the experimental animals. Briefly, paraffin embedded sections were microwaved in a 0.1M EDTA buffer, and stained with either a primary monoclonal antibody against rat Ki67 at 1:3000 dilution (gift of Giorgio Catoretti, Columbia University) or human Ki67 at 1:300 dilution (Dako, Calif.) and incubated overnight at 4 degrees C. Following washes, sections were incubated with a species-specific secondary antibody conjugated with alkaline phosphatase at 1:200 dilution (Vector Laboratories Burlingame, Calif.) for 30 minutes and positively-staining nuclei were visualized as blue with a BCIP/NBT substrate kit (Dako, Calif.). Sections were then incubated overnight at 4 degrees C with a monoclonal antibody against desmin (Accurate Chemicals, Conn.) and positively-staining cells were, visualized as brown through the Avidin/Biotin system described above. Smooth muscle cells progressing through cell cycle in the carotid artery intima and media were calculated as the proportion of desmin-positive cells per high power field co-expressing Ki67.

REFERENCES

1. Heymans, S. et al. Inhibition of plasminogen activators or matrix metalloproteinases prevents cardiac rupture but impairs therapeutic angiogenesis and causes cardiac failure. Nat. Med. 5, 1135-1142 (1999).
2. Johnsen, M, Lund, L. R., Romer, J., Almholt, K, and Dano, K. Curr. Opin. Cell. Biol. 10, 667-671 (1998).
3. Lijnen, H. R. et al. Arterioscler. Thromb. Vasc. Biol. 18, 1035-1045 (1998).
4. Steffanson, S, and Lawrence, D. A. Nature 383, 441-443 (1996).
5. Deng, G., royle, G., Wang, S., Crain, K., and Loskutoff, D. J. J. Biol. Chem. 272, 7678-7680 (1996).
6. Stefansson, S. et al. J. Biol. Chem. 273, 6358-6366 (1998).
7. Stefansson, S. et al. J. Biol. Chem. 276, 8135-8141 (2001).
8. Brooks, P. C. et al. Cell 79, 1157-1164 (1994).
9. Brooks, P. C., Clark, R. A. F., and Cheresh, D. A. Science 264, 569-571 (1994).
10. Bennett, M. R., and Schwartz, S. M. Antisense therapy for angioplasty restenosis: some critical considerations. Circulation 92, 1981-1993 (1995).
11. Stein, C. A. Is irrelevant cleavage the price of antisense efficacy? Pharmacology and Therapeutics 85, 231-236 (2000).
12. Simayama, T., Nishikawa, F., Nishikawa, S., and Taira, K. Nuclease-resistant chimeric ribozymes containing deoxyribonucleotides snd phosphorothioate linkages. Nucleic Acid Res. 21, 2605-2611 (1993).
13. Santoro, S. W., and Joyce, G. F. A general purpose RNA-cleaving DNA enzyme. Proc. Natl. Acad. Sci. USA. 94, 4262-4266 (1977).
14. Santiago, F. S., et al. New DNA enzyme targeting Egr-1 mRNA inhibits vascular smooth muscle proliferation and regrowth after injury. Nat Med 5, 1264-1269 (1999).
15. Breaker, R. R. Making catalytic DNAs. Science 290, 2095-2096 (2000).
16. Khachigian, L. M. Catalytic DNAs as potential therapeutic agents and sequence-specific molecular tools to dissect biological function. J Clin Invest 106, 1189-1195 (2000).
17. Zuker, M. On finding all suboptimal foldings of an RNA molecule. Science 244, 48-52 (1989).
18. Soonpaa M H, Field L J. Assessment of cardiomyocyte DNA synthesis in normal and injured adult mouse hearts. Am J Physiol 272, H220-6 (1997).
19. Kellerman S, Moore J A, Zierhut W, Zimmer H G, Campbell J, Gerdes A M. Nuclear DNA content and nucleation patterns in rat cardiac myocytes from different models of cardiac hypertrophy. J Mol Cell Cardiol 24, 497-505 (1992).
20. Kajstura J, Leri A, Finato N, di Loreto N, Beltramo CA, Anversa P. Myocyte proliferation in end-stage cardiac failure in humans. Proc Natl Acad Sci USA 95, 8801-8805 (1998).
21. Beltrami A P, et al. Evidence that human cardiac myocytes divide after myocardial infarction. N Engl J Med 344, 1750-7 (2001).

22. Matzura O, Wennborg A (1996) RNAdraw: an integrated program for RNA secondary structure calculation and analysis under 32-bit Microsoft Windows. *Comput Appl Biosci* 12:247-9.
23. Santoro S W, Joyce G F (1997) A general purpose RNA-cleaving DNA enzyme. *Proc Natl Acad Sci USA* 94:4262-6.
24. Santoro S W, Joyce G F (1998) Mechanism and utility, of an RNA-cleaving DNA enzyme. *Biochemistry* 37:13330-42.
25. Rossi et al., 1992, Aids Research and Human Retroviruses 8, 183.
26. Hampel et al., EP0360257.
27. Hampel and Tritz, 1989 Biochemistry 28, 4929.
28. Hampel et al., 1990 Nucleic Acids Res. 18, 299.
29. Perrotta and Been, 1992-Biochemistry 31, 16.
30. Guerrier-Takada et al., 1983 Cell 35, 849.
31. Forster and Altman, 1990 Science 249, 783.
32. Saville and Collins, 1990 Cell 61, 685-696.
33. Saville and Collins, 1991 Proc. Natl. Acad. Sci. USA 88, 8826-8830.
34. Guo and Collins, 1995 EMBO J. 14, 368.
35. Cech et al., U.S. Pat. No. 4,987,071.
36. M., Andreasen, P. A., Nielsen, L., Dano, K., Lebo, R. V. Gelehrter, T. D. (1986) "cDNA cloning of human plasminogen activator-inhibitor from endothelial cells" J. Clin. Invest. 78(6):1673-1680.
37. Zhang et al. (1995) Clinical Pharmacology & Therapeutics 58(1), 44-53.
38. Sambrook et al., "Molecular Cloning: A Laboratory Manual", Second Edition (1989), Cold Spring Harbor Laboratory Press, Cold Spring Harbor, N.Y.
39. Ma L, Fogo A B. (2001) "Role of angiotensin II in glomerular injury" Semin. Nephrol. 21(6):544-53.
40. Rerolle J P, Hertig A, Nguyen G, Sraer J D, Rondeau E P. (2000) Kidney Int. 58(5):1841-50.
41. Epstein M. (2001) "Aldosterone as a mediator of progressive renal dysfunction: evolving perspectives". Intern. Med. 40(7):573-83.
42. Oda T, Jung Y O, Kim H S, Cai X, Lopez-Guisa J M, Ikeda Y, Eddy A A. (2001) "PAI-1 deficiency attenuates the fibrogenic response to ureteral obstruction." Kidney Int. 60(2):587-96.
43. Tahashi Y, Matsuzaki K, Date M, Yoshida K, Furukawa F, Sugano Y, Matsushita M, Himeno Y, Inagaki Y,Inoue K. (2002) "Differential regulation of TGF-beta signal in hepatic stellate cells between acute and chronic rat liver injury." Hepatology 35(1):49-61.
44. Zhang L P, Takahara T, Yata Y, Furui K, Jin B, Kawada N, Watanabe A. (1999) J. Hepatol. 31(4):703-11.
45. Kotani I, Sato A, Hayakawa H, Urano T, Takada Y, Takada (1999) A. Thromb. Res. 77(6):493-504.

What is claimed is:

1. A method of treating a cardiovascular disease in a subject involving neointima formation in the subject which comprises administering to the subject an amount of a catalytic deoxyribonucleic acid effective to inhibit neointima formation in the subject so as to thereby treat the cardiovascular disease in the subject, wherein the catalytic deoxyribonucleic acid specifically cleaves an mRNA having the sequence set forth in SEQ ID NO:5 encoding a Plasminogen Activator Inhibitor-1 (PAI-1) and comprises, in 5' to 3' order:

(a) consecutive nucleotides defining a first binding domain of at least 4 nucleotides;
   (b) consecutive nucleotides defining a catalytic domain located contiguous with the 3' end of the first binding domain, and capable of cleaving the PAI-1-encoding mRNA at a predetermined phosphodiester bond; and
   (c) consecutive nucleotides defining a second binding domain of at least 4 nucleotides located contiguous with the 3' end of the catalytic domain, wherein the sequence of the nucleotides in each of the first and second binding domains is complementary to a sequence of ribonucleotides in the PAI-1-encoding mRNA and wherein the catalytic deoxyribonucleic acid hybridizes to and specifically cleaves the PAI-1-encoding mRNA, wherein the catalytic deoxyribonucleic acid comprises SEQ ID NO:2, 3 or 4, and wherein the administration is intracarotid administration, or is by intracardiac injection, or is local administration.

2. A method of treating a vascular disease in a subject wherein the disease is treated by reducing thrombin or fibrin production which comprises administering to the subject an inhibitor of PAI-1 expression effective to inhibit PAI-1 expression and thereby reduce thrombin or fibrin production so as to thereby treat the vascular disease in the subject, wherein the inhibitor of PAI-1 expression is a catalytic deoxyribonucleic acid which specifically cleaves an mRNA having the sequence set forth in SEQ ID NO:5 encoding a Plasminogen Activator Inhibitor-1 (PAI-1) and comprises, in 5' to 3' order:
 (a) consecutive nucleotides defining a first binding domain of at least 4 nucleotides;
 (b) consecutive nucleotides defining a catalytic domain located contiguous with the 3' end of the first binding domain, and capable of cleaving the PAI-1-encoding mRNA at a predetermined phosphodiester bond; and
 (c) consecutive nucleotides defining a second binding domain of at least 4 nucleotides located contiguous with the 3' end of the catalytic domain,
 wherein the sequence of the nucleotides in each of the first and second binding domains is complementary to a sequence of ribonucleotides in the PAI-1-encoding mRNA and wherein the catalytic deoxyribonucleic acid hybridizes to and specifically cleaves the PAI-1-encoding mRNA, wherein the catalytic deoxyribonucleic acid comprises SEQ ID NO:2, 3 or 4, and wherein the administration is intracarotid administration, or is by intracardiac injection, or is local administration.

3. A method of inducing neovascularization in a heart tissue of a subject comprising administering to the subject an amount of an inhibitor of PAI-1 expression to the subject effective to inhibit expression of PAI-1 in the heart and thereby induce neovascularization in the heart tissue of the subject, wherein the inhibitor of PAI-1 expression is a catalytic deoxyribonucleic acid which specifically cleaves an mRNA having the sequence set forth in SEQ ID NO:5 encoding a Plasminogen Activator Inhibitor-1 (PAI-1) and comprises, in 5' to 3' order:
 (a) consecutive nucleotides defining a first binding domain of at least 4 nucleotides;
 (b) consecutive nucleotides defining a catalytic domain located contiguous with the 3' end of the first binding domain, and capable of cleaving the PAI-1-encoding mRNA at a predetermined phosphodiester bond; and
 (c) consecutive nucleotides defining a second binding domain of at least 4 nucleotides located contiguous with the 3' end of the catalytic domain,
 wherein the sequence of the nucleotides in each of the first and second binding domains is complementary to a sequence of ribonucleotides in the PAI-1-encoding mRNA and
 wherein the catalytic deoxyribonucleic acid hybridizes to and specifically cleaves the PAI-1-encoding mRNA, wherein the catalytic deoxyribonucleic acid comprises SEQ ID NO:2, 3 or 4, and wherein the administration is intracarotid administration, or is by intracardiac injection, or is local administration.

4. A method of treating a cardiovascular disease in a subject wherein the disease is treated by improving myocardial function in the subject, comprising administering to the subject an amount of a catalytic deoxyribonucleic acid which specifically cleaves an mRNA having the sequence set forth in SEQ ID NO:5 encoding a Plasminogen Activator Inhibitor-1 (PAI-1) and comprises, in 5' to 3' order:
 (a) consecutive nucleotides defining a first binding domain of at least 4 nucleotides;
 (b) consecutive nucleotides defining a catalytic domain located contiguous with the 3' end of the first binding domain, and capable of cleaving the PAI-1-encoding mRNA at a predetermined phosphodiester bond; and
 (c) consecutive nucleotides defining a second binding domain of at least 4 nucleotides located contiguous with the 3' end of the catalytic domain,
 wherein the sequence of the nucleotides in each of the first and second binding domains is complementary to a sequence of ribonucleotides in the PAI-1-encoding mRNA and wherein the catalytic deoxyribonucleic acid hybridizes to and specifically cleaves the PAI-1-encoding mRNA, effective to improve myocardial function and thereby treat the cardiovascular disease in the subject, wherein the catalytic deoxyribonucleic acid comprises SEQ ID NO:2, 3 or 4, and wherein the administration is intracarotid administration, or is by intracardiac injection, or is local administration.

5. A method of inhibiting smooth muscle cell proliferation in a tissue of a subject comprising administering to the subject an amount of a catalytic deoxyribonucleic acid which specifically cleaves an mRNA having the sequence set forth in SEQ ID NO:5 encoding a Plasminogen Activator Inhibitor-1 (PAI-1) and comprises, in 5' to 3' order:
 (a) consecutive nucleotides defining a first binding domain of at least 4 nucleotides;
 (b) consecutive nucleotides defining a catalytic domain located contiguous with the 3' end of the first binding domain, and capable of cleaving the PAI-1-encoding mRNA at a predetermined phosphodiester bond; and
 (c) consecutive nucleotides defining a second binding domain of at least 4 nucleotides located contiguous with the 3' end of the catalytic domain,
 wherein the sequence of the nucleotides in each of the first and second binding domains is complementary to a sequence of ribonucleotides in the PAI-1-encoding mRNA and wherein the catalytic deoxyribonucleic acid hybridizes to and specifically cleaves the PAI-1-encoding mRNA, effective to inhibit smooth muscle cell proliferation in the tissue of the subject, wherein the catalytic deoxyribonucleic acid comprises SEQ ID NO:2, 3 or 4, and wherein the administration is intracarotid administration, or is by intracardiac injection, or is local administration.

6. A method of inhibiting thrombin and fibrin deposition in a heart of a subject comprising administering to the subject an amount of a catalytic deoxyribonucleic acid which specifically cleaves an mRNA having the sequence set forth in SEQ ID NO:5 encoding a Plasminogen Activator Inhibitor-1 (PAI-1) and comprises, in 5' to 3' order:
 (a) consecutive nucleotides defining a first binding domain of at least 4 nucleotides;
 (b) consecutive nucleotides defining a catalytic domain located contiguous with the 3' end of the first binding domain, and capable of cleaving the PAI-1-encoding mRNA at a predetermined phosphodiester bond; and
 (c) consecutive nucleotides defining a second binding domain of at least 4 nucleotides located contiguous with the 3' end of the catalytic domain,
 wherein the sequence of the nucleotides in each of the first and second binding domains is complementary to a sequence of ribonucleotides in the PAI-1-encoding mRNA and wherein the catalytic deoxyribonucleic acid hybridizes to and specifically cleaves the PAI-1-encoding mRNA, effective to inhibit thrombin and fibrin deposition in the heart of the subject, wherein the catalytic deoxyribonucleic acid comprises SEQ ID NO:2, 3 or 4, and wherein the administration is intracarotid administration, or is by intracardiac injection, or is local administration.

7. A method of inhibiting thrombin and fibrin deposition in a tissue of a subject comprising administering to the subject a catalytic deoxyribonucleic acid which specifically cleaves an mRNA having the sequence set forth in SEQ ID NO:5 encoding a Plasminogen Activator Inhibitor-1 (PAI-1) and comprises, in 5' to 3' order:
 (a) consecutive nucleotides defining a first binding domain of at least 4 nucleotides;
 (b) consecutive nucleotides defining a catalytic domain located contiguous with the 3' end of the first binding domain, and capable of cleaving the PAI-1-encoding mRNA at a predetermined phosphodiester bond; and
 (c) consecutive nucleotides defining a second binding domain of at least 4 nucleotides located contiguous with the 3' end of the catalytic domain,
 wherein the sequence of the nucleotides in each of the first and second binding domains is complementary to a sequence of ribonucleotides in the PAI-1-encoding mRNA and wherein the catalytic deoxyribonucleic acid hybridizes to and specifically cleaves the PAI-1-encoding mRNA, effective to inhibit thrombin and fibrin deposition in the tissue of the subject, wherein the catalytic deoxyribonucleic acid comprises SEQ ID NO:2, 3 or 4, and wherein the administration is intracarotid administration, or is by intracardiac injection, or is local administration.

8. A method of treating a vascular disease in a subject comprising administering to the subject an inhibitor of plasminogen activator inhibitor-1 (PAI-1) expression in an amount effective to inhibit PAI-1 expression in the subject and thereby treat the vascular disease, wherein the inhibitor of PAI-1 expression is a catalytic deoxyribonucleic acid which specifically cleaves an mRNA having the sequence set forth in SEQ ID NO:5 encoding a Plasminogen Activator Inhibitor-i (PAI-1) and comprises, in 5' to 3' order:
 (a) consecutive nucleotides defining a first binding domain of at least 4 nucleotides;
 (b) consecutive nucleotides defining a catalytic domain located contiguous with the 3' end of the first binding domain, and capable of cleaving the PAI-1-encoding mRNA at a predetermined phosphodiester bond; and
 (c) consecutive nucleotides defining a second binding domain of at least 4 nucleotides located contiguous with the 3' end of the catalytic domain,
 wherein the sequence of the nucleotides in each of the first and second binding domains is complementary to a sequence of ribonucleotides in the PAI-1-encoding mRNA and wherein the catalytic deoxyribonucleic acid hybridizes to and specifically cleaves the PAI-1-encoding mRNA, wherein the catalytic deoxyribonucleic acid comprises SEQ ID NO:2, 3 or 4, and wherein the administration is intracarotid administration, or is by intracardiac injection, or is local administration.

9. A method of treating carotid artery stenosis or carotid artery injury in a subject which comprises administering to the subject an amount of a catalytic deoxyribonucleic acid effective treat the carotid artery stenosis or carotid artery injury in the subject, wherein the catalytic deoxyribonucleic acid specifically cleaves an mRNA having the sequence set forth in SEQ ID NO:5 encoding a Plasminogen Activator Inhibitor-1 (PAI-1) and comprises, in 5' to 3' order:
 (a) consecutive nucleotides defining a first binding domain of at least 4 nucleotides;
 (b) consecutive nucleotides defining a catalytic domain located contiguous with the 3' end of the first binding domain, and capable of cleaving the PAI-1-encoding mRNA at a predetermined phosphodiester bond; and
 (c) consecutive nucleotides defining a second binding domain of at least 4 nucleotides located contiguous with the 3' end of the catalytic domain,
 wherein the sequence of the nucleotides in each of the first and second binding domains is complementary to a sequence of ribonucleotides in the PAI-1-encoding mRNA and wherein the catalytic deoxyribonucleic acid hybridizes to and specifically cleaves the PAI-1-encoding mRNA, wherein the catalytic deoxyribonucleic acid comprises SEQ ID NO:2, 3 or 4, and wherein the administration is intracarotid administration, or is by intracardiac injection, or is local administration.

10. The method of claim 1, wherein the catalytic deoxyribonucleic acid comprises SEQ ID NO:2.

11. The method of claim 1, wherein the catalytic deoxyribonucleic acid comprises SEQ ID NO:3.

12. The method of claim 1, wherein the catalytic deoxyribonucleic acid comprises SEQ ID NO:4.

13. The method of claim 1, wherein the administration is by intracardiac injection.

14. The method of claim 1, wherein the administration is intracarotid administration.

15. The method of claim 1, wherein the administration is local administration.

16. The method of claim 3, wherein the catalytic deoxyribonucleic acid comprises SEQ ID NO:2.

17. The method of claim 3, wherein the catalytic deoxyribonucleic acid comprises SEQ ID NO:3.

18. The method of claim 3, wherein the catalytic deoxyribonucleic acid comprises SEQ ID NO:4.

19. The method of claim 3, wherein the administration is by intracardiac injection.

20. The method of claim 3, wherein the administration is intracarotid administration.

21. The method of claim 3, wherein the administration is local administration.

22. The method of claim 5, wherein the catalytic deoxyribonucleic acid comprises SEQ ID NO:2.

23. The method of claim 5, wherein the catalytic deoxyribonucleic acid comprises SEQ ID NO:3.

24. The method of claim 5, wherein the catalytic deoxyribonucleic acid comprises SEQ ID NO:4.

25. The method of claim 5, wherein the administration is by intracardiac injection.

26. The method of claim 5, wherein the administration is intracarotid administration.

27. The method of claim 5, wherein the administration is local administration.

28. The method of claim 7, wherein the catalytic deoxyribonucleic acid comprises SEQ ID NO:2.

29. The method of claim 7, wherein the catalytic deoxyribonucleic acid comprises SEQ ID NO:3.

30. The method of claim 7, wherein the catalytic deoxyribonucleic acid comprises SEQ ID NO:4.

31. The method of claim 7, wherein the administration is by intracardiac injection.

32. The method of claim 7, wherein the administration is intracarotid administration.

33. The method of claim 7, wherein the administration is local administration.

34. The method of claim 8, wherein the catalytic deoxyribonucleic acid comprises SEQ ID NO:2.

35. The method of claim 8, wherein the catalytic deoxyribonucleic acid comprises SEQ ID NO:3.

36. The method of claim 8, wherein the catalytic deoxyribonucleic acid comprises SEQ ID NO:4.

37. The method of claim 8, wherein the administration is by intracardiac injection.

38. The method of claim 8, wherein the administration is intracarotid administration.

39. The method of claim 8, wherein the administration is local administration.

40. The method of claim 9, wherein the catalytic deoxyribonucleic acid comprises SEQ ID NO:2.

41. The method of claim 9, wherein the catalytic deoxyribonucleic acid comprises SEQ ID NO:3.

42. The method of claim 9, wherein the catalytic deoxyribonucleic acid comprises SEQ ID NO:4.

43. The method of claim 9, wherein the administration is by intracardiac injection.

44. The method of claim 9, wherein the administration is intracarotid administration.

45. The method of claim 9, wherein the administration is local administration.

* * * * *

```
                            SEQUENCE LISTING

<160> NUMBER OF SEQ ID NOS: 17

<210> SEQ ID NO 1
<211> LENGTH: 15
<212> TYPE: DNA
<213> ORGANISM: ARTIFICIAL SEQUENCE
<220> FEATURE:
<223> OTHER INFORMATION: DNAzyme Catalytic Domain

<400> SEQUENCE: 1
ggctagctac aacga                                                     15

<210> SEQ ID NO 2
<211> LENGTH: 31
<212> TYPE: DNA
<213> ORGANISM: ARTIFICIAL SEQUENCE
<220> FEATURE:
<223> OTHER INFORMATION: DNAzyme for human Plasminogen Activator
      Inhibitor-1

<400> SEQUENCE: 2
catctgcagg ctagctacaa cgacctgaag t                                   31

<210> SEQ ID NO 3
<211> LENGTH: 33
<212> TYPE: DNA
<213> ORGANISM: ARTIFICIAL SEQUENCE
<220> FEATURE:
<223> OTHER INFORMATION: DNAzyme for human Plasminogen Activator
      Inhibitor-1

<400> SEQUENCE: 3
ctggagacag gctagctaca acgactgcat cct                                 33

<210> SEQ ID NO 4
```

```
<211> LENGTH: 31
<212> TYPE: DNA
<213> ORGANISM: ARTIFICIAL SEQUENCE
<220> FEATURE:
<223> OTHER INFORMATION: DNAzyme for Plasminogen Activator Inhibitor

<400> SEQUENCE: 4
gctgaagagg ctagctacaa cgaatctgca t                                   31

<210> SEQ ID NO 5
<211> LENGTH: 2876
<212> TYPE: DNA
<213> ORGANISM: Homo Sapiens

<400> SEQUENCE: 5
gaattcctgc agctcagcag ccgccgccag agcaggacga accgccaatc gcaaggcacc     60
tctgagaact tcaggatgca gatgtctcca gccctcacct gcctagtcct gggcctggcc    120
cttgtctttg gtgaagggtc tgctgtgcac catcccccat cctacgtggc ccacctggcc    180
tcagacttcg gggtgagggt gtttcagcag gtggcgcagg cctccaagga ccgcaacgtg    240
gttttctcac cctatggggt ggcctcggtg ttggccatgc tccagctgac aacaggagga    300
gaaacccagc agcagattca agcagctatg ggattcaaga ttgatgacaa gggcatggcc    360
cccgccctcc ggcatctgta caaggagctc atggggccat ggaacaagga tgagatcagc    420
accacagacg cgatcttcgt ccagcgggat ctgaagctgg tccagggctt catgccccac    480
ttcttcaggc tgttccggag cacggtcaag caagtggact tttcagaggt ggagagagcc    540
agattcatca tcaatgactg ggtgaagaca cacacaaaag gtatgatcag caacttgctt    600
gggaaaggag ccgtggacca gctgacacgg ctggtgctgg tgaatgccct ctacttcaac    660
ggccagtgga gagactccct tcccgactcc agcacccacc gccgcctctt ccacaaatca    720
gacggcagca ctgtctctgt gcccatgatg gctcagacca caagttcaa ctatactgag    780 ttcaccacgc ccgatggcca ttactacgac atcctggaac tgccctacca ggggacacc    840 ctcagcatgt tcattgctgc cccttatgaa aaagaggtgc ctctctctgc cctcaccaac    900
attctgagtg cccagctcat cagccactgg aaaggcaaca tgaccaggct gccccgcctc    960
ctggttctgc ccaagttctc cctggagact gaagtcgacc tcaggaagcc cctagagaac   1020
ctgggaatga ccgacatgtt cagacagttt caggctgact cacgagtct ttcagaccaa   1080 gagcctctcc acgtcgcgca ggcgctgcag aaagtgaaga tcgaggtgaa cgagagtggc   1140
acggtggcct cctcatccac agctgtcata gtctcagccc gcatggcccc cgaggagatc   1200
atcatggaca cccttcct ctttgtggtc cggcacaacc ccacaggaac agtccttttc   1260
atgggccaag tgatggaacc ctgaccctgg ggaaagacgc cttcatctgg acaaaactg   1320 gagatgcatc gggaaagaag aaactccgaa gaaagaatt ttagtgttaa tgactctttc   1380
tgaaggaaga aagacattt gccttttgtt aaaagatggt aaaccagatc tgtctccaag   1440
accttggcct ctccttggag gacctttagg tcaaactccc tagtctccac ctgagaccct   1500
gggagagaag tttgaagcac aactcccttta aggtctccaa accagacggt gacgcctgcg   1560
ggaccatctg gggcacctgc ttccacccgt ctctctgccc actcgggtct gcagacctgg   1620
ttcccactga ggccctttgc aggatggaac tacggggctt acaggagctt ttgtgtgcct   1680
ggtagaaact atttctgttc cagtcacatt gccatcactc ttgtactgcc tgccaccgcg   1740
gaggaggctg gtgacaggcc aaaggccagt ggaagaaaca ccctttcatc tcagagtcca   1800
ctgtggcact ggccaccct ccccagtaca ggggtgctgc aggtggcaga gtgaatgtcc   1860
```

```
cccatcatgt ggcccaactc tcctggcctg gccatctccc tccccagaaa cagtgtgcat    1920
gggttatttt ggagtgtagg tgacttgttt actcattgaa gcagatttct gcttcctttt    1980
atttttatag gaatagagga agaaatgtca gatgcgtgcc cagctcttca ccccccaatc    2040
tcttggtggg gagggtgta cctaaatatt tatcatatcc ttgcccttga gtgcttgtta     2100
gagagaaaga gaactactaa ggaaaataat attatttaaa ctcgctccta gtgtttcttt    2160
gtggtctgtg tcaccgtatc tcaggaagtc cagccacttg actggcacac acccctccgg    2220
acatccagcg tgacggagcc cacactgcca ccttgtggcc gcctgagacc ctcgcgcccc    2280
ccgcgccccc cgcgcccctc ttttccccct tgatggaaat tgaccataca atttcatcct    2340
ccttcagggg atcaaaagga cggagtgggg ggacagagac tcagatgagg acagagtggt    2400
ttccaatgtg ttcaatagat ttaggagcag aaatgcaagg ggctgcatga cctaccagga    2460
cagaactttc cccaattaca gggtgactca cagccgcatt ggtgactcac ttcaatgtgt    2520
catttccggc tgctgtgtgt gagcagtgga cacgtgaggg gggggtgggt gagagagaca    2580
ggcagctcgg attcaactac cttagataat atttctgaaa acctaccagc cagagggtag    2640
ggcacaaaga tggatgtaat gcactttggg aggccaaggc gggaggattg cttgagccca    2700
ggagttcaag accagcctgg gcaacatacc aagaccccg tctctttaaa aatatatata    2760
ttttaaatat acttaaatat atatttctaa tatctttaaa tatatatata tattttaaag    2820
accaatttat gggagaattg cacacagatg tgaaatgaat gtaatctaat agaagc        2876
```

<210> SEQ ID NO 6
<211> LENGTH: 402
<212> TYPE: PRT
<213> ORGANISM: HOMO SAPIENS

<400> SEQUENCE: 6

```
Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
            20                  25                  30

His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190
```

```
Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Thr Ala Val Ile Val Ser Ala
        355                 360                 365

Arg Met Ala Pro Glu Glu Ile Ile Met Asp Arg Pro Phe Leu Phe Val
370                 375                 380

Val Arg His Asn Pro Thr Gly Thr Val Leu Phe Met Gly Gln Val Met
385                 390                 395                 400

Glu Pro

<210> SEQ ID NO 7
<211> LENGTH: 30
<212> TYPE: DNA
<213> ORGANISM: ARTIFICIAL SEQUENCE
<220> FEATURE:
<223> OTHER INFORMATION: SCRAMBLED CONTROL SEQUENCE

<400> SEQUENCE: 7
acactggagg ctagcacaac gatgacgagt                                  30

<210> SEQ ID NO 8
<211> LENGTH: 21
<212> TYPE: RNA
<213> ORGANISM: Homo Sapiens

<400> SEQUENCE: 8
aacuucagga ugcagauguc u                                           21

<210> SEQ ID NO 9
<211> LENGTH: 21
<212> TYPE: RNA
<213> ORGANISM: Homo Sapiens

<400> SEQUENCE: 9
aggaugcaga ugucuccagc c                                           21

<210> SEQ ID NO 10
<211> LENGTH: 22
<212> TYPE: RNA
<213> ORGANISM: Rattus Sp.
```

-continued

```
<400> SEQUENCE: 10
gaugcagaug ucuucagccc uc                                              22

<210> SEQ ID NO 11
<211> LENGTH: 22
<212> TYPE: DNA
<213> ORGANISM: ARTIFICIAL SEQUENCE
<220> FEATURE:
<223> OTHER INFORMATION: PRIMER derived from human source

<400> SEQUENCE: 11
ccaagagcgc tgtcaagaag ac                                              22

<210> SEQ ID NO 12
<211> LENGTH: 22
<212> TYPE: DNA
<213> ORGANISM: ARTIFICIAL SEQUENCE
<220> FEATURE:
<223> OTHER INFORMATION: PRIMER derived from human source

<400> SEQUENCE: 12
tcaccgtctg ctttggagac ct                                              22

<210> SEQ ID NO 13
<211> LENGTH: 24
<212> TYPE: DNA
<213> ORGANISM: ARTIFICIAL SEQUENCE
<220> FEATURE:
<223> OTHER INFORMATION: PRIMER derived from human source

<400> SEQUENCE: 13
tgaaggtcgg agtcaacgga tttg                                            24

<210> SEQ ID NO 14
<211> LENGTH: 24
<212> TYPE: DNA
<213> ORGANISM: ARTIFICIAL SEQUENCE
<220> FEATURE:
<223> OTHER INFORMATION: PRIMER derived from human source

<400> SEQUENCE: 14
catgtgggcc atgaggtcca ccac                                            24

<210> SEQ ID NO 15
<211> LENGTH: 3053
<212> TYPE: DNA
<213> ORGANISM: Rattus Norvegicus

<400> SEQUENCE: 15
cccccgagag ctttgtgaag gaggaacgct gcacacccgc ctcccgcagc acacagccaa     60
ccacagctga gcgacacgca acaagagcca atcacaaggc acttccgaaa gctccaggat    120
gcagatgtct tcagccctca cttgcctcac cctgggcctg gttctggtct ttgggaaagg    180
gttcgcttca ccccttccag agtcccatac agcccagcag ccaccaacct cggagtaaa     240 agtgtttcag catgtggtcc aggcctccaa agaccgaaat gtggtcttct ctccctacgg    300
cgtgtcctcg gtgctggcta tgctgcagct gaccacagca gggaaaaccc ggcagcagat    360
ccaagatgct atgggattca aatatcagtga gggggcaca gctcctgccc tccgaaagct    420
ctccaaggag ctcatggggt catggaacaa gaatgagatc agtactgcgg acgccatctt    480
tgtccagcgg gacctagagc tggtccaggg cttcatgccc cacttcttca gctcttccg     540 gaccacggtg aagcaggtgg acttctcaga ggtggaaaga gccagattca tcatcaacga    600
```

```
ctgggtggag aggcacacca aaggtatgat cagtgactta ctggccaagg gggctgtaaa    660
tgagctgaca cgcctggtgc tggtgaacgc cctctatttc aacggccaat ggaagacccc    720
cttcttagag gccagcaccc accagcgcct gttccacaag tctgatggta gcaccatctc    780
cgtgcccatg atggctcaga caacaagtt caactacact gagttcacca ctccggatgg    840
gcacgagtac gacatcctgg aactgcccta ccacggcgaa accctcagca tgttcattgc    900 agcaccctt gaaaagatg tgcccctctc cgccatcacc aacattttgg acgctgagct    960
catcagacaa tggaagagca acatgaccag gctgccccgc ctcctcatcc tgcctaagtt   1020
ctctctggag actgaagtgg acctcagagg gcccctggag aagctgggca tgactgacat   1080
cttcagctca acccaggccg acttcacaag tctttccgac caagagcagc tctctgtagc   1140
acaagcacta caaaaggtca agatcgaggt gaacgagagc ggcacagtgg cgtcttcctc   1200
cacagccatt ctagtctcag cccgcatggc ccccacggag atggttttag accgatcctt   1260
tctctttgtg gttcggcaca atccaacaga gacaatcctc ttcatgggcc agctgatgga   1320
gccttgagag tgggatgaga agcctttcct ttgggacaaa actggacgtg ttataagcag   1380
agactctgaa gaaaagaatt gttttaagga ctctttgggg agaaagagaa ggcctttctt   1440
tcttaccccg gcactggtaa atcttttccaa ccagcctccc agacctcaga ctctcgaaga   1500
ggaaagagtc taactccctc actagggacc tatcttacta aggtctcatc caaccataga   1560
actcacagaa tctggatctg cccagcattc agcctttgga cccagttccc accaaggccc   1620
cagcagggcc aacccactac gccttcactc agcaaagtct tttgtgttcc agtcacactc   1680
tgggtacctc ttgtatcgtc ctccattgct atgaaggatg acccaggcca aggaagaag   1740 cactgtccta tctcaaggtc cactgtggaa atgaacacct tgcccatccc caaggggcag   1800
cagatagaca gatcgaatga tcgcccgata tcaagccttc tcccagctcc cgtcctgccc   1860
tcccttccct gacagccgcc ttgtgttatt tcagagtgta gatgacttgt ttacagcttt   1920
tttcgaccca caaacttttc tcattttgaa agcgtgaaag aaaggtcaga tgtgcacgtg   1980
ccttgctctt tatcctgggt ctccctgtga ggggagaggg gtcctgggga gattccaggg   2040
gtgtgattga atatttatct tgtttatctt atacgtttgt tggggagaag aagcactatt   2100
aaggagaaag ccttttattt aaaccatggc atatggtgtc ccatttgggg tctgtatccc   2160
tgtatgtcag ggaggcatca ctccacaaac ccgcccctcg ggtggcccgg cgtcggggct   2220
cacactgccg cctagtggca gccgaacacg cccttgcccc atccctcccc cgcatcctcc   2280
cccgtggctc ttttccttag ggatcttgcc aaggtgatgc ttggcagccc acggtaaagg   2340 aaggggaaa aagattaggt gggagagaga gagagagaga gagagagaga gagagagaga   2400
gagagagaga gagagagaga gagagagaga aagagagaga gatgtttgag agagggcaaa   2460
gtggtttcaa attttccaa tacattcaga agccgagtgg gaaaggggggc tgtgtgacct   2520 aacaggacag aactttctcc aattactggg tgactcagct gcactggtga ctcacttcaa   2580
tgtgtcattt ccggctgctg taagtgagca gtggacacgt gggggggggg gggtgaggat   2640
gaaagaaaca gccagctcct ggtcaaccac cttagttaga taatcttttt tgaaagcttc   2700
ctagctgggg gtatgatcag aaaaccaatt tactgaaaaa ctgcacagga aggtaacgtg   2760
aatctaattt catagcgggc cgctctgcat ccgttacatc tccactggaa aaaaataatc   2820
attttctttt tgtgtgtgtg tgtgtgtttt agcttttctc cctctccctc tttctctctc   2880
atttcattat gcactggata accatacacc gtgtaccaca ggggcccaaa tgtggggtca   2940
```

```
catggtcttg aatttgtgg ggtacatatg cctttgtttg tttgttttca cttttgatat    3000
ataaacaggt aaatgtgttt ttaaaaaata ataaaaatag agaatatgca gac           3053
```

<210> SEQ ID NO 16
<211> LENGTH: 402
<212> TYPE: PRT
<213> ORGANISM: Rattus Norvegicus

<400> SEQUENCE: 16

```
Met Gln Met Ser Ser Ala Leu Thr Cys Leu Thr Leu Gly Leu Val Leu
1               5                   10                  15

Val Phe Gly Lys Gly Phe Ala Ser Pro Leu Pro Glu Ser His Thr Ala
            20                  25                  30

Gln Gln Ala Thr Asn Phe Gly Val Lys Val Phe Gln His Val Val Gln
        35                  40                  45

Ala Ser Lys Asp Arg Asn Val Val Phe Ser Pro Tyr Gly Val Ser Ser
    50                  55                  60

Val Leu Ala Met Leu Gln Leu Thr Thr Ala Gly Lys Thr Arg Gln Gln
65                  70                  75                  80

Ile Gln Asp Ala Met Gly Phe Asn Ile Ser Glu Arg Gly Thr Ala Pro
                85                  90                  95

Ala Leu Arg Lys Leu Ser Lys Glu Leu Met Gly Ser Trp Asn Lys Asn
            100                 105                 110

Glu Ile Ser Thr Ala Asp Ala Ile Phe Val Gln Arg Asp Leu Glu Leu
        115                 120                 125

Val Gln Gly Phe Met Pro His Phe Phe Lys Leu Phe Arg Thr Thr Val
    130                 135                 140

Lys Gln Val Asp Phe Ser Glu Val Glu Arg Ala Arg Phe Ile Ile Asn
145                 150                 155                 160

Asp Trp Val Glu Arg His Thr Lys Gly Met Ile Ser Asp Leu Leu Ala
                165                 170                 175

Lys Gly Ala Val Asn Glu Leu Thr Arg Leu Val Leu Val Asn Ala Leu
            180                 185                 190

Tyr Phe Asn Gly Gln Trp Lys Thr Pro Phe Leu Glu Ala Ser Thr His
        195                 200                 205

Gln Arg Leu Phe His Lys Ser Asp Gly Ser Thr Ile Ser Val Pro Met
    210                 215                 220

Met Ala Gln Asn Asn Lys Phe Asn Tyr Thr Glu Phe Thr Thr Pro Asp
225                 230                 235                 240

Gly His Glu Tyr Asp Ile Leu Glu Leu Pro Tyr His Gly Glu Thr Leu
                245                 250                 255

Ser Met Phe Ile Ala Ala Pro Phe Glu Lys Asp Val Pro Leu Ser Ala
            260                 265                 270

Ile Thr Asn Ile Leu Asp Ala Glu Leu Ile Arg Gln Trp Lys Ser Asn
        275                 280                 285

Met Thr Arg Leu Pro Arg Leu Leu Ile Leu Pro Lys Phe Ser Leu Glu
    290                 295                 300

Thr Glu Val Asp Leu Arg Gly Pro Leu Glu Lys Leu Gly Met Thr Asp
305                 310                 315                 320

Ile Phe Ser Ser Thr Gln Ala Asp Phe Thr Ser Leu Ser Asp Gln Glu
                325                 330                 335

Gln Leu Ser Val Ala Gln Ala Leu Gln Lys Val Lys Ile Glu Val Asn
            340                 345                 350

Glu Ser Gly Thr Val Ala Ser Ser Ser Thr Ala Ile Leu Val Ser Ala
```

-continued

```
                355                  360                  365
Arg Met Ala Pro Thr Glu Met Val Leu Asp Arg Ser Phe Leu Phe Val
        370                  375                  380

Val Arg His Asn Pro Thr Glu Thr Ile Leu Phe Met Gly Gln Leu Met
385                  390                  395                  400

Glu Pro
```

<210> SEQ ID NO 17
<211> LENGTH: 1209
<212> TYPE: DNA
<213> ORGANISM: HOMO SAPIENS

<400> SEQUENCE: 17

```
atgcagatgt ctccagccct cacctgccta gtcctgggcc tggcccttgt ctttggtgaa      60
gggtctgctg tgcaccatcc cccatcctac gtggcccacc tggcctcaga cttcggggtg     120
agggtgtttc agcaggtggc gcaggcctcc aaggaccgca acgtggtttt ctcaccctat     180
ggggtggcct cggtgttggc catgctccag ctgacaacag gaggagaaac ccagcagcag     240
attcaagcag ctatgggatt caagattgat gacaagggca tggcccccgc cctccggcat     300
ctgtacaagg agctcatggg gccatggaac aaggatgaga tcagcaccac agacgcgatc     360
ttcgtccagc gggatctgaa gctggtccag ggcttcatgc cccacttctt caggctgttc     420
cggagcacgg tcaagcaagt ggactttca gaggtggaga gagccagatt catcatcaat     480
gactgggtga agacacacac aaaaggtatg atcagcaact tgcttgggaa aggagccgtg     540
gaccagctga cacggctggt gctggtgaat gccctctact tcaacggcca gtggaagact     600
cccttccccg actccagcac ccaccgccgc ctcttccaca aatcagacgg cagcactgtc     660
tctgtgccca tgatggctca gaccaacaag ttcaactata ctgagttcac cacgcccgat     720
ggccattact acgacatcct ggaactgccc taccacgggg acaccctcag catgttcatt     780
gctgccctt atgaaaaaga ggtgcctctc tctgccctca ccaacattct gagtgcccag     840
ctcatcagcc actggaaagg caacatgacc aggctgcccc gcctcctggt tctgcccaag     900
ttctccctgg agactgaagt cgacctcagg aagcccctag agaacctggg aatgaccgac     960
atgttcagac agtttcaggc tgacttcacg agtctttcag accaagagcc tctccacgtc    1020
gcgcaggcgc tgcagaaagt gaagatcgag gtgaacgaga gtggcacggt ggcctcctca    1080
tccacagctg tcatagtctc agcccgcatg gcccccgagg agatcatcat ggacagaccc    1140
ttcctctttg tggtccggca caaccccaca ggaacagtcc ttttcatggg ccaagtgatg    1200
gaaccctga                                                             1209
```